(12) United States Patent
Esteban

(10) Patent No.: US 11,104,645 B2
(45) Date of Patent: Aug. 31, 2021

(54) ORGANIC MOLECULES FOR USE IN OPTOELECTRONIC DEVICES

(71) Applicant: CYNORA GMBH, Bruchsal (DE)

(72) Inventor: Alhama Arjona Esteban, Karlsruhe (DE)

(73) Assignee: CYNORA GmbH, Bruchsal (DE)

( * ) Notice: Subject to any disclaimer, the term of this patent is extended or adjusted under 35 U.S.C. 154(b) by 381 days.

(21) Appl. No.: 16/358,878

(22) Filed: Mar. 20, 2019

(65) Prior Publication Data

US 2019/0292151 A1   Sep. 26, 2019

(30) Foreign Application Priority Data

Mar. 26, 2018   (DE) ...................... 10 2018 107166.3

(51) Int. Cl.
   *C07D 209/86*   (2006.01)
   *C07D 219/14*   (2006.01)
       (Continued)

(52) U.S. Cl.
   CPC ......... *C07D 209/86* (2013.01); *C07D 519/00* (2013.01); *H01L 51/0067* (2013.01);
       (Continued)

(58) Field of Classification Search
   CPC . C07D 209/86; C07D 219/14; H01L 51/0067; H01L 51/0072
   See application file for complete search history.

(56) References Cited

U.S. PATENT DOCUMENTS 10,263,196 B2 * 4/2019 Danz .................. H01L 51/0071
2017/0369439 A1 12/2017 Jung et al.

FOREIGN PATENT DOCUMENTS

| CN | 106966955 A | 7/2017 |
| DE | 102016113784 A | 6/2017 |
| WO | 2015199303 A1 | 12/2015 |

OTHER PUBLICATIONS

SciFinder Search (Year: 2021).*

* cited by examiner

*Primary Examiner* — Vu A Nguyen
(74) *Attorney, Agent, or Firm* — Ryan, Mason & Lewis, LLP

(57) ABSTRACT

An organic molecule is disclosed having a structure of formula I, wherein
T is selected from the group consisting of CN and $CF_3$;
V, W and Y is independently from each other selected from the group consisting of CN, $CF_3$ and $R^2$;
Z is at each occurrence independently from another selected from the group consisting of a direct bond, $CR^3R^4$, $C=CR^3R^4$, $C=O$, $C=NR^3$, $NR^3$, O, $SiR^3R^4$, S, S(O) and $S(O)_2$;
wherein
exactly one substituent selected from the group consisting of T, V, W and Y is CN; and (Continued)

exactly one substituent selected from the group consisting of T, V, W and Y is $CF_3$.

20 Claims, 1 Drawing Sheet

(51) Int. Cl.
    *C07D 519/00*     (2006.01)
    *H01L 51/00*     (2006.01)
    *H01L 51/50*     (2006.01)

(52) U.S. Cl.
    CPC ........ *H01L 51/0072* (2013.01); *H01L 51/001* (2013.01); *H01L 51/5012* (2013.01)

ORGANIC MOLECULES FOR USE IN OPTOELECTRONIC DEVICES

CROSS-REFERENCE TO RELATED APPLICATIONS

This application claims priority to German Patent Application No. 10 2018 107 166.3, filed Mar. 26, 2018, the disclosure of which is incorporated by reference herein in its entireties.

FIELD OF INVENTION

The invention relates to organic molecules and their use in organic light-emitting diodes (OLEDs) and in other optoelectronic devices.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS OF THE INVENTION

Figure 1:
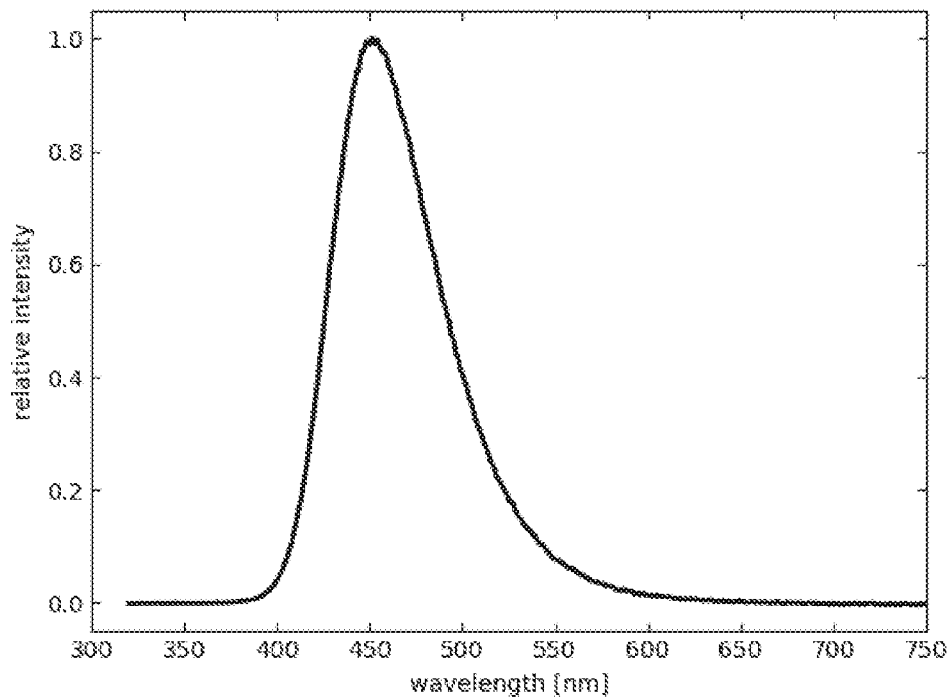
FIG. 1 is an emission spectrum of Example 1 (10% by weight) in PMMA.

Exemplary embodiments of the invention will now be discussed in further detail. This invention may, however, be embodied in many different forms and should not be construed as limited to the embodiments set forth herein.

The object of the present invention is to provide molecules which are suitable for use in organic optoelectronic devices.

This object is achieved by the invention which provides a new class of organic molecules.

According to the invention the organic molecules are purely organic molecules, i.e. they do not contain any metal ions in contrast to metal complexes known for use in organic optoelectronic devices.

According to the present invention, the organic molecules exhibit emission maxima in the blue, sky-blue or green spectral range. The organic molecules exhibit in particular emission maxima between 420 nm and 520 nm, preferably between 440 nm and 495 nm, more preferably between 450 nm and 470 nm. The photoluminescence quantum yields of the organic molecules according to the invention are, in particular, 20% or more. The molecules according to the invention exhibit in particular thermally activated delayed fluorescence (TADF). The use of the molecules according to the invention in an optoelectronic device, for example an organic light-emitting diode (OLED), leads to higher efficiencies of the device. Corresponding OLEDs have a higher stability than OLEDs with known emitter materials and comparable color.

The organic light-emitting molecules of the invention comprise or consist of a structure of Formula I,

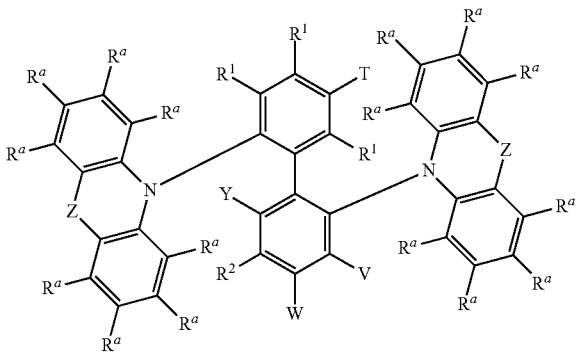

Formula I

T is selected from the group consisting of CN and $CF_3$.

V, W and Y is independently from each other selected from the group consisting of CN, $CF_3$ and $R^2$.

Z is at each occurrence independently from another selected from the group consisting of a direct bond, $CR^3R^4$, $C=CR^3R^4$, $C=O$, $C=NR^3$, $NR^3$, O, $SiR^3R^4$, S, S(O) and $S(O)_2$.

$R^1$ is at each occurrence independently from another selected from the group consisting of hydrogen,
  deuterium,
  $C_1$-$C_5$-alkyl,
    wherein one or more hydrogen atoms are optionally substituted by deuterium;
  $C_2$-$C_8$-alkenyl,
    wherein one or more hydrogen atoms are optionally substituted by deuterium;
  $C_2$-$C_8$-alkynyl,
    wherein one or more hydrogen atoms are optionally substituted by deuterium; and
  $C_6$-$C_{18}$-aryl,
    which is optionally substituted with one or more substituents independently from each other selected from the group consisting of Me, $^iPr$, $^tBu$ and Ph.

$R^2$ is at each occurrence independently from another selected from the group consisting of hydrogen,
  deuterium,
  $C_1$-$C_5$-alkyl,
    wherein one or more hydrogen atoms are optionally substituted by deuterium;
  $C_2$-$C_8$-alkenyl,
    wherein one or more hydrogen atoms are optionally substituted by deuterium;
  $C_2$-$C_8$-alkynyl,
    wherein one or more hydrogen atoms are optionally substituted by deuterium; and
  $C_6$-$C_{18}$-aryl,
    which is optionally substituted with one or more substituents independently from each other selected from the group consisting of Me, $^iPr$, $^tBu$ and Ph.

$R^a$, $R^3$ and $R^4$ is at each occurrence independently from another selected from the group consisting of hydrogen, deuterium, $N(R^5)_2$, $OR^5$, $Si(R^5)_3$, $B(OR^5)_2$, $OSO_2R^5$, $CF_3$, CN, F, Br, I,
  $C_1$-$C_{40}$-alkyl,
    which is optionally substituted with one or more substituents $R^5$ and
    wherein one or more non-adjacent $CH_2$-groups are optionally substituted by $R^5C=CR^5$, $C\equiv C$, $Si(R^5)_2$, $Ge(R^5)_2$, $Sn(R^5)_2$, C=O, C=S, C=Se, C=NR$^5$, P(=O)(R$^5$), SO, SO$_2$, NR$^5$, O, S or CONR$^5$;

$C_1$-$C_{40}$-alkoxy,
  which is optionally substituted with one or more substituents R$^5$ and
  wherein one or more non-adjacent CH$_2$-groups are optionally substituted by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

$C_1$-$C_{40}$-thioalkoxy,
  which is optionally substituted with one or more substituents R$^5$ and
  wherein one or more non-adjacent CH$_2$-groups are optionally substituted by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

$C_2$-$C_{40}$-alkenyl,
  which is optionally substituted with one or more substituents R$^5$ and
  wherein one or more non-adjacent CH$_2$-groups are optionally substituted by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

$C_2$-$C_{40}$-alkynyl,
  which is optionally substituted with one or more substituents R$^5$ and
  wherein one or more non-adjacent CH$_2$-groups are optionally substituted by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$;

$C_6$-$C_{60}$-aryl,
  which is optionally substituted with one or more substituents R$^5$; and $C_3$-$C_{57}$-heteroaryl,
  which is optionally substituted with one or more substituents R$^5$.

R$^6$ is at each occurrence independently from another selected from the group consisting of hydrogen, deuterium, N(R$^6$)$_2$, OR$^6$, Si(R$^6$)$_3$, B(OR$^6$)$_2$, OSO$_2$R$^6$, CF$_3$, CN, F, Br, I, $C_1$-$C_{40}$-alkyl,
  which is optionally substituted with one or more substituents R$^6$ and
  wherein one or more non-adjacent CH$_2$-groups are optionally substituted by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;

$C_1$-$C_{40}$-alkoxy,
  which is optionally substituted with one or more substituents R$^6$ and
  wherein one or more non-adjacent CH$_2$-groups are optionally substituted by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;

$C_1$-$C_{40}$-thioalkoxy,
  which is optionally substituted with one or more substituents R$^6$ and
  wherein one or more non-adjacent CH$_2$-groups are optionally substituted by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;

$C_2$-$C_{40}$-alkenyl,
  which is optionally substituted with one or more substituents R$^6$ and
  wherein one or more non-adjacent CH$_2$-groups are optionally substituted by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;

$C_2$-$C_{40}$-alkynyl,
  which is optionally substituted with one or more substituents R$^6$ and
  wherein one or more non-adjacent CH$_2$-groups are optionally substituted by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$;

$C_6$-$C_{60}$-aryl,
  which is optionally substituted with one or more substituents R$^6$; and $C_3$-$C_{57}$-heteroaryl,
  which is optionally substituted with one or more substituents R$^6$.

R$^6$ is at each occurrence independently from another selected from the group consisting of hydrogen, deuterium, OPh, CF$_3$, CN, F, $C_1$-$C_5$-alkyl,
  wherein optionally one or more hydrogen atoms are independently from each other substituted by deuterium, CN, CF$_3$, or F;

$C_1$-$C_5$-alkoxy,
  wherein optionally one or more hydrogen atoms are independently from each other substituted by deuterium, CN, CF$_3$, or F;

$C_1$-$C_5$-thioalkoxy,
  wherein optionally one or more hydrogen atoms are independently from each other substituted by deuterium, CN, CF$_3$, or F;

$C_2$-$C_5$-alkenyl,
  wherein optionally one or more hydrogen atoms are independently from each other substituted by deuterium, CN, CF$_3$, or F;

$C_2$-$C_5$-alkynyl,
  wherein optionally one or more hydrogen atoms are independently from each other substituted by deuterium, CN, CF$_3$, or F;

$C_6$-$C_{18}$-aryl,
  which is optionally substituted with one or more C≡C-alkyl substituents;

$C_3$-$C_{17}$-heteroaryl,
  which is optionally substituted with one or more C≡C-alkyl substituents;

N($C_6$-$C_{18}$-aryl)$_2$,

N($C_3$-$C_{17}$-heteroaryl)$_2$; and

N($C_3$-$C_{17}$-heteroaryl)($C_6$-$C_{18}$-aryl).

According to the invention, exactly one (one and only one) substituent selected from the group consisting of T, V, W and Y is CN;

and exactly one substituent selected from the group consisting of T, V, W and Y is CF$_3$.

In a further embodiment of the invention, the organic molecule comprises or consists of a structure of Formula Ia:

Formula Ia

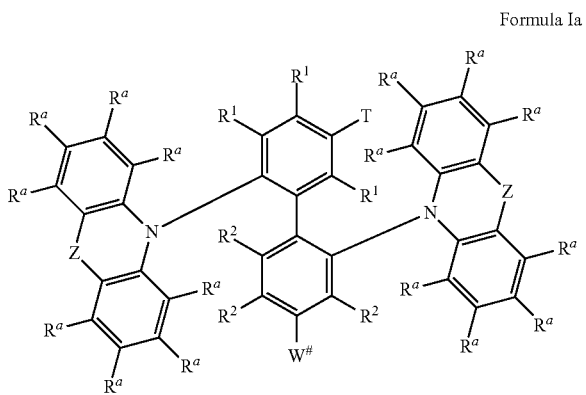

wherein
$W^{\#}$ is selected from the group consisting of CN and $CF_3$,
wherein exactly one substituent selected from the group consisting of T and W is CN;
and exactly one (i.e. the other) substituent selected from the group consisting of T and W is $CF_3$; and wherein the aforementioned definitions apply.

In a further embodiment of the invention, the organic molecule comprises or consists of a structure of Formula IIa:

Formula IIa

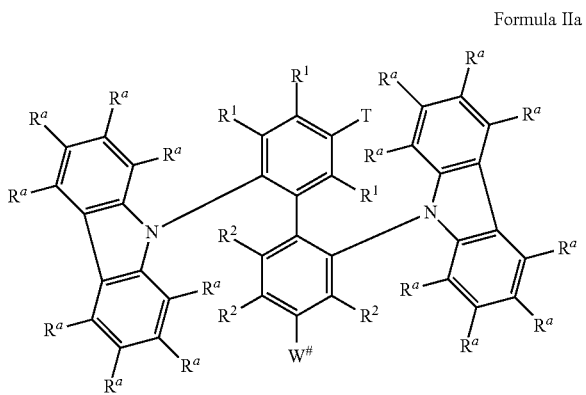

wherein
$W^{\#}$ is selected from the group consisting of CN and $CF_3$,
wherein exactly one substituent selected from the group consisting of T and $W^{\#}$ is CN; and exactly one (i.e. the other) substituent selected from the group consisting of T and $W^{\#}$ is $CF_3$; and wherein the aforementioned definitions apply.

In one embodiment, $R^1$ and $R^2$ is at each occurrence independently from another selected from the group consisting of hydrogen (H), methyl, mesityl, tolyl and phenyl. The term tolyl comprises 2-tolyl, 3-tolyl and 4-tolyl.

In one embodiment, $R^1$ and $R^2$ is at each occurrence independently from another selected from the group consisting of hydrogen (H), methyl, and phenyl.

In one embodiment, $R^1$ and $R^2$ is hydrogen (H).
In one embodiment, T is CN and V is $CF_3$.
In one embodiment, T is CN and W is $CF_3$.
In one embodiment, T is CN and Y is $CF_3$.
In one embodiment, T is $CF_3$ and V is CN.
In one embodiment, T is $CF_3$ and W is CN.
In one embodiment, T is $CF_3$ and Y is CN.

In a further embodiment of the invention, $R^a$ is at each occurrence independently from another selected from the group consisting of H, Me,
$^iPr$,
$^tBu$,
CN,
$CF_3$,
Ph, which is optionally substituted with one or more substituents independently from each other selected from the group consisting of Me, $^iPr$, $^tBu$, ON, $CF_3$, and Ph,
pyridinyl, which is optionally substituted with one or more substituents independently from each other selected from the group consisting of Me, Pr, $^tBu$, ON, $CF_3$, and Ph,
pyrimidinyl, which is optionally substituted with one or more substituents independently from each other selected from the group consisting of Me, Pr, $^tBu$, ON, $CF_3$, and Ph,
carbazolyl, which is optionally substituted with one or more substituents independently from each other selected from the group consisting of Me, Pr, $^tBu$, ON, $CF_3$, and Ph,
triazinyl, which is optionally substituted with one or more substituents independently from each other selected from the group consisting of Me, Pr, $^tBu$, ON, $CF_3$, and Ph,
and $N(Ph)_2$.

In a further embodiment of the invention, $R^a$ is at each occurrence independently from another selected from the group consisting of H,
Me,
$^iPr$,
$^tBu$,
CN,
$CF_3$,
Ph, which is optionally substituted with one or more substituents independently from each other selected from the group consisting of Me, $^iPr$, $^tBu$, ON, $CF_3$, and Ph,
pyridinyl, which is optionally substituted with one or more substituents independently from each other selected from the group consisting of Me, Pr, $^tBu$, ON, $CF_3$, and Ph,
pyrimidinyl, which is optionally substituted with one or more substituents independently from each other selected from the group consisting of Me, Pr, $^tBu$, ON, $CF_3$, and Ph, and
triazinyl, which is optionally substituted with one or more substituents independently from each other selected from the group consisting of Me, Pr, $^tBu$, ON, $CF_3$, and Ph.

In a further embodiment of the invention, $R^a$ is at each occurrence independently from another selected from the group consisting of H,
Me,
$^tBu$,
Ph, which is optionally substituted with one or more substituents independently from each other selected from the group consisting of Me, $^iPr$, $^tBu$, ON, $CF_3$, and Ph,
triazinyl, which is optionally substituted with one or more substituents independently from each other selected from the group consisting of Me, $^iPr$, $^tBu$, CN, $CF_3$, and Ph.

In a further embodiment of the invention, $R^a$ is H at each occurrence

In a further embodiment of the invention, the organic molecule comprises or consists of a structure selected from the group of Formula lib, Formula IIb-2, Formula IIb-3 or Formula IIb-4:

Formula IIb

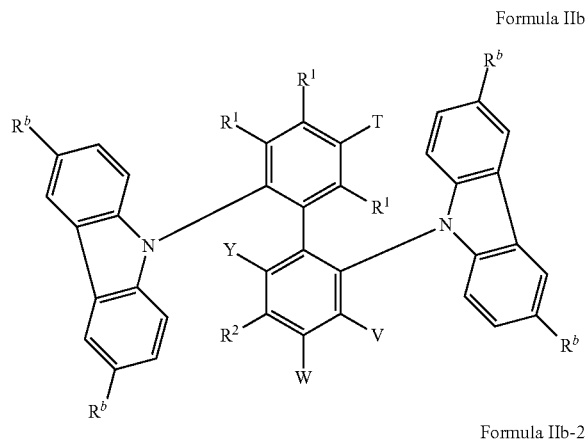

Formula IIb-2

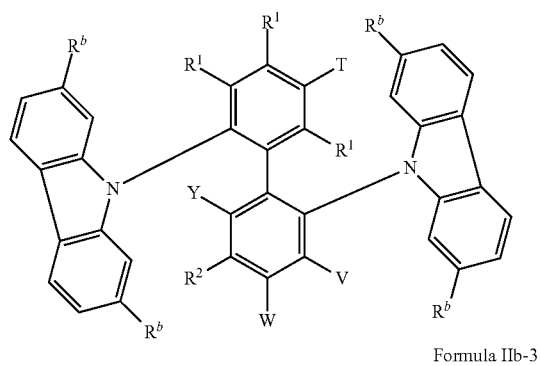

Formula IIb-3

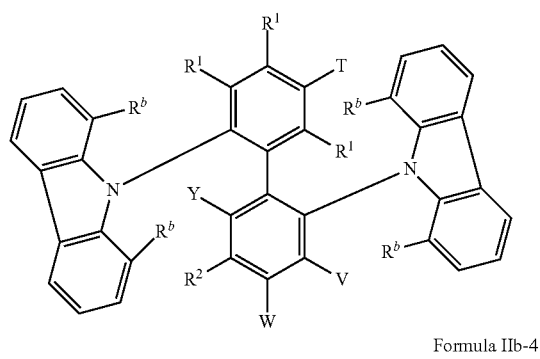

Formula IIb-4

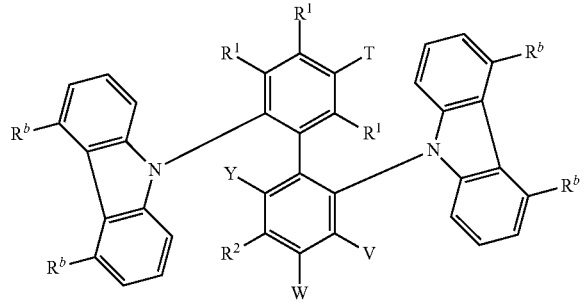

wherein
$R^b$ is at each occurrence independently from another selected from the group consisting of deuterium,
$N(R^5)_2$,
$OR^5$,
$Si(R^5)_3$,
$B(OR^5)_2$,
$OSO_2R^5$,
$CF_3$,
CN,
F,
Br,
I,
$C_1$-$C_{40}$-alkyl,
    which is optionally substituted with one or more substituents $R^5$ and
    wherein one or more non-adjacent $CH_2$-groups are optionally substituted by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_1$-$C_{40}$-alkoxy,
    which is optionally substituted with one or more substituents $R^5$ and
    wherein one or more non-adjacent $CH_2$-groups are optionally substituted by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_1$-$C_{40}$-thioalkoxy,
    which is optionally substituted with one or more substituents $R^5$ and
    wherein one or more non-adjacent $CH_2$-groups are optionally substituted by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_2$-$C_{40}$-alkenyl,
    which is optionally substituted with one or more substituents $R^5$ and
    wherein one or more non-adjacent $CH_2$-groups are optionally substituted by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_2$-$C_{40}$-alkynyl,
    which is optionally substituted with one or more substituents $R^5$ and
    wherein one or more non-adjacent $CH_2$-groups are optionally substituted by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_6$-$C_{60}$-aryl,
    which is optionally substituted with one or more substituents $R^5$; and
$C_3$-$C_{57}$-heteroaryl,
    which is optionally substituted with one or more substituents $R^5$.

Apart from that the aforementioned definitions apply.

In a further embodiment of the invention, the organic molecule comprises or consists of a structure selected from the group of Formula IIc, Formula IIc-2, Formula IIc-3 or Formula IIc-4:

Formula IIc

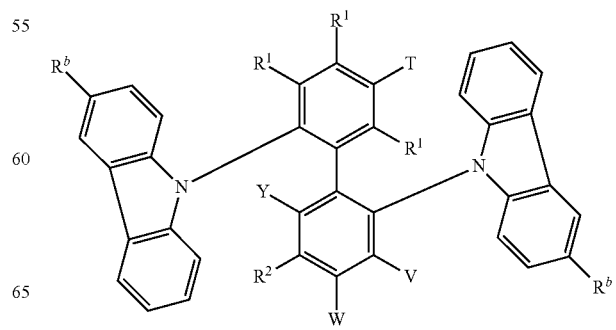

-continued

Formula Ic-2

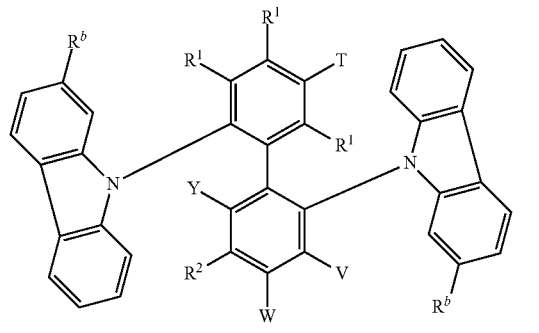

Formula IIc-3

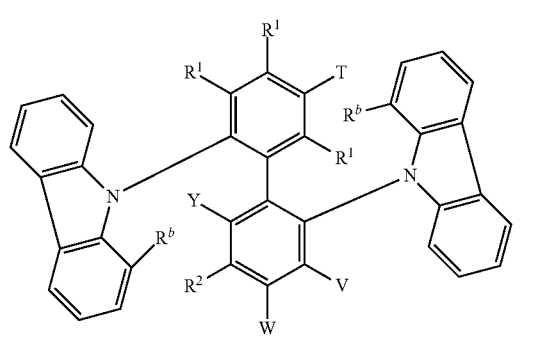

Formula IIc-4

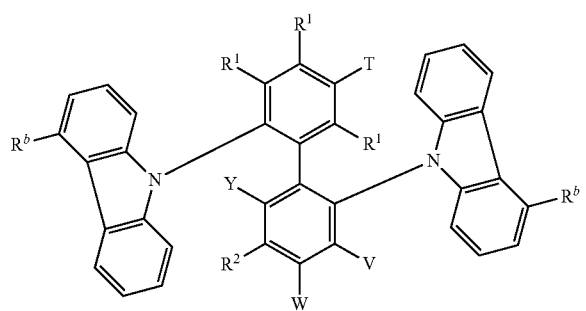

wherein the aforementioned definitions apply.

In a further embodiment of the invention, $R^b$ is at each occurrence independently from another selected from the group consisting of
Me,
$^i$Pr,
$^t$Bu,
CN,
$CF_3$,
Ph, which is optionally substituted with one or more substituents independently from each other selected from the group consisting of Me, $^i$Pr, $^t$Bu, ON, $CF_3$, and Ph,
pyridinyl, which is optionally substituted with one or more substituents independently from each other selected from the group consisting of Me, Pr, $^t$Bu, ON, $CF_3$, and Ph,
carbazolyl, which is optionally substituted with one or more substituents independently from each other selected from the group consisting of Me, Pr, $^t$Bu, ON, $CF_3$, and Ph,
triazinyl, which is optionally substituted with one or more substituents independently from each other selected from the group consisting of Me, Pr, $^t$Bu, ON, $CF_3$, and Ph,
and $N(Ph)_2$.

In a further embodiment of the invention, $R^b$ is at each occurrence independently from another selected from the group consisting of
Me,
$^i$Pr,
$^t$Bu,
CN,
$CF_3$,
Ph, which is optionally substituted with one or more substituents independently from each other selected from the group consisting of Me, $^i$Pr, $^t$Bu, ON, $CF_3$, and Ph,
pyridinyl, which is optionally substituted with one or more substituents independently from each other selected from the group consisting of Me, Pr, $^t$Bu, ON, $CF_3$, and Ph,
pyrimidinyl, which is optionally substituted with one or more substituents independently from each other selected from the group consisting of Me, Pr, $^t$Bu, ON, $CF_3$, and Ph, and
triazinyl, which is optionally substituted with one or more substituents independently from each other selected from the group consisting of Me, Pr, $^t$Bu, ON, $CF_3$, and Ph.

In a further embodiment of the invention, $R^b$ is at each occurrence independently from another selected from the group consisting of
Me,
$^t$Bu,
Ph, which is optionally substituted with one or more substituents independently from each other selected from the group consisting of Me, $^i$Pr, $^t$Bu, ON, $CF_3$, and Ph,
triazinyl, which is optionally substituted with one or more substituents independently from each other selected from the group consisting of Me, Pr, $^t$Bu, ON, $CF_3$, and Ph.

In the following, exemplary embodiments of the organic molecule of the invention are shown:

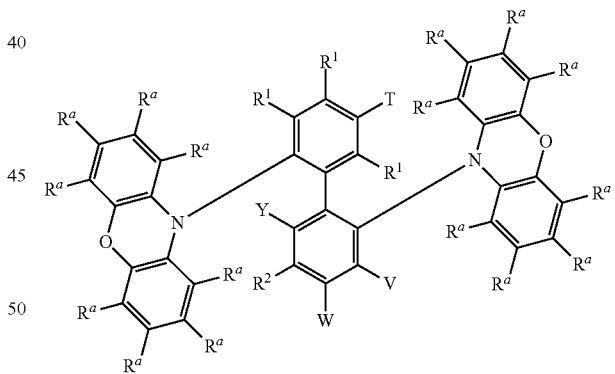

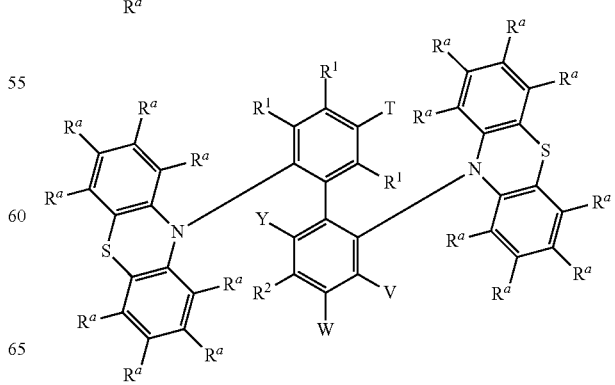

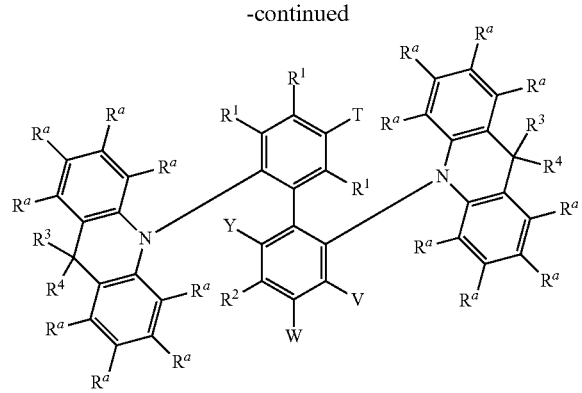
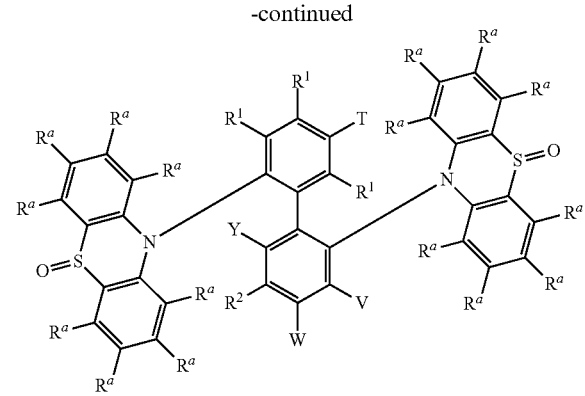
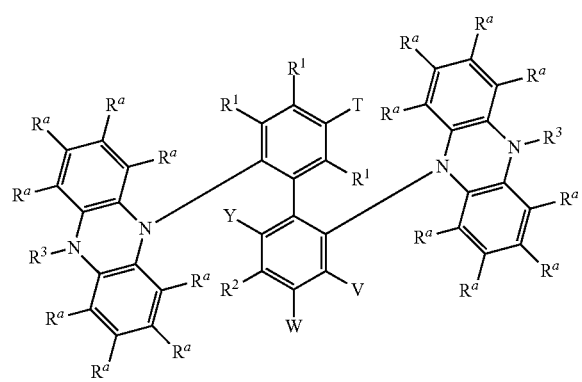
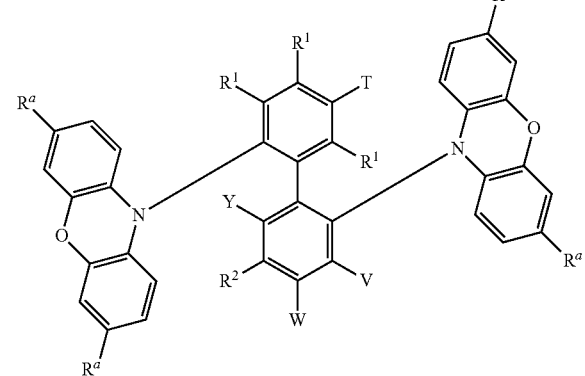
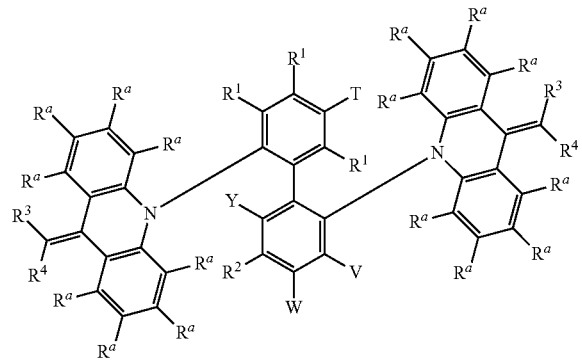
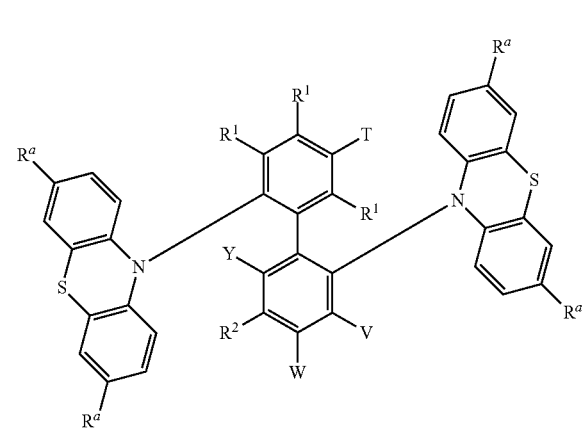
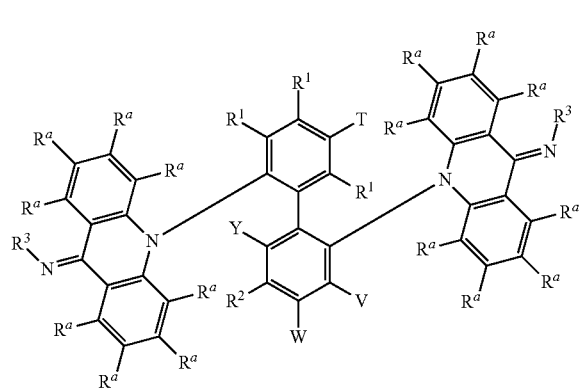
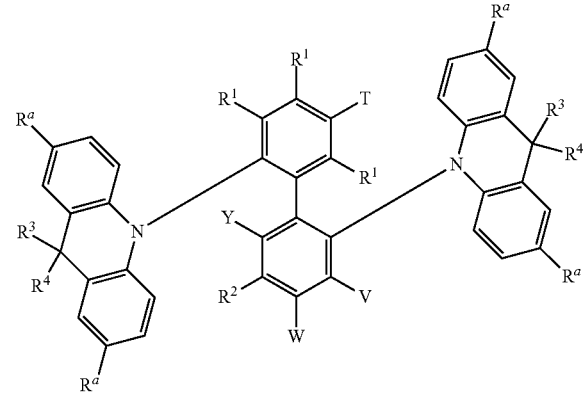

-continued

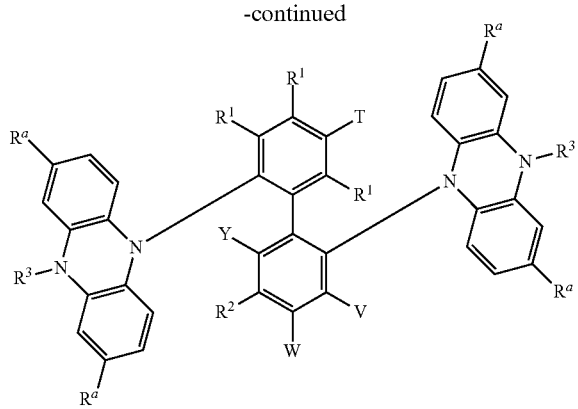

wherein for W, V, Y, $R^1$, $R^2$, $R^a$, $R^3$, $R^4$ and $R^5$ the aforementioned definitions apply.

In one embodiment, $R^a$ and $R^5$ is at each occurrence independently from another selected from the group consisting of hydrogen (H), methyl (Me), i-propyl ($CH(CH_3)_2$) ($^iPr$), t-butyl ($^tBu$), phenyl (Ph), CN, $CF_3$, and diphenylamine ($NPh_2$).

In one embodiment of the invention, the organic molecules comprise or consist of a structure of Formula III:

Formula III wherein the aforementioned definitions apply.

In a further embodiment of the invention, the organic molecules comprise or consist of a structure selected from the group of Formula IIIa:

Formula IIIa wherein
$R^C$ is at each occurrence independently from another selected from the group consisting of Me,
$^iPr$,
$^tBu$,
Ph, which is optionally substituted with one or more substituents independently from each other selected from the group consisting of Me, $^iPr$, $^tBu$, ON, $CF_3$, and Ph,
pyridinyl, which is optionally substituted with one or more substituents independently from each other selected from the group consisting of Me, Pr, $^tBu$, CN, $CF_3$, and Ph,
pyrimidinyl, which is optionally substituted with one or more substituents independently from each other selected from the group consisting of Me, Pr, $^tBu$, CN, $CF_3$, and Ph,
carbazolyl, which is optionally substituted with one or more substituents independently from each other selected from the group consisting of Me, Pr, $^tBu$, CN, $CF_3$, and Ph,
triazinyl, which is optionally substituted with one or more substituents independently from each other selected from the group consisting of Me, Pr, $^tBu$, CN, $CF_3$, and Ph,
and $N(Ph)_2$.

In a further embodiment of the invention, the organic molecules comprise or consist of a structure selected from the group of Formula IIIb:

Formula IIIb wherein the aforementioned definitions apply.

In a further embodiment of the invention, the organic molecules comprise or consist of a structure selected from the group of Formula IIIc:

Formula IIIc wherein the aforementioned definitions apply.

In a further embodiment of the invention, the organic molecules comprise or consist of a structure selected from the group of Formula IIId:

Formula IIId

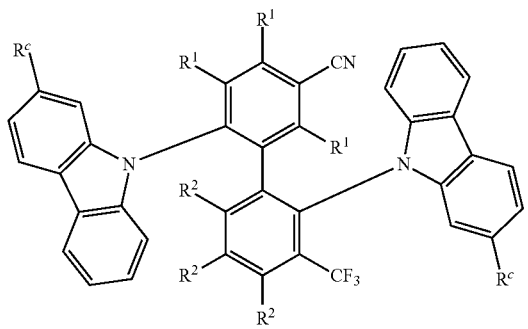

wherein the aforementioned definitions apply.

In one embodiment of the invention, the organic molecules comprise or consist of a structure of Formula IV:

Formula IV

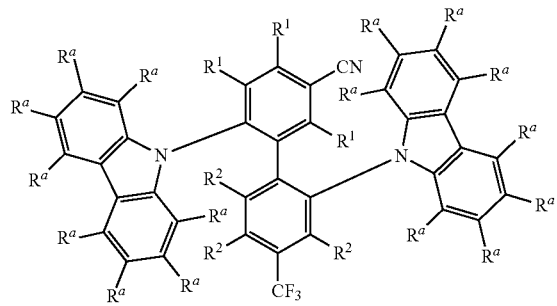

wherein the aforementioned definitions apply.

In a further embodiment of the invention, the organic molecules comprise or consist of a structure selected from the group of Formula IVa:

Formula IVa

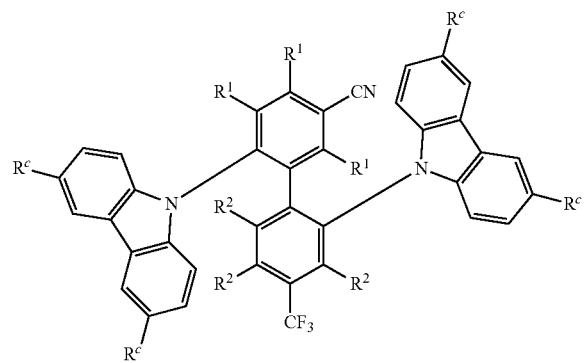

wherein the aforementioned definitions apply.

In a further embodiment of the invention, the organic molecules comprise or consist of a structure selected from the group of Formula IVb:

Formula IVb

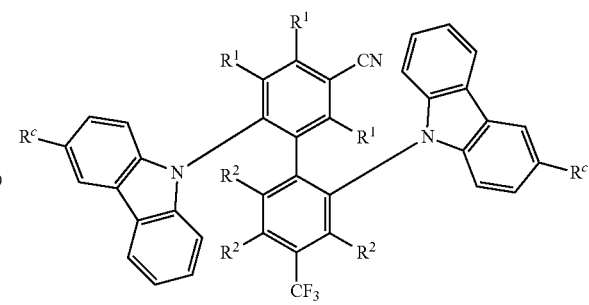

wherein the aforementioned definitions apply.

In a further embodiment of the invention, the organic molecules comprise or consist of a structure selected from the group of Formula IVc:

Formula IVc

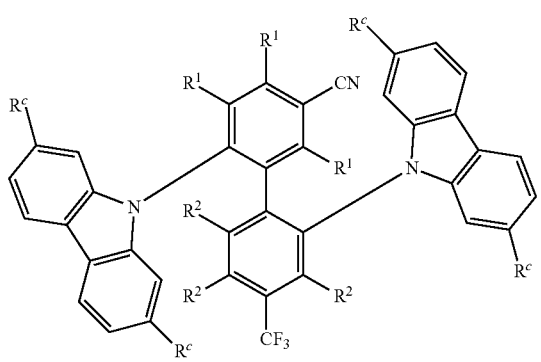

wherein the aforementioned definitions apply.

In a further embodiment of the invention, the organic molecules comprise or consist of a structure selected from the group of Formula IVd:

Formula IVd wherein the aforementioned definitions apply.

In one embodiment of the invention, the organic molecules comprise or consist of a structure of Formula V:

Formula V

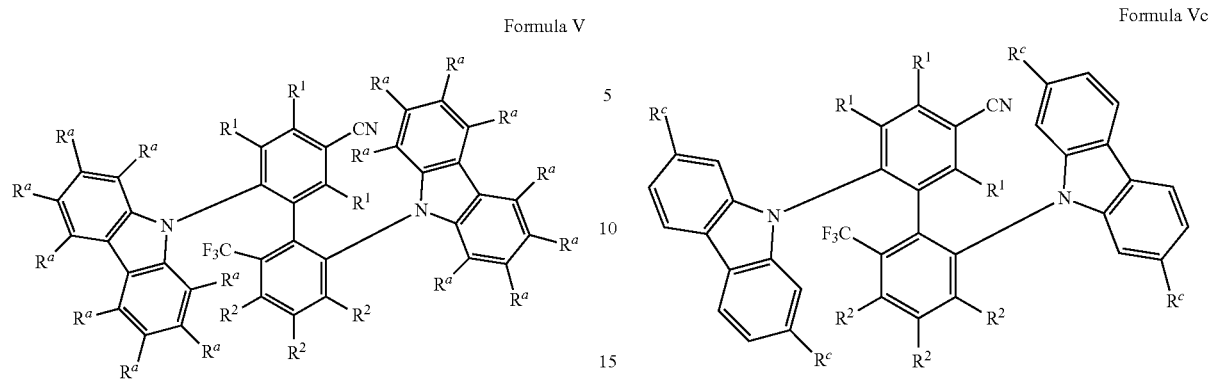

wherein the aforementioned definitions apply.

In a further embodiment of the invention, the organic molecules comprise or consist of a structure selected from the group of Formula Va:

Formula Va

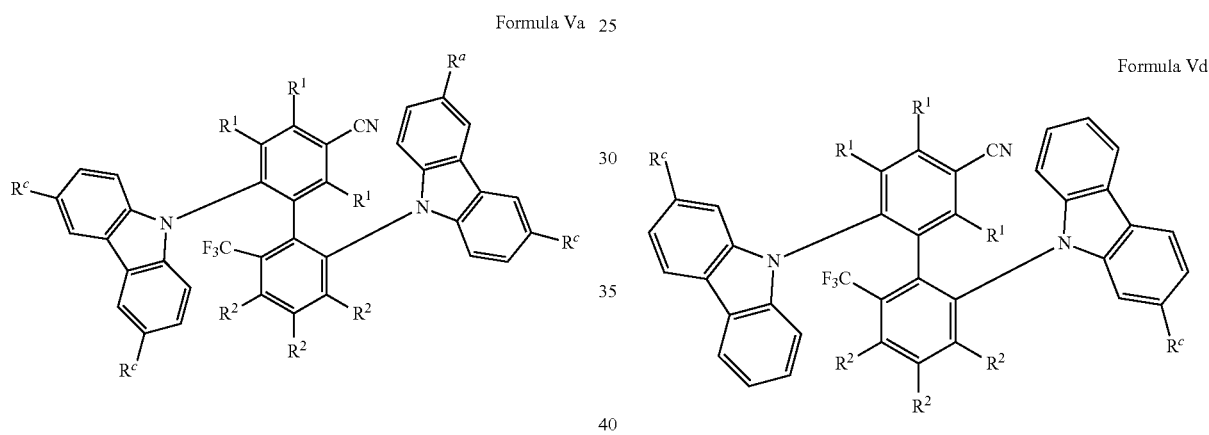

wherein the aforementioned definitions apply.

In a further embodiment of the invention, the organic molecules comprise or consist of a structure selected from the group of Formula Vb:

Formula Vb

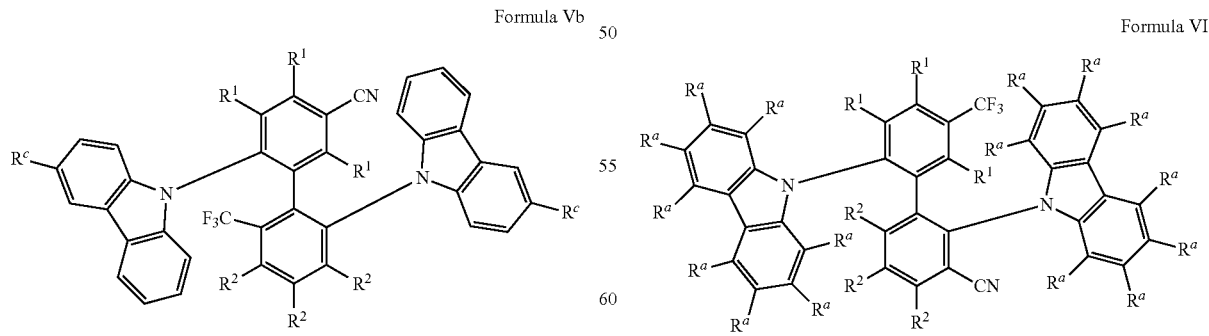

wherein the aforementioned definitions apply.

In a further embodiment of the invention, the organic molecules comprise or consist of a structure selected from the group of Formula Vc:

Formula Vc

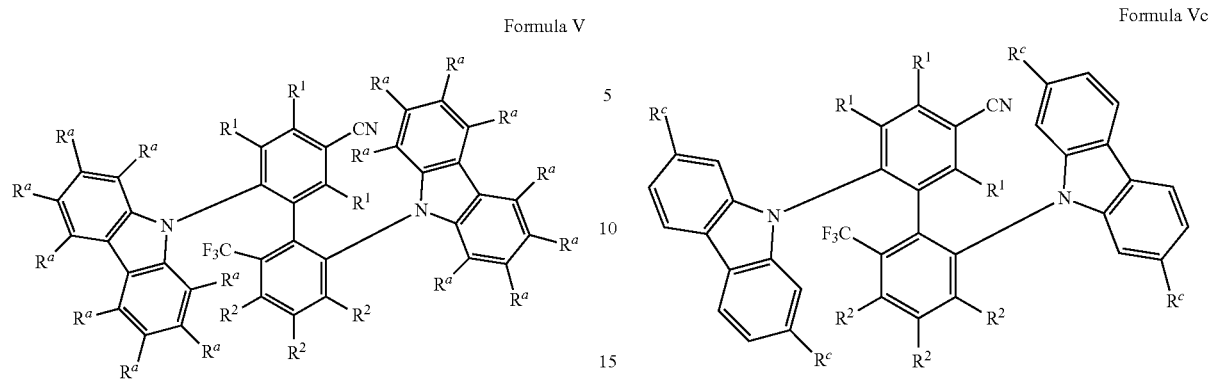

wherein the aforementioned definitions apply.

In a further embodiment of the invention, the organic molecules comprise or consist of a structure selected from the group of Formula Vd:

Formula Vd

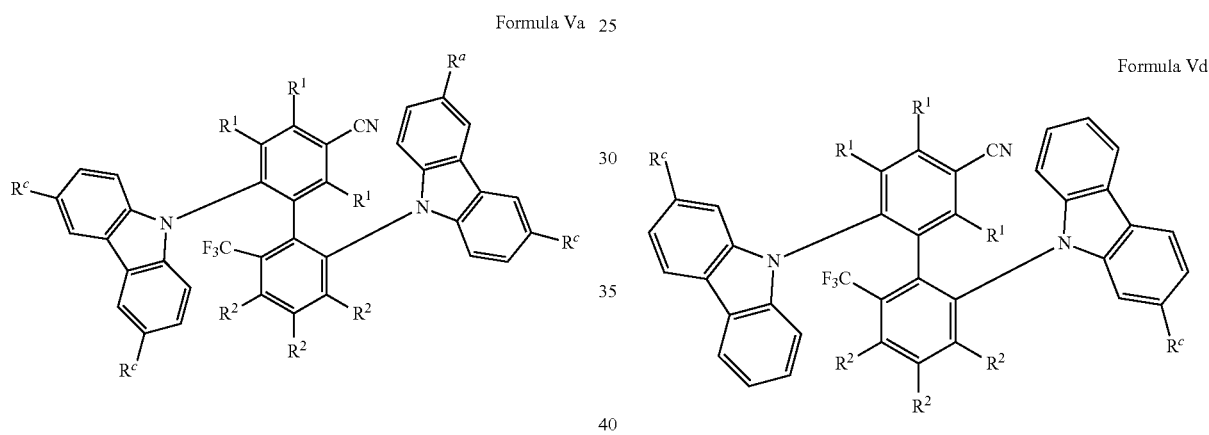

wherein the aforementioned definitions apply.

In one embodiment of the invention, the organic molecules comprise or consist of a structure of Formula VI:

Formula VI

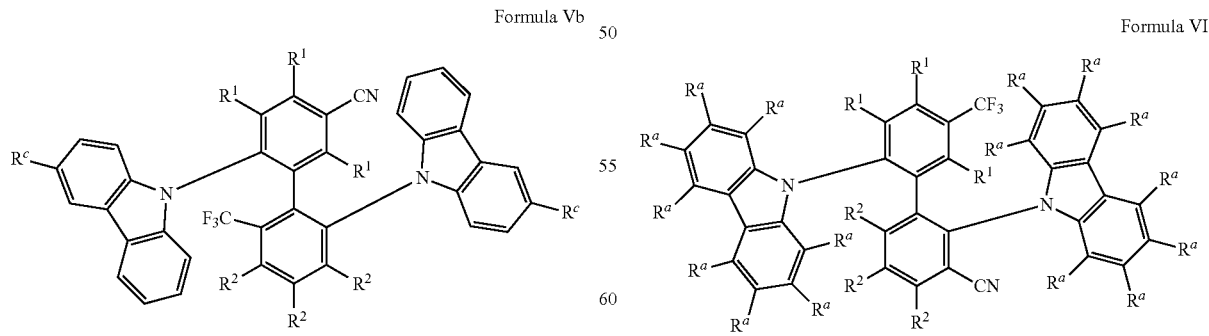

wherein the aforementioned definitions apply.

In a further embodiment of the invention, the organic molecules comprise or consist of a structure selected from the group of Formula VIa:

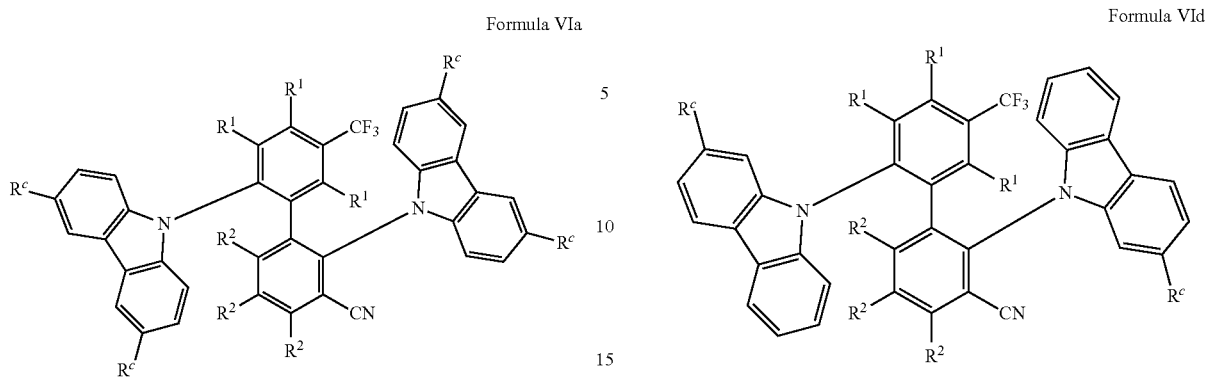

Formula VIa wherein the aforementioned definitions apply.

In a further embodiment of the invention, the organic molecules comprise or consist of a structure selected from the group of Formula VIb:

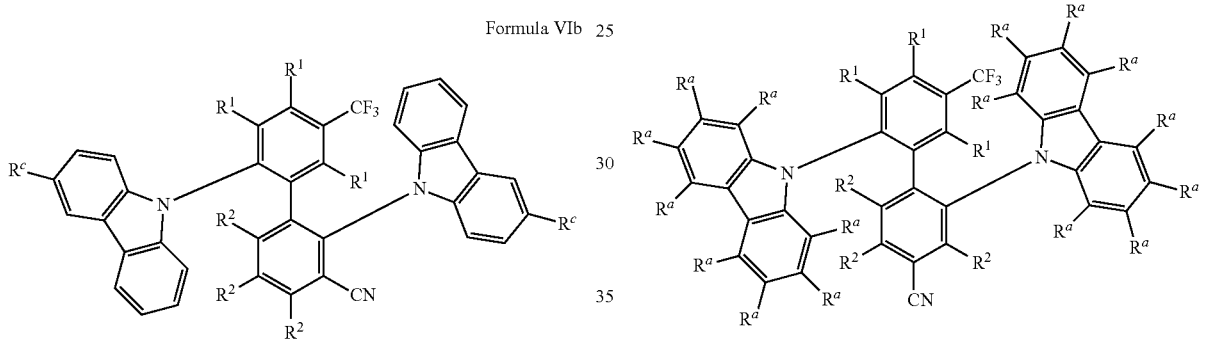

Formula VIb wherein the aforementioned definitions apply.

In a further embodiment of the invention, the organic molecules comprise or consist of a structure selected from the group of Formula VIc:

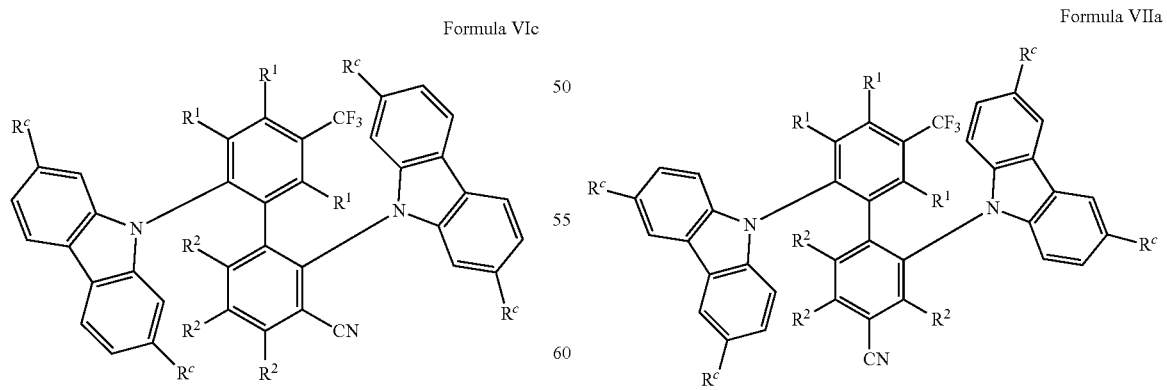

Formula VIc wherein the aforementioned definitions apply.

In a further embodiment of the invention, the organic molecules comprise or consist of a structure selected from the group of Formula VId:

Formula VId wherein the aforementioned definitions apply.

In one embodiment of the invention, the organic molecules comprise or consist of a structure of Formula VII:

Formula VII wherein the aforementioned definitions apply.

In a further embodiment of the invention, the organic molecules comprise or consist of a structure selected from the group of Formula VIIa:

Formula VIIa wherein the aforementioned definitions apply.

In a further embodiment of the invention, the organic molecules comprise or consist of a structure selected from the group of Formula VIIb:

Formula VIIb

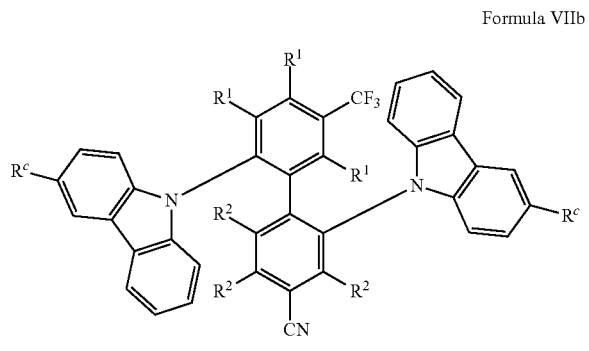

wherein the aforementioned definitions apply.

In a further embodiment of the invention, the organic molecules comprise or consist of a structure selected from the group of Formula VIIc:

Formula VIIc

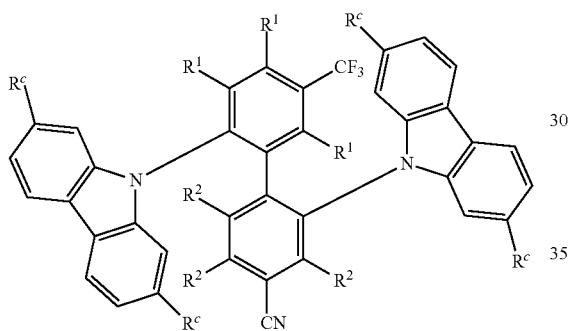

wherein the aforementioned definitions apply.

In a further embodiment of the invention, the organic molecules comprise or consist of a structure selected from the group of Formula VIId:

Formula VIId

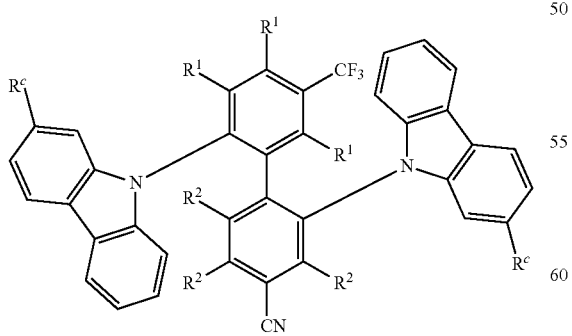

wherein the aforementioned definitions apply.

In one embodiment of the invention, the organic molecules comprise or consist of a structure of Formula VIII:

Formula VIII

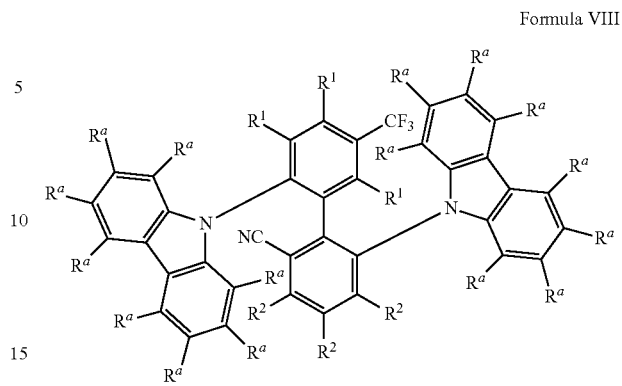

wherein the aforementioned definitions apply.

In a further embodiment of the invention, the organic molecules comprise or consist of a structure selected from the group of Formula VIIIa:

Formula VIIIa

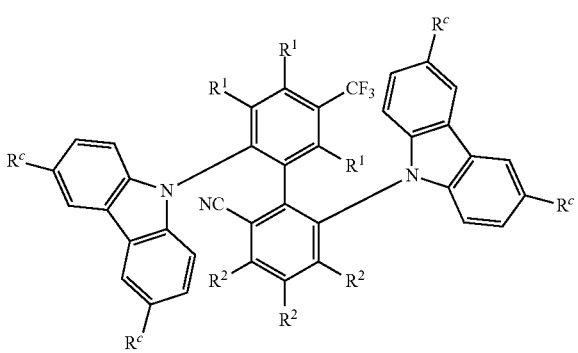

wherein the aforementioned definitions apply.

In a further embodiment of the invention, the organic molecules comprise or consist of a structure selected from the group of Formula VIIb:

Formula VIIIb wherein the aforementioned definitions apply.

In a further embodiment of the invention, the organic molecules comprise or consist of a structure selected from the group of Formula VIIIc:

Formula VIIIc

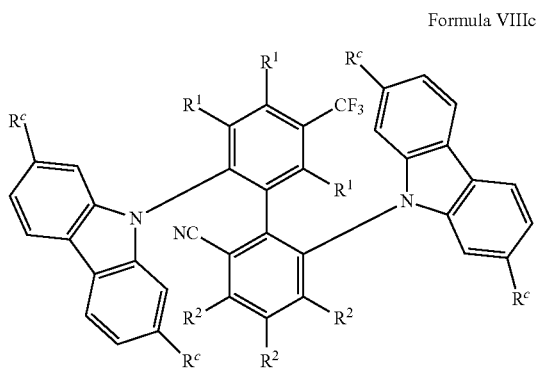

wherein the aforementioned definitions apply.

In a further embodiment of the invention, the organic molecules comprise or consist of a structure selected from the group of Formula VIIId:

Formula VIIId

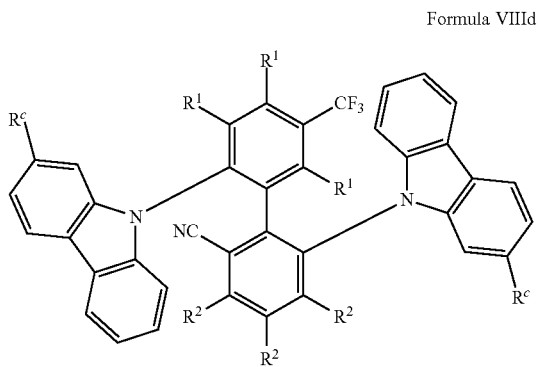

wherein the aforementioned definitions apply.

In one embodiment of the invention $R^c$ is at each occurrence independently from another selected from the group consisting of
Me,
$^iPr$,
$^tBu$,
Ph, which is optionally substituted with one or more substituents independently from each other selected from the group consisting of Me, $^iPr$, $^tBu$, ON, $CF_3$ and Ph; and
triazinyl, which is optionally substituted with one or more substituents independently from each other selected from the group consisting of Me, $^iPr$, $^tBu$, CN, $CF_3$ and Ph.

As used throughout the present application, the terms "aryl" and "aromatic" may be understood in the broadest sense as any mono-, bi- or polycyclic aromatic moieties. Accordingly, an aryl group contains 6 to 60 aromatic ring atoms, and a heteroaryl group contains 5 to 60 aromatic ring atoms, of which at least one is a heteroatom. Notwithstanding, throughout the application the number of aromatic ring atoms may be given as subscripted number in the definition of certain substituents. In particular, the heteroaromatic ring includes one to three heteroatoms. Again, the terms "heteroaryl" and "heteroaromatic" may be understood in the broadest sense as any mono-, bi- or polycyclic heteroaromatic moieties that include at least one heteroatom. The heteroatoms may at each occurrence be the same or different and be individually selected from the group consisting of N, O and S. Accordingly, the term "arylene" refers to a divalent substituent that bears two binding sites to other molecular structures and thereby serving as a linker structure. In case, a group in the exemplary embodiments is defined differently from the definitions given here, for example, the number of aromatic ring atoms or number of heteroatoms differs from the given definition, the definition in the exemplary embodiments is to be applied. According to the invention, a condensed (annulated) aromatic or heteroaromatic polycycle is built of two or more single aromatic or heteroaromatic cycles, which formed the polycycle via a condensation reaction.

In particular, as used throughout the present application the term aryl group or heteroaryl group comprises groups which can be bound via any position of the aromatic or heteroaromatic group, derived from benzene, naphthaline, anthracene, phenanthrene, pyrene, dihydropyrene, chrysene, perylene, fluoranthene, benzanthracene, benzphenanthrene, tetracene, pentacene, benzpyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthoimidazole, phenanthroimidazole, pyridoimidazole, pyrazinoimidazole, quinoxalinoimidazole, oxazole, benzoxazole, napthooxazole, anthroxazol, phenanthroxazol, isoxazole, 1,2-thiazole, 1,3-thiazole, benzothiazole, pyridazine, benzopyridazine, pyrimidine, benzopyrimidine, 1,3,5-triazine, quinoxaline, pyrazine, phenazine, naphthyridine, carboline, benzocarboline, phenanthroline, 1,2,3-triazole, 1,2,4-triazole, benzotriazole, 1,2,3-oxadiazole, 1,2,4-oxadiazole, 1,2, 5-oxadiazole, 1,2,3,4-tetrazine, purine, pteridine, indolizine and benzothiadiazole or combinations of the abovementioned groups.

As used throughout the present application the term cyclic group may be understood in the broadest sense as any mono-, bi- or polycyclic moieties.

As used throughout the present application the term biphenyl as a substituent may be understood in the broadest sense as ortho-biphenyl, meta-biphenyl, or para-biphenyl, wherein ortho, meta and para is defined in regard to the binding site to another chemical moiety.

As used throughout the present application the term alkyl group may be understood in the broadest sense as any linear, branched, or cyclic alkyl substituent. In particular, the term alkyl comprises the substituents methyl (Me), ethyl (Et), n-propyl ($^nPr$), i-propyl ($^iPr$), cyclopropyl, n-butyl ($^nBu$), i-butyl ($^iBu$), s-butyl ($^sBu$), t-butyl ($^tBu$), cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neo-hexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2,2,2]octyl, 2-bicyclo[2,2,2]-octyl, 2-(2,6-dimethyl)octyl, 3-(3,7-dimethyl)octyl, adamantyl, 2,2,2-trifluorethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyln-n-hexadec-1-yl, 1,1-diethyl-n-octadec-1-yl, 1-(n-propyl)-cyclohex-1-yl, 1-(n-butyl)-cyclohex-1-yl, 1-(n-hexyl)-cyclohex-1-yl, 1-(n-octyl)-cyclohex-1-yl and 1-(n-decyl)-cyclohex-1-yl.

As used throughout the present application the term alkenyl comprises linear, branched, and cyclic alkenyl substituents. The term alkenyl group exemplarily comprises the substituents ethenyl, propenyl, butenyl, pentenyl, cyclopentenyl, hexenyl, cyclohexenyl, heptenyl, cycloheptenyl, octenyl, cyclooctenyl or cyclooctadienyl.

As used throughout the present application the term alkynyl comprises linear, branched, and cyclic alkynyl substituents. The term alkynyl group exemplarily comprises ethynyl, propynyl, butynyl, pentynyl, hexynyl, heptynyl or octynyl.

As used throughout the present application the term alkoxy comprises linear, branched, and cyclic alkoxy substituents. The term alkoxy group exemplarily comprises methoxy, ethoxy, n-propoxy, i-propoxy, n-butoxy, i-butoxy, s-butoxy, t-butoxy and 2-methylbutoxy.

As used throughout the present application the term thioalkoxy comprises linear, branched, and cyclic thioalkoxy substituents, in which the O of the exemplarily alkoxy groups is replaced by S.

As used throughout the present application, the terms "halogen" and "halo" may be understood in the broadest sense as being preferably fluorine, chlorine, bromine or iodine.

Whenever hydrogen (H) is mentioned herein, it could also be replaced by deuterium at each occurrence.

It is understood that when a molecular fragment is described as being a substituent or otherwise attached to another moiety, its name may be written as if it were a fragment (e.g. naphtyl, dibenzofuryl) or as if it were the whole molecule (e.g. naphthalene, dibenzofuran). As used herein, these different ways of designating a substituent or attached fragment are considered to be equivalent.

In one embodiment, the organic molecules according to the invention have an excited state lifetime of not more than 150 μs, of not more than 100 μs, in particular of not more than 50 μs, more preferably of not more than 10 μs or not more than 7 μs in a film of poly(methyl methacrylate) (PMMA) with 10% by weight of organic molecule at room temperature.

In one embodiment of the invention, the organic molecules according to the invention represent thermally-activated delayed fluorescence (TADF) emitters, which exhibit a $\Delta E_{ST}$ value, which corresponds to the energy difference between the first excited singlet state (S1) and the first excited triplet state (T1), of less than 5000 cm$^{-1}$, preferably less than 3000 cm$^{-1}$, more preferably less than 1500 cm$^{-1}$, even more preferably less than 1000 cm$^{-1}$ or even less than 500 cm$^{-1}$.

In a further embodiment of the invention, the organic molecules according to the invention have an emission peak in the visible or nearest ultraviolet range, i.e., in the range of a wavelength of from 380 to 800 nm, with a full width at half maximum of less than 0.50 eV, preferably less than 0.48 eV, more preferably less than 0.45 eV, even more preferably less than 0.43 eV or even less than 0.40 eV in a film of poly(methyl methacrylate) (PMMA) with 10% by weight of organic molecule at room temperature.

In a further embodiment of the invention, the organic molecules according to the invention have a "blue material index" (BMI), calculated by dividing the photoluminescence quantum yield (PLQY) in % by the CIEy color coordinate of the emitted light, of more than 150, in particular more than 200, preferably more than 250, more preferably of more than 300 or even more than 500.

Orbital and excited state energies can be determined either by means of experimental methods or by calculations employing quantum-chemical methods, in particular density functional theory calculations. The energy of the highest occupied molecular orbital $E^{HOMO}$ is determined by methods known to the person skilled in the art from cyclic voltammetry measurements with an accuracy of 0.1 eV. The energy of the lowest unoccupied molecular orbital $E^{LUMO}$ is determined as the onset of the absorption spectrum.

The onset of an absorption spectrum is determined by computing the intersection of the tangent to the absorption spectrum with the x-axis. The tangent to the absorption spectrum is set at the low-energy side of the absorption band and at the point at half maximum of the maximum intensity of the absorption spectrum.

The energy of the first excited triplet state T1 is determined from the onset of the emission spectrum at low temperature, typically at 77 K. For host compounds, where the first excited singlet state and the lowest triplet state are energetically separated by >0.4 eV, the phosphorescence is usually visible in a steady-state spectrum in 2-Me-THF. The triplet energy can thus be determined as the onset of the phosphorescence spectrum. For TADF emitter molecules, the energy of the first excited triplet state T1 is determined from the onset of the delayed emission spectrum at 77 K, if not otherwise stated measured in a film of PMMA with 10% by weight of emitter. Both for host and emitter compounds, the energy of the first excited singlet state S1 is determined from the onset of the emission spectrum, if not otherwise stated measured in a film of PMMA with 10% by weight of host or emitter compound.

The onset of an emission spectrum is determined by computing the intersection of the tangent to the emission spectrum with the x-axis. The tangent to the emission spectrum is set at the high-energy side of the emission band and at the point at half maximum of the maximum intensity of the emission spectrum.

A further aspect of the invention relates to a process for preparing organic molecules (with an optional subsequent reaction) according to the invention, wherein a R$^2$-substituted, cyano/trifluoromethyl-substituted 1-bromo-2-fluorophenyl is used as a reactant:

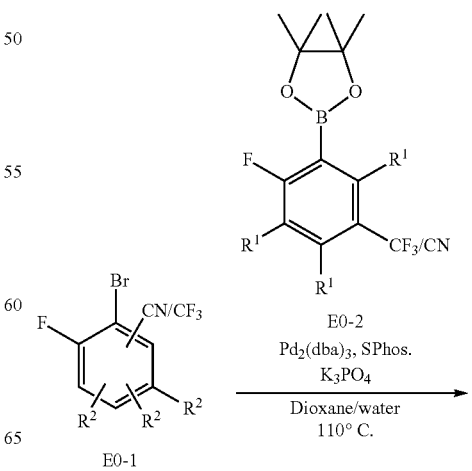

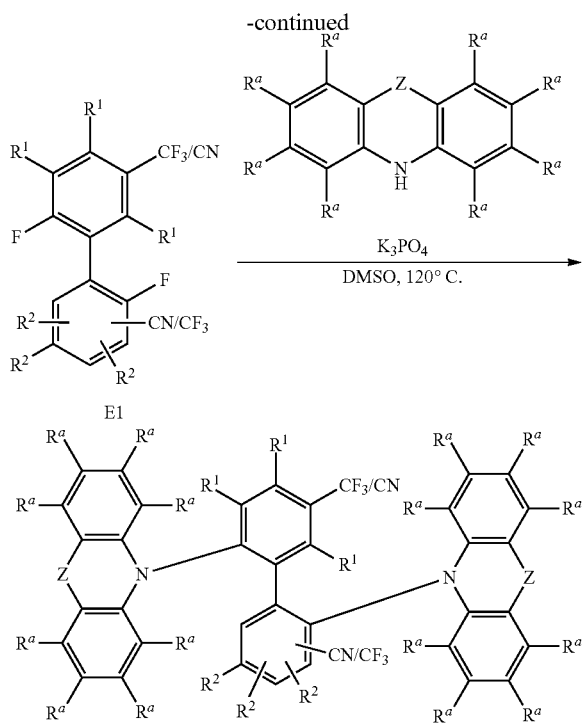

According to the invention, in the reaction for the synthesis of E1 a boronic acid or an equivalent boronic acid ester can be used instead of a boronic pinacol ester.

Typically, $Pd_2(dba)_3$ (tris(dibenzylideneacetone)dipalladium(0)) is used as a Pd catalyst, but alternatives are known in the art. For example, the ligand may be selected from the group consisting of S-Phos ([2-dicyclohexylphoshino-2',6'-dimethoxy-1,1'-biphenyl]; or SPhos), X-Phos (2-(dicyclohexylphosphino)-2",4", 6"-triisopropylbiphenyl; or XPhos), and $P(Cy)_3$ (tricyclohexylphosphine). The salt is, for example, selected from tribasic potassium phosphate and potassium acetate and the solvent can be a pure solvent, such as toluene or dioxane, or a mixture, such as toluene/dioxane/water or dioxane/toluene. A person of skill in the art can determine which Pd catalyst, ligand, salt and solvent combination will result in high reaction yields.

For the reaction of a nitrogen heterocycle in a nucleophilic aromatic substitution with an aryl halide, preferably an aryl fluoride, typical conditions include the use of a base, such as tribasic potassium phosphate or sodium hydride, for example, in an aprotic polar solvent, such as dimethyl sulfoxide (DMSO) or N,N-dimethylformamide (DMF), for example.

An alternative synthesis route comprises the introduction of a nitrogen heterocycle via copper- or palladium-catalyzed coupling to an aryl halide or aryl pseudohalide, preferably an aryl bromide, an aryl iodide, aryl triflate or an aryl tosylate.

A further aspect of the invention relates to the use of an organic molecule according to the invention as a luminescent emitter or as an absorber, and/or as host material and/or as electron transport material, and/or as hole injection material, and/or as hole blocking material in an organic optoelectronic device.

The organic electroluminescent device may be understood in the broadest sense as any device based on organic materials that is suitable for emitting light in the visible or nearest ultraviolet (UV) range, i.e., in the range of a wavelength of from 380 to 800 nm. More preferably, organic electroluminescent device may be able to emit light in the visible range, i.e., of from 400 to 800 nm.

In the context of such use, the optoelectronic device is more particularly selected from the group consisting of:
 organic light-emitting diodes (OLEDs),
 light-emitting electrochemical cells,
 OLED sensors, especially in gas and vapour sensors not hermetically externally shielded,
 organic diodes,
 organic solar cells,
 organic transistors,
 organic field-effect transistors,
 organic lasers and
 down-conversion elements.

In a preferred embodiment in the context of such use, the organic electroluminescent device is a device selected from the group consisting of an organic light emitting diode (OLED), a light emitting electrochemical cell (LEC), and a light-emitting transistor.

In the case of the use, the fraction of the organic molecule according to the invention in the emission layer in an organic optoelectronic device, more particularly in OLEDs, is 1% to 99% by weight, more particularly 5% to 80% by weight. In an alternative embodiment, the proportion of the organic molecule in the emission layer is 100% by weight.

In one embodiment, the light-emitting layer comprises not only the organic molecules according to the invention but also a host material whose triplet (T1) and singlet (S1) energy levels are energetically higher than the triplet (T1) and singlet (S1) energy levels of the organic molecule.

A further aspect of the invention relates to a composition comprising or consisting of:
(a) at least one organic molecule according to the invention, in particular in the form of an emitter and/or a host, and
(b) one or more emitter and/or host materials, which differ from the organic molecule according to the invention and
(c) optional one or more dyes and/or one or more solvents.

In one embodiment, the light-emitting layer comprises (or (essentially) consists of) a composition comprising or consisting of:
(a) at least one organic molecule according to the invention, in particular in the form of an emitter and/or a host, and
(b) one or more emitter and/or host materials, which differ from the organic molecule according to the invention and
(c) optional one or more dyes and/or one or more solvents.

Particularly preferably the light-emitting layer EML comprises (or (essentially) consists of) a composition comprising or consisting of:
(i) 1-50% by weight, preferably 5-40% by weight, in particular 10-30% by weight, of one or more organic molecules according to the invention E;
(ii) 5-99% by weight, preferably 30-94.9% by weight, in particular 40-89% by weight, of at least one host compound H; and
(iii) optionally 0-94% by weight, preferably 0.1-65% by weight, in particular 1-50% by weight, of at least one further host compound D with a structure differing from the structure of the molecules according to the invention; and
(iv) optionally 0-94% by weight, preferably 0-65% by weight, in particular 0-50% by weight, of a solvent; and
(v) optionally 0-30% by weight, in particular 0-20% by weight, preferably 0-5% by weight, of at least one further emitter molecule F with a structure differing from the structure of the molecules according to the invention.

Preferably, energy can be transferred from the host compound H to the one or more organic molecules according to the invention E, in particular transferred from the first excited triplet state T1(H) of the host compound H to the first excited triplet state T1(E) of the one or more organic molecules according to the invention E and/or from the first excited singlet state S1(H) of the host compound H to the first excited singlet state S1(E) of the one or more organic molecules according to the invention E.

In a further embodiment, the light-emitting layer EML comprises (or (essentially) consists of) a composition comprising or consisting of:
(i) 1-50% by weight, preferably 5-40% by weight, in particular 10-30% by weight, of one organic molecule according to the invention E;
(ii) 5-99% by weight, preferably 30-94.9% by weight, in particular 40-89% by weight, of one host compound H; and
(iii) optionally 0-94% by weight, preferably 0.1-65% by weight, in particular 1-50% by weight, of at least one further host compound D with a structure differing from the structure of the molecules according to the invention; and
(iv) optionally 0-94% by weight, preferably 0-65% by weight, in particular 0-50% by weight, of a solvent; and
(v) optionally 0-30% by weight, in particular 0-20% by weight, preferably 0-5% by weight, of at least one further emitter molecule F with a structure differing from the structure of the molecules according to the invention.

In one embodiment, the host compound H has a highest occupied molecular orbital HOMO(H) having an energy $E^{HOMO}(H)$ in the range of from −5 to −6.5 eV and the at least one further host compound D has a highest occupied molecular orbital HOMO(D) having an energy $E^{HOMO}(D)$, wherein $E^{HOMO}(H)>E^{HOMO}(D)$.

In a further embodiment, the host compound H has a lowest unoccupied molecular orbital LUMO(H) having an energy $E^{LUMO}(H)$ and the at least one further host compound D has a lowest unoccupied molecular orbital LUMO(D) having an energy $E^{LUMO}(D)$, wherein $E^{LUMO}(H)>E^{LUMO}(D)$.

In one embodiment, the host compound H has a highest occupied molecular orbital HOMO(H) having an energy $E^{HOMO}(H)$ and a lowest unoccupied molecular orbital LUMO(H) having an energy $E^{LUMO}(H)$, and
the at least one further host compound D has a highest occupied molecular orbital HOMO(D) having an energy $E^{HOMO}(D)$ and a lowest unoccupied molecular orbital LUMO(D) having an energy $E^{LUMO}(D)$,
the organic molecule according to the invention E has a highest occupied molecular orbital HOMO(E) having an energy $E^{HOMO}(E)$ and a lowest unoccupied molecular orbital LUMO(E) having an energy $E^{LUMO}(E)$,
wherein
$E^{HOMO}(H)>E^{HOMO}(D)$ and the difference between the energy level of the highest occupied molecular orbital HOMO(E) of the organic molecule according to the invention E ($E^{HOMO}(E)$) and the energy level of the highest occupied molecular orbital HOMO(H) of the host compound H ($E^{HOMO}(H)$) is between −0.5 eV and 0.5 eV, more preferably between −0.3 eV and 0.3 eV, even more preferably between −0.2 eV and 0.2 eV or even between −0.1 eV and 0.1 eV; and $E^{LUMO}(H)>E^{LUMO}(D)$ and the difference between the energy level of the lowest unoccupied molecular orbital LUMO(E) of the organic molecule according to the invention E ($E^{LUMO}(E)$) and the lowest unoccupied molecular orbital LUMO(D) of the at least one further host compound D ($E^{LUMO}(D)$) is between −0.5 eV and 0.5 eV, more preferably between −0.3 eV and 0.3 eV, even more preferably between −0.2 eV and 0.2 eV or even between −0.1 eV and 0.1 eV.

In a further aspect, the invention relates to an optoelectronic device comprising an organic molecule or a composition of the type described here, more particularly in the form of a device selected from the group consisting of organic light-emitting diode (OLED), light-emitting electrochemical cell, OLED sensor, more particularly gas and vapour sensors not hermetically externally shielded, organic diode, organic solar cell, organic transistor, organic field-effect transistor, organic laser and down-conversion element.

In a preferred embodiment, the organic electroluminescent device is a device selected from the group consisting of an organic light emitting diode (OLED), a light emitting electrochemical cell (LEC), and a light-emitting transistor.

In one embodiment of the optoelectronic device of the invention, the organic molecule according to the invention E is used as emission material in a light-emitting layer EML.

In one embodiment of the optoelectronic device of the invention the light-emitting layer EML consists of the composition according to the invention described here.

Exemplarily, when the organic electroluminescent device is an OLED, it may exhibit the following layer structure:
1. substrate
2. anode layer A
3. hole injection layer, HIL
4. hole transport layer, HTL
5. electron blocking layer, EBL
6. emitting layer, EML
7. hole blocking layer, HBL
8. electron transport layer, ETL
9. electron injection layer, EIL
10. cathode layer, wherein the OLED comprises each layer only optionally, different layers may be merged and the OLED may comprise more than one layer of each layer type defined above.

Furthermore, the organic electroluminescent device may optionally comprise one or more protective layers protecting the device from damaging exposure to harmful species in the environment including, exemplarily moisture, vapor and/or gases.

In one embodiment of the invention, the organic electroluminescent device is an OLED, which exhibits the following inverted layer structure:
1. substrate
2. cathode layer
3. electron injection layer, EIL
4. electron transport layer, ETL
5. hole blocking layer, HBL
6. emitting layer, B
7. electron blocking layer, EBL
8. hole transport layer, HTL
9. hole injection layer, HIL
10. anode layer A Wherein the OLED with an inverted layer structure comprises each layer only optionally, different layers may be merged and the OLED may comprise more than one layer of each layer types defined above.

In one embodiment of the invention, the organic electroluminescent device is an OLED, which may exhibit stacked architecture. In this architecture, contrary to the typical arrangement, where the OLEDs are placed side by side, the individual units are stacked on top of each other. Blended light may be generated with OLEDs exhibiting a stacked architecture, in particular white light may be generated by stacking blue, green and red OLEDs. Furthermore, the OLED exhibiting a stacked architecture may optionally comprise a charge generation layer (CGL), which is typically located between two OLED subunits and typically consists of a n-doped and p-doped layer with the n-doped layer of one CGL being typically located closer to the anode layer.

In one embodiment of the invention, the organic electroluminescent device is an OLED, which comprises two or more emission layers between anode and cathode. In particular, this so-called tandem OLED comprises three emission layers, wherein one emission layer emits red light, one emission layer emits green light and one emission layer emits blue light, and optionally may comprise further layers such as charge generation layers, blocking or transporting layers between the individual emission layers. In a further embodiment, the emission layers are adjacently stacked. In a further embodiment, the tandem OLED comprises a charge generation layer between each two emission layers. In addition, adjacent emission layers or emission layers separated by a charge generation layer may be merged.

The substrate may be formed by any material or composition of materials. Most frequently, glass slides are used as substrates. Alternatively, thin metal layers (e.g., copper, gold, silver or aluminum films) or plastic films or slides may be used. This may allow a higher degree of flexibility. The anode layer A is mostly composed of materials allowing to obtain an (essentially) transparent film. As at least one of both electrodes should be (essentially) transparent in order to allow light emission from the OLED, either the anode layer A or the cathode layer C is transparent.

Preferably, the anode layer A comprises a large content or even consists of transparent conductive oxides (TCOs). Such anode layer A may exemplarily comprise indium tin oxide, aluminum zinc oxide, fluorine doped tin oxide, indium zinc oxide, PbO, SnO, zirconium oxide, molybdenum oxide, vanadium oxide, wolfram oxide, graphite, doped Si, doped Ge, doped GaAs, doped polyaniline, doped polypyrrol and/or doped polythiophene.

Particularly preferably, the anode layer A (essentially) consists of indium tin oxide (ITO) (e.g., $(InO_3)0.9(SnO_2)0.1$). The roughness of the anode layer A caused by the transparent conductive oxides (TCOs) may be compensated by using a hole injection layer (HIL). Further, the HIL may facilitate the injection of quasi charge carriers (i.e., holes) in that the transport of the quasi charge carriers from the TCO to the hole transport layer (HTL) is facilitated. The hole injection layer (HIL) may comprise poly-3,4-ethylendioxy thiophene (PEDOT), polystyrene sulfonate (PSS), $MoO_2$, $V_2O_5$, CuPC or CuI, in particular a mixture of PEDOT and PSS. The hole injection layer (HIL) may also prevent the diffusion of metals from the anode layer A into the hole transport layer (HTL). The HIL may exemplarily comprise PEDOT:PSS (poly-3,4-ethylendioxy thiophene: polystyrene sulfonate), PEDOT (poly-3,4-ethylendioxy thiophene), mMTDATA (4,4',4"-tris[phenyl(m-tolyl)amino]triphenylamine), Spiro-TAD (2,2',7,7'-tetrakis(n,n-diphenylamino)-9,9'-spirobifluorene), DNTPD (N1,N1'-(biphenyl-4,4'-diyl)bis(N1-phenyl-N4,N4-di-m-tolylbenzene-1,4-diamine), NPB (N,N'-nis-(1-naphthalenyl)-N,N'-bis-phenyl-(1,1'-biphenyl)-4,4'-diamine), NPNPB (N,N'-diphenyl-N,N'-di-[4-(N, N-diphenyl-amino)phenyl]benzidine), MeO-TPD (N,N,N',N'-tetrakis(4-methoxyphenyl)benzidine), HAT-CN (1,4,5,8,9,11-hexaazatriphenylen-hexacarbonitrile) and/or Spiro-NPD (N,N'-diphenyl-N,N'-bis-(1-naphthyl)-9,9'-spirobifluorene-2,7-diamine).

Adjacent to the anode layer A or hole injection layer (HIL) typically a hole transport layer (HTL) is located. Herein, any hole transport compound may be used. Exemplarily, electron-rich heteroaromatic compounds such as triarylamines and/or carbazoles may be used as hole transport compound. The HTL may decrease the energy barrier between the anode layer A and the light-emitting layer EML. The hole transport layer (HTL) may also be an electron blocking layer (EBL). Preferably, hole transport compounds bear comparably high energy levels of their triplet states T1. Exemplarily the hole transport layer (HTL) may comprise a star-shaped heterocycle such as tris(4-carbazoyl-9-ylphenyl)amine (TCTA), poly-TPD (poly(4-butylphenyl-diphenyl-amine)), [alpha]-NPD (poly(4-butylphenyl-diphenyl-amine)), TAPC (4,4'-cyclohexyliden-bis[N,N-bis(4-methylphenyl)benzenamine]), 2-TNATA (4,4',4"-tris[2-naphthyl(phenyl)amino] triphenylamine), Spiro-TAD, DNTPD, NPB, NPNPB, MeO-TPD, HAT-CN and/or TrisPcz (9,9'-diphenyl-6-(9-phenyl-9H-carbazol-3-yl)-9H,9'H-3,3'-bicarbazole). In addition, the HTL may comprise a p-doped layer, which may be composed of an inorganic or organic dopant in an organic hole-transporting matrix. Transition metal oxides such as vanadium oxide, molybdenum oxide or tungsten oxide may exemplarily be used as inorganic dopant. Tetrafluorotetracyanoquinodimethane ($F_4$-TCNQ), copper-pentafluorobenzoate (Cu(I)pFBz) or transition metal complexes may exemplarily be used as organic dopant.

The EBL may exemplarily comprise mCP (1,3-bis(carbazol-9-yl)benzene), TCTA, 2-TNATA, mCBP (3,3-di(9H-carbazol-9-yl) biphenyl), tris-Pcz, CzSi (9-(4-tert-Butylphenyl)-3,6-bis(triphenylsilyl)-9H-carbazole), and/or DCB (N,N'-dicarbazolyl-1,4-dimethyl benzene).

Adjacent to the hole transport layer (HTL), typically, the light-emitting layer EML is located. The light-emitting layer EML comprises at least one light emitting molecule. Particularly, the EML comprises at least one light emitting molecule according to the invention E. In one embodiment, the light-emitting layer comprises only the organic molecules according to the invention E. Typically, the EML additionally comprises one or more host materials H. Exemplarily, the host material H is selected from CBP (4,4'-Bis-(N-carbazolyl)-biphenyl), mCP, mCBP Sif87 (dibenzo[b,d]thiophen-2-yltriphenylsilane), CzSi, SimCP ([3,5-Di(9H-carbazol-9-yl)phenyl]triphenylsilane), Sif88 (dibenzo[b,d]thiophen-2-yl)diphenylsilane), DPEPO (bis[2-(diphenylphosphino)phenyl] ether oxide), 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole, 9-[3,5-bis(2-dibenzothiophenyl)phenyl]-9H-carbazole, T2T (2,4,6-tris(biphenyl-3-yl)-1,3,5-triazine), T3T (2,4,6-tris(triphenyl-3-yl)-1,3,5-triazine) and/or TST (2,4,6-tris(9,9'-spirobifluorene-2-yl)-1,3,5-triazine). The host material H typically should be selected to exhibit first triplet (T1) and first singlet (S1) energy levels, which are energetically higher than the first triplet (T1) and first singlet (S1) energy levels of the organic molecule.

In one embodiment of the invention, the EML comprises a so-called mixed-host system with at least one hole-dominant host and one electron-dominant host. In a particular embodiment, the EML comprises exactly one light emitting molecule according to the invention E and a mixed-host system comprising T2T as electron-dominant host and a host selected from CBP, mCP, mCBP, 9-[3-(dibenzofuran-2-yl) phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole as hole-dominant host. In a further embodiment the EML comprises 50-80% by weight, preferably 60-75% by weight of a host selected from CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole; 10-45% by weight, preferably 15-30% by weight of T2T and 5-40% by weight, preferably 10-30% by weight of light emitting molecule according to the invention.

Adjacent to the light-emitting layer EML an electron transport layer (ETL) may be located. Herein, any electron transporter may be used. Exemplarily, electron-poor compounds such as, e.g., benzimidazoles, pyridines, triazoles, oxadiazoles (e.g., 1,3,4-oxadiazole), phosphinoxides and sulfone, may be used. An electron transporter may also be a star-shaped heterocycle such as 1,3,5-tri(1-phenyl-1H-benzo[d]imidazol-2-yl)phenyl (TPBi). The ETL may comprise NBphen (2,9-bis(naphthalen-2-yl)-4,7-diphenyl-1,10-phenanthroline), Alq$_3$ (Aluminum-tris(8-hydroxyquinoline)), TSPO1 (diphenyl-4-triphenylsilylphenyl-phosphinoxide), BPyTP2 (2,7-di(2,2'-bipyridin-5-yl)triphenyle), Sif87 (dibenzo[b,d]thiophen-2-yltriphenylsilane), Sif88 (dibenzo[b,d]thiophen-2-yl)diphenylsilane), BmPyPhB (1,3-bis[3,5-di(pyridin-3-yl)phenyl]benzene) and/or BTB (4,4'-bis-[2-(4,6-diphenyl-1,3,5-triazinyl)]-1,1'-biphenyl). Optionally, the ETL may be doped with materials such as Liq. The electron transport layer (ETL) may also block holes or a holeblocking layer (HBL) is introduced.

The HBL may exemplarily comprise BCP (2,9-dimethyl-4,7-diphenyl-1,10-phenanthroline=Bathocuproine), BAlq (bis(8-hydroxy-2-methylquinoline)-(4-phenylphenoxy)aluminum), NBphen (2,9-bis(naphthalen-2-yl)-4,7-diphenyl-1,10-phenanthroline), Alq$_3$ (Aluminum-tris(8-hydroxyquinoline)), TSPO1 (diphenyl-4-triphenylsilylphenyl-phosphinoxide), T2T (2,4,6-tris(biphenyl-3-yl)-1,3,5-triazine), T3T (2,4,6-tris(triphenyl-3-yl)-1,3,5-triazine), TST (2,4,6-tris(9,9'-spirobifluorene-2-yl)-1,3,5-triazine), and/or TCB/TCP (1,3,5-tris(N-carbazolyl)benzol/1,3,5-tris(carbazol)-9-yl) benzene).

Adjacent to the electron transport layer (ETL), a cathode layer C may be located. Exemplarily, the cathode layer C may comprise or may consist of a metal (e.g., Al, Au, Ag, Pt, Cu, Zn, Ni, Fe, Pb, LiF, Ca, Ba, Mg, In, W, or Pd) or a metal alloy. For practical reasons, the cathode layer may also consist of (essentially) non-transparent metals such as Mg, Ca or Al. Alternatively or additionally, the cathode layer C may also comprise graphite and or carbon nanotubes (CNTs). Alternatively, the cathode layer C may also consist of nanoscalic silver wires.

An OLED may further, optionally, comprise a protection layer between the electron transport layer (ETL) and the cathode layer C (which may be designated as electron injection layer (EIL)). This layer may comprise lithium fluoride, cesium fluoride, silver, Liq (8-hydroxyquinolinolatolithium), Li$_2$O, BaF$_2$, MgO and/or NaF.

Optionally, also the electron transport layer (ETL) and/or a hole blocking layer (HBL) may comprise one or more host compounds H.

In order to modify the emission spectrum and/or the absorption spectrum of the light-emitting layer EML further, the light-emitting layer EML may further comprise one or more further emitter molecules F. Such an emitter molecule F may be any emitter molecule known in the art. Preferably such an emitter molecule F is a molecule with a structure differing from the structure of the molecules according to the invention E. The emitter molecule F may optionally be a TADF emitter. Alternatively, the emitter molecule F may optionally be a fluorescent and/or phosphorescent emitter molecule which is able to shift the emission spectrum and/or the absorption spectrum of the light-emitting layer EML. Exemplarily, the triplet and/or singlet excitons may be transferred from the emitter molecule according to the invention E to the emitter molecule F before relaxing to the ground state S0 by emitting light typically red-shifted in comparison to the light emitted by emitter molecule E. Optionally, the emitter molecule F may also provoke two-photon effects (i.e., the absorption of two photons of half the energy of the absorption maximum).

Optionally, an organic electroluminescent device (e.g., an OLED) may exemplarily be an essentially white organic electroluminescent device. Exemplarily such white organic electroluminescent device may comprise at least one (deep) blue emitter molecule and one or more emitter molecules emitting green and/or red light. Then, there may also optionally be energy transmittance between two or more molecules as described above.

As used herein, if not defined more specifically in the particular context, the designation of the colors of emitted and/or absorbed light is as follows:
violet: wavelength range of >380-420 nm;
deep blue: wavelength range of >420-480 nm;
sky blue: wavelength range of >480-500 nm;
green: wavelength range of >500-560 nm;
yellow: wavelength range of >560-580 nm;
orange: wavelength range of >580-620 nm;
red: wavelength range of >620-800 nm.

With respect to emitter molecules, such colors refer to the emission maximum. Therefore, exemplarily, a deep blue emitter has an emission maximum in the range of from >420 to 480 nm, a sky blue emitter has an emission maximum in the range of from >480 to 500 nm, a green emitter has an emission maximum in a range of from >500 to 560 nm, a red emitter has an emission maximum in a range of from >620 to 800 nm.

A deep blue emitter may preferably have an emission maximum of below 480 nm, more preferably below 470 nm, even more preferably below 465 nm or even below 460 nm. It will typically be above 420 nm, preferably above 430 nm, more preferably above 440 nm or even above 450 nm.

Accordingly, a further aspect of the present invention relates to an OLED, which exhibits an external quantum efficiency at 1000 cd/m$^2$ of more than 8%, more preferably of more than 10%, more preferably of more than 13%, even more preferably of more than 15% or even more than 20% and/or exhibits an emission maximum between 420 nm and 500 nm, preferably between 430 nm and 490 nm, more preferably between 440 nm and 480 nm, even more preferably between 450 nm and 470 nm and/or exhibits a LT80 value at 500 cd/m$^2$ of more than 100 h, preferably more than 200 h, more preferably more than 400 h, even more preferably more than 750 h or even more than 1000 h. Accordingly, a further aspect of the present invention relates to an OLED, whose emission exhibits a CIEy color coordinate of less than 0.45, preferably less than 0.30, more preferably less than 0.20 or even more preferably less than 0.15 or even less than 0.10.

A further aspect of the present invention relates to an OLED, which emits light at a distinct color point. According to the present invention, the OLED emits light with a narrow emission band (small full width at half maximum (FWHM)). In one aspect, the OLED according to the invention emits light with a FWHM of the main emission peak of less than 0.50 eV, preferably less than 0.48 eV, more preferably less than 0.45 eV, even more preferably less than 0.43 eV or even less than 0.40 eV.

A further aspect of the present invention relates to an OLED, which emits light with CIEx and CIEy color coordinates close to the CIEx (=0.131) and CIEy (=0.046) color coordinates of the primary color blue (CIEx=0.131 and CIEy=0.046) as defined by ITU-R Recommendation BT.2020 (Rec. 2020) and thus is suited for the use in Ultra High Definition (UHD) displays, e.g. UHD-TVs. Accordingly, a further aspect of the present invention relates to an OLED, whose emission exhibits a CIEx color coordinate of between 0.02 and 0.30, preferably between 0.03 and 0.25, more preferably between 0.05 and 0.20 or even more preferably between 0.08 and 0.18 or even between 0.10 and 0.15 and/or a a CIEy color coordinate of between 0.00 and 0.45, preferably between 0.01 and 0.30, more preferably between 0.02 and 0.20 or even more preferably between 0.03 and 0.15 or even between 0.04 and 0.10.

In a further aspect, the invention relates to a method for producing an optoelectronic component. In this case an organic molecule of the invention is used.

The organic electroluminescent device, in particular the OLED according to the present invention can be produced by any means of vapor deposition and/or liquid processing. Accordingly, at least one layer is prepared by means of a sublimation process, prepared by means of an organic vapor phase deposition process, prepared by means of a carrier gas sublimation process, solution processed or printed.

The methods used to produce the organic electroluminescent device, in particular the OLED according to the present invention are known in the art. The different layers are individually and successively deposited on a suitable substrate by means of subsequent deposition processes. The individual layers may be deposited using the same or differing deposition methods.

Vapor deposition processes comprise, for example, thermal (co)evaporation, chemical vapor deposition and physical vapor deposition. For active matrix OLED display, an AMOLED backplane is used as substrate. The individual layer may be processed from solutions or dispersions employing adequate solvents. Solution deposition process exemplarily comprise spin coating, dip coating and jet printing. Liquid processing may optionally be carried out in an inert atmosphere (e.g., in a nitrogen atmosphere) and the solvent may optionally be completely or partially removed by means known in the state of the art.

EXAMPLES

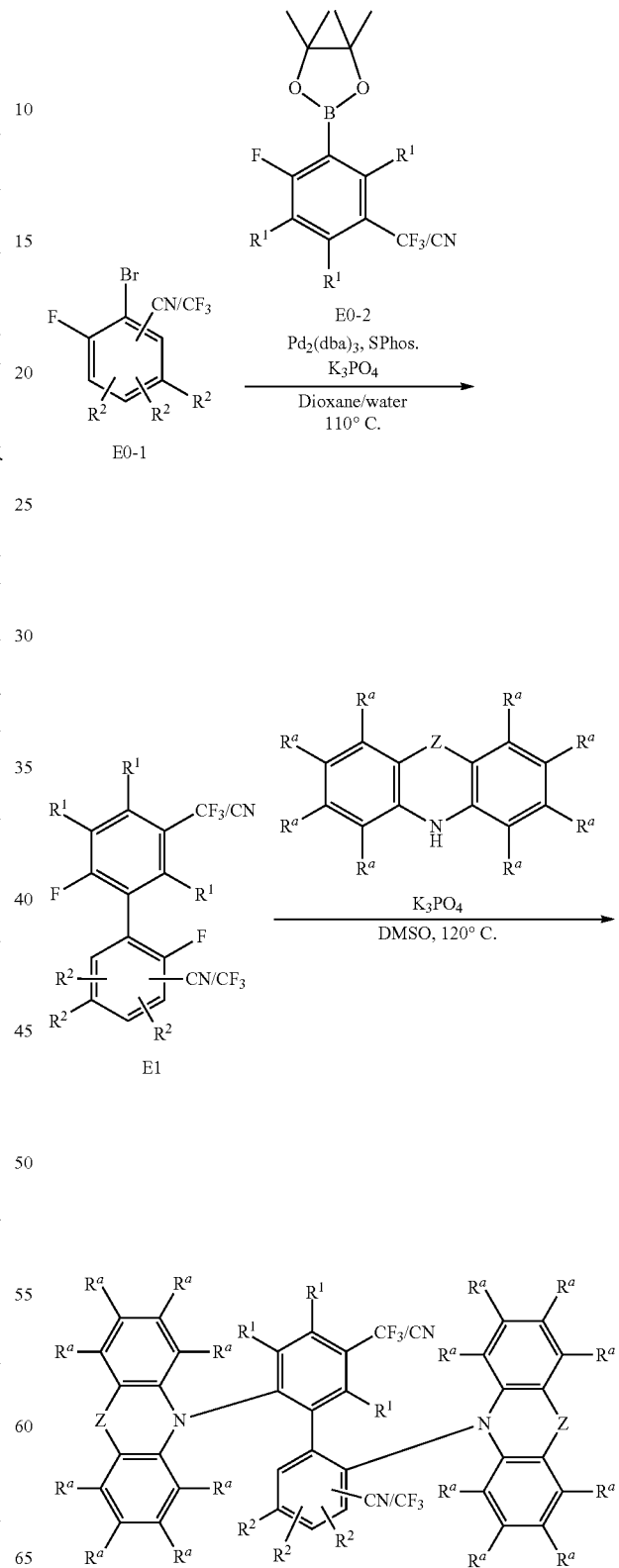

General Procedure for Synthesis AAV1:

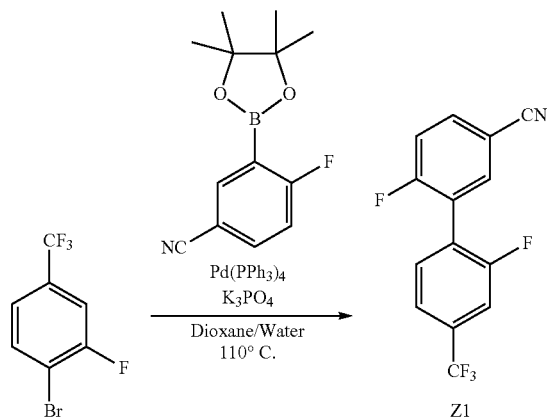 [SMILES: Fc1cc(C(F)(F)F)ccc1Br ; CC1(C)OB(c2cc(C#N)ccc2F)OC1(C)C ; N#Cc1ccc(F)c(-c2ccc(C(F)(F)F)cc2F)c1]

4-bromo-3-fluorobenzotrifluoride (1.0 equivalent), 2-fluoro-5-cyanophenylboronic ester (1.2 equivalents), Pd(PPh$_3$)$_4$(0.02 equivalents), and potassium phosphate (2.50 equivalents) are stirred under nitrogen atmosphere in a dioxane/water mixture (ratio of 10:1) at 100° C. for 22 h. Active carbon and Celite® are added to the reaction mixture and stirred at 90° C. for 10 min, then the mixture is hot filtered and the organic phase is concentrated under reduced pressure. The residue is purified by chromatography and the product Z1 is obtained as a solid.

General Procedure for Synthesis AAV2:

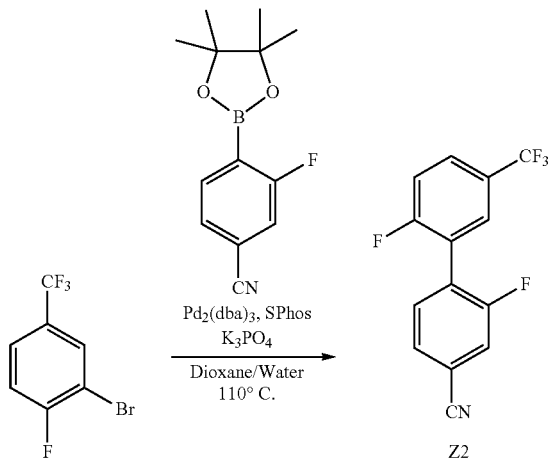 [SMILES: Fc1ccc(C(F)(F)F)cc1Br ; CC1(C)OB(c2ccc(C#N)cc2F)OC1(C)C ; N#Cc1ccc(-c2cc(C(F)(F)F)ccc2F)c(F)c1]

3-bromo-4-fluorobenzotrifluoride (1.0 equivalent), 2-fluoro-4-cyanophenylboronic ester (1.1 equivalents), Pd(dba)$_3$C$_2$(0.04 equivalents), SPhos (0.16 equivalents) and potassium phosphate (2.50 equivalents) are stirred under nitrogen atmosphere in a dioxane/water mixture (ratio of 10:1) at 100° C. for 22 h. Active carbon and Celite® are added to the reaction mixture and stirred at 90° C. for 10 min, then the mixture is hot filtered and the organic phase is concentrated under reduced pressure. The residue is purified by chromatography and the product Z2 is obtained as a solid.

General Procedure for Synthesis AAV3:

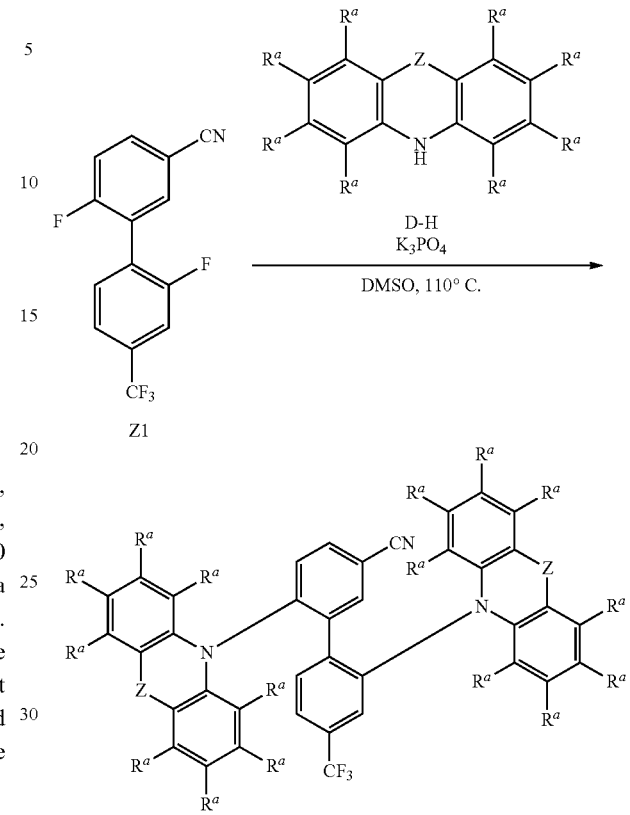

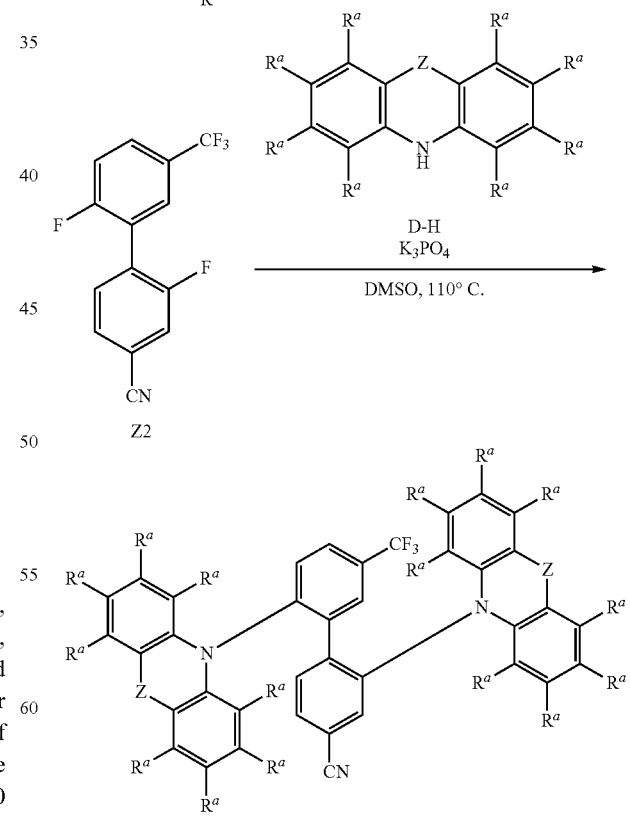

Z1 or Z2 (1 equivalent each), the corresponding donor molecule D-H (2.00 equivalents) and tribasic potassium phosphate (5.0 equivalents) are suspended under nitrogen atmosphere in DMSO and stirred at 110° C. for 23 h. The reaction mixture is poured into a saturated sodium chloride solution and the resulting precipitate is filtered. Subsequently the residue is dissolved in dichloromethane and washed with saturated sodium chloride solution, dried over $MgSO_4$ and the solvent evaporated under reduced pressure. The crude product is purified by chromatography.

In particular, the donor molecule D-H is a 3,6-substituted carbazole (e.g., 3,6-dimethylcarbazole, 3,6-diphenylcarbazole, 3,6-di-tert-butylcarbazole), a 2,7-substituted carbazole (e.g., 2,7-dimethylcarbazole, 2,7-diphenylcarbazole, 2,7-di-tert-butylcarbazole), a 1,8-substituted carbazole (e.g., 1,8-dimethylcarbazole, 1,8-diphenylcarbazole, 1,8-di-tert-butylcarbazole), a 1-substituted carbazole (e.g., 1-methylcarbazole, 1-phenylcarbazole, 1-tert-butylcarbazole), a 2-substituted carbazole (e.g., 2-methylcarbazole, 2-phenylcarbazole, 2-tert-butylcarbazole), or a 3-substituted carbazole (e.g., 3-methylcarbazole, 3-phenylcarbazole, 3-tert-butylcarbazole).

Exemplarily a halogen-substituted carbazole, particularly 3-bromocarbazole, can be used as D-H. In a subsequent reaction a boronic acid ester functional group or boronic acid functional group may be exemplarily introduced at the position of the one or more halogen substituents, which was introduced via D-H, to yield the corresponding carbazol-3-ylboronic acid ester or carbazol-3-ylboronic acid, e.g., via the reaction with bis(pinacolato)diboron (CAS No. 73183-34-3). Subsequently, one or more substituents $R^a$ may be introduced in place of the boronic acid ester group or the boronic acid group via a coupling reaction with the corresponding halogenated reactant $R^a$—Hal, preferably $R^a$—Cl and $R^a$—Br.

Alternatively, one or more substituents $R^a$ may be introduced at the position of the one or more halogen substituents, which was introduced via D-H, via the reaction with a boronic acid of the substituent $R^a$ [$R^a$—$B(OH)_2$] or a corresponding boronic acid ester.

In particular, the synthesis of an organic molecule according to the invention can be performed according to the General synthesis scheme I with the synthesis conditions provided by the General procedure for synthesis AAV1, AAV2, and AAV3, wherein E0-1 is a bromo-fluoro-substituted trifluorobenzoztrifluoride selected from the group consisting of 4-bromo-3-fluorobenzotrifluoride, 3-bromo-4-fluorobenzotrifluoride, 3-bromo-2-fluorobenzotrifluoride, 2-bromo-3-fluorobenzotrifluoride; and E0-2 is a fluoro-cynaophenylboronic ester selected from the group consisting of 2-fluoro-5-cyanophenylboronic ester, 2-fluoro-4-cyanophenylboronic ester, 2-fluoro-3-cyanophenylboronic ester, 2-fluoro-6-cyanophenylboronic ester.

Cyclic Voltammetry

Cyclic voltammograms are measured from solutions having concentration of $10^{-3}$ mol/L of the organic molecules in dichloromethane or a suitable solvent and a suitable supporting electrolyte (e.g. 0.1 mol/L of tetrabutylammonium hexafluorophosphate). The measurements are conducted at room temperature under nitrogen atmosphere with a three-electrode assembly (Working and counter electrodes: Pt wire, reference electrode: Pt wire) and calibrated using $FeCp_2/FeCp_2^+$ as internal standard. The HOMO data was corrected using ferrocene as internal standard against a standard calomel electrode (SCE).

Density Functional Theory Calculation

Molecular structures are optimized employing the BP86 functional and the resolution of identity approach (RI). Excitation energies are calculated using the (BP86) optimized structures employing Time-Dependent DFT (TD-DFT) methods. Orbital and excited state energies are calculated with the B3LYP functional. Def2-SVP basis sets (and a m4-grid for numerical integration are used. The Turbomole program package is used for all calculations.

Photophysical Measurements

Sample pretreatment: Spin-coating

Apparatus: Spin150, SPS euro.

The sample concentration is 10 mg/ml, dissolved in a suitable solvent.

Program: 1) 3 s at 400 U/min; 20 s at 1000 U/min at 1000 Upm/s. 3) 10 s at 4000 U/min at 1000 Upm/s. After coating, the films are tried at 70° C. for 1 min.

Photoluminescence Spectroscopy and TCSPC (Time-Correlated Single-Photon Counting)

Steady-state emission spectroscopy is measured by a Horiba Scientific, Modell FluoroMax-4 equipped with a 150 W Xenon-Arc lamp, excitation- and emissions monochromators and a Hamamatsu R928 photomultiplier and a time-correlated single-photon counting option. Emissions and excitation spectra are corrected using standard correction fits.

Excited state lifetimes are determined employing the same system using the TCSPC method with FM-2013 equipment and a Horiba Yvon TCSPC hub.

Excitation sources:

NanoLED 370 (wavelength: 371 nm, puls duration: 1.1 ns)

NanoLED 290 (wavelength: 294 nm, puls duration: <1 ns)

SpectraLED 310 (wavelength: 314 nm)

SpectraLED 355 (wavelength: 355 nm).

Data analysis (exponential fit) is done using the software suite DataStation and DAS6 analysis software. The fit is specified using the chi-squared-test.

Photoluminescence Quantum Yield Measurements

For photoluminescence quantum yield (PLQY) measurements an Absolute PL Quantum Yield Measurement C9920-03G system (Hamamatsu Photonics) is used. Quantum yields and CIE coordinates are determined using the software U6039-05 version 3.6.0.

Emission maxima are given in nm, quantum yields Q0 in % and CIE coordinates as x,y values. PLQY is determined using the following protocol:

1) Quality assurance: Anthracene in ethanol (known concentration) is used as reference
2) Excitation wavelength: the absorption maximum of the organic molecule is determined and the molecule is excited using this wavelength
3) Measurement Quantum yields are measured for sample of solutions or films under nitrogen atmosphere. The yield is calculated using the equation:

$$\Phi_{PL} = \frac{n_{photon}, \text{emitted}}{n_{photon}, \text{absorbed}} = \frac{\int \frac{\lambda}{hc}[Int^{sample}_{emitted}(\lambda) - Int^{sample}_{absorbed}(\lambda)]d\lambda}{\int \frac{\lambda}{hc}[Int^{reference}_{emitted}(\lambda) - Int^{reference}_{absorbed}(\lambda)]d\lambda}$$

wherein $n_{photon}$ denotes the photon count and Int. the intensity.

Production and Characterization of Organic Electroluminescence Devices

OLED devices comprising organic molecules according to the invention can be produced via vacuum-deposition methods. If a layer contains more than one compound, the weight-percentage of one or more compounds is given in %. The total weight-percentage values amount to 100%, thus if a value is not given, the fraction of this compound equals to the difference between the given values and 100%.

The not fully optimized OLEDs are characterized using standard methods and measuring electroluminescence spectra, the external quantum efficiency (in %) in dependency on the intensity, calculated using the light detected by the photodiode, and the current. The OLED device lifetime is extracted from the change of the luminance during operation at constant current density. The LT50 value corresponds to the time, where the measured luminance decreased to 50% of the initial luminance, analogously LT80 corresponds to the time point, at which the measured luminance decreased to 80% of the initial luminance, LT 95 to the time point, at which the measured luminance decreased to 95% of the initial luminance etc.

Accelerated lifetime measurements are performed (e.g. applying increased current densities). Exemplarily LT80 values at 500 cd/m² are determined using the following equation:

$$LT80\left(500\frac{cd^2}{m^2}\right) = LT80(L_0)\left(\frac{L_0}{500\frac{cd^2}{m^2}}\right)^{1.6}$$

wherein $L_0$ denotes the initial luminance at the applied current density.

The values correspond to the average of several pixels (typically two to eight), the standard deviation between these pixels is given.

HPLC-MS:

HPLC-MS spectroscopy is performed on a HPLC by Agilent (1100 series) with MS-detector (Thermo LTQ XL). A reverse phase column 4.6 mm×150 mm, particle size 5.0 µm from Waters (without pre-column) is used in the HPLC. The HPLC-MS measurements are performed at room temperature (rt) with the solvents acetonitrile, water and THF in the following concentrations:

| solvent A: | H₂O (90%) | MeCN (10%) |
| solvent B: | H₂O (10%) | MeCN (90%) |
| solvent C: | THF (100%) | |

From a solution with a concentration of 0.5 mg/ml an injection volume of 15 µL is taken for the measurements. The following gradient is used:

| Flow rate [ml/min] | time [min] | A[%] | B[%] | D[%] |
|---|---|---|---|---|
| 3 | 0 | 40 | 50 | 10 |
| 3 | 10 | 10 | 15 | 75 |
| 3 | 16 | 10 | 15 | 75 |
| 3 | 16.01 | 40 | 50 | 10 |
| 3 | 20 | 40 | 50 | 10 |

Ionisation of the probe is performed by APCI (atmospheric pressure chemical ionization).

Example 1

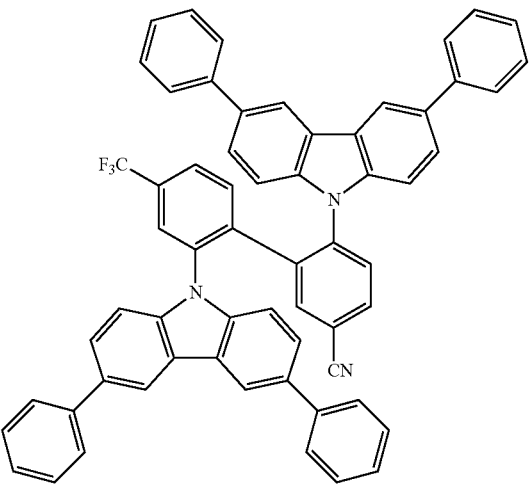 [SMILES: N#Cc1ccc(-n2c3ccc(-c4ccccc4)cc3c3cc(-c4ccccc4)ccc32)c(-c2ccc(C(F)(F)F)cc2-n2c3ccc(-c4ccccc4)cc3c3cc(-c4ccccc4)ccc32)c1]

Example 1 was synthesized according to AAV1 (yield 16%) and AAV3 (yield 71%).

FIG. 1 depicts the emission spectrum of example 1 (10% by weight in PMMA). The emission maximum ($\lambda_{max}$) is at 451 nm. The photoluminescence quantum yield (PLQY) is 54%, the full width at half maximum (FWHM) is 0.40 eV and the emission lifetime is 76 ρs. The resulting $CIE_x$ coordinate is determined at 0.15 and the $CIE_y$ coordinate at 0.12.

Example 2

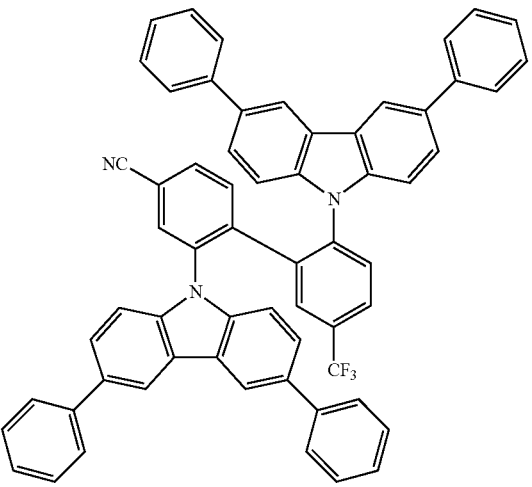 [SMILES: N#Cc1ccc(-c2cc(C(F)(F)F)ccc2-n2c3ccc(-c4ccccc4)cc3c3cc(-c4ccccc4)ccc32)c(-n2c3ccc(-c4ccccc4)cc3c3cc(-c4ccccc4)ccc32)c1]

Example 2 was synthesized according to AAV2 (yield 62%) and AAV3 (yield 37%).

Figure 2:
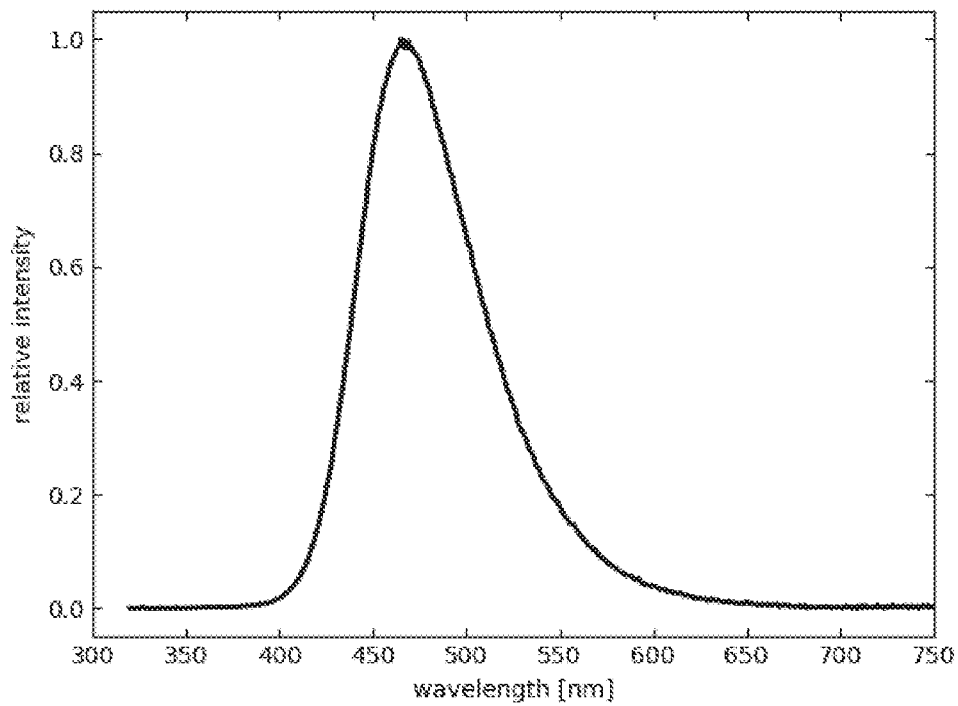
FIG. 2 is an emission spectrum of Example 2 (10% by weight) in PMMA.

FIG. 2 depicts the emission spectrum of example 2 (10% by weight in PMMA). The emission maximum ($\Delta_{max}$) is at 467 nm. The photoluminescence quantum yield (PLQY) is 67%, the full width at half maximum (FWHM) is 0.40 eV and the emission lifetime is 37 µs. The resulting CIEx coordinate is determined at 0.16 and the $CIE_y$ coordinate at 0.20.

Additional Examples of Organic Molecules of the Invention
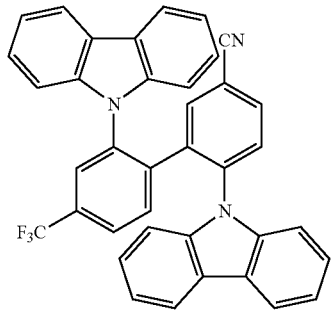
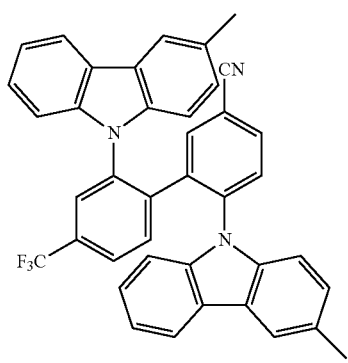
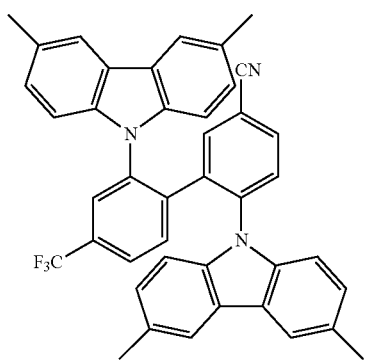
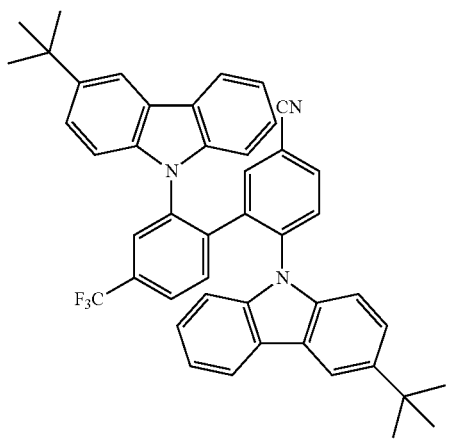
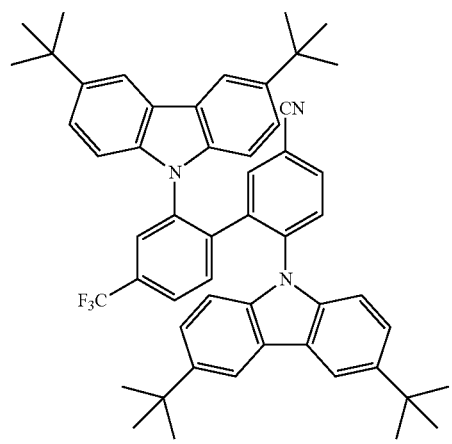
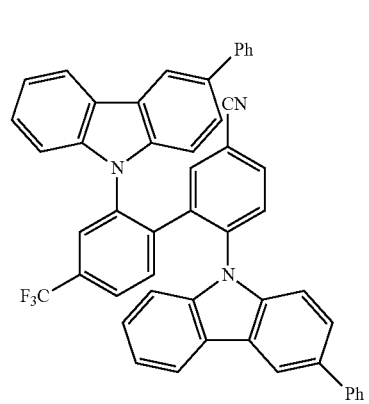
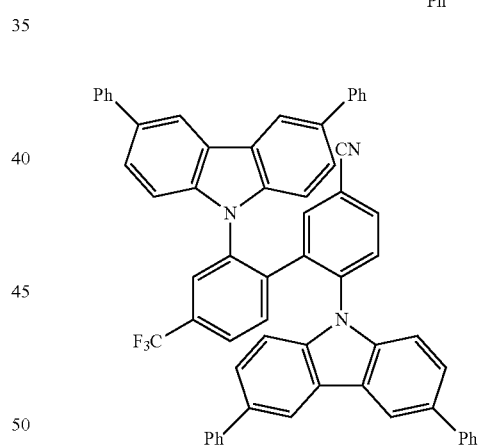
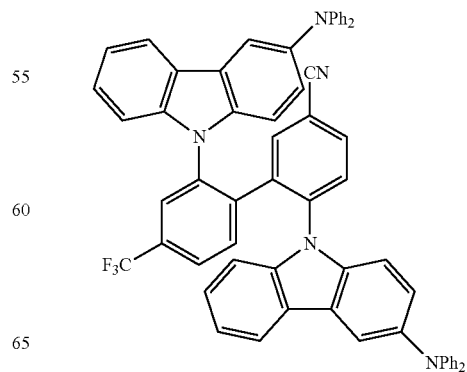

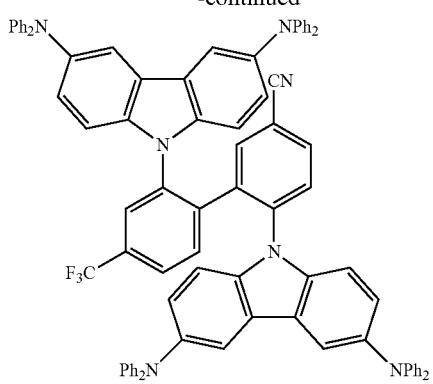
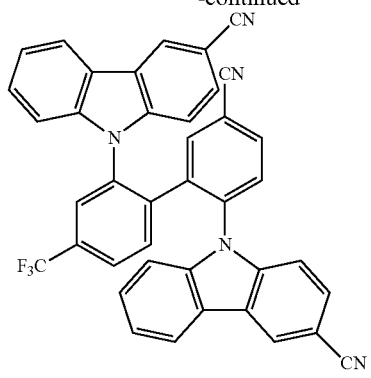
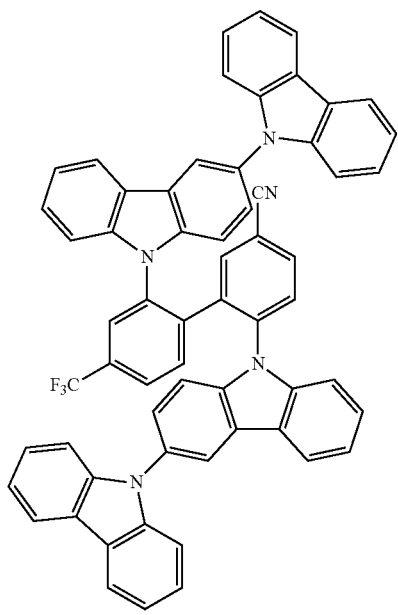
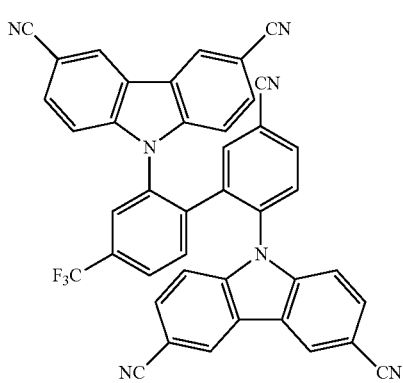
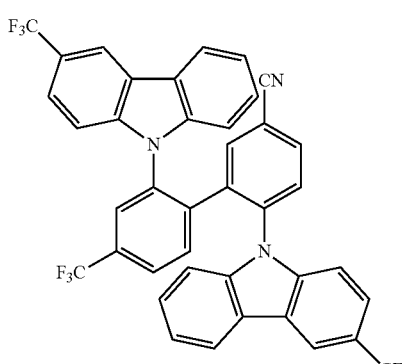
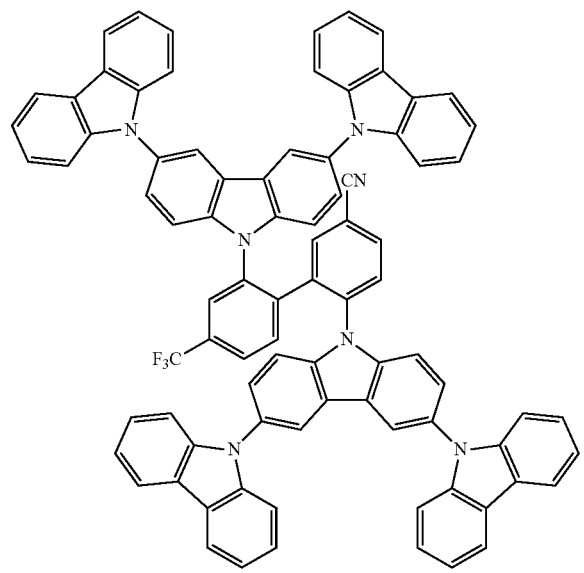
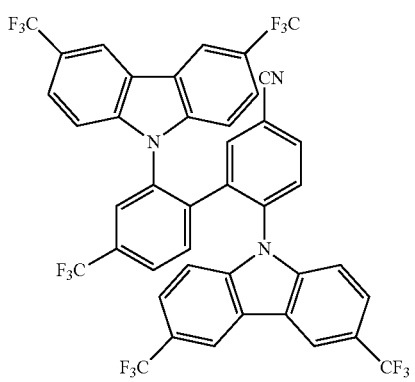

-continued
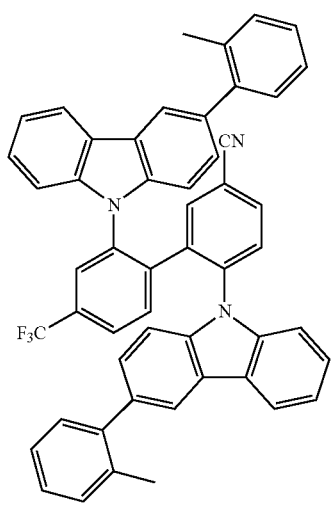
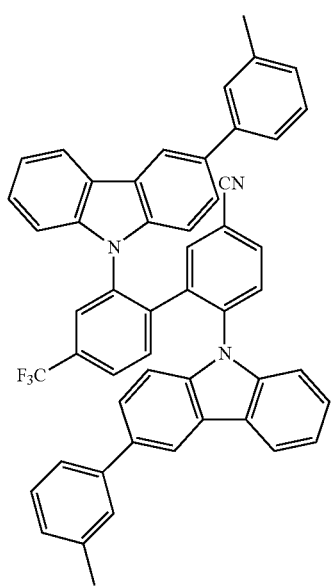
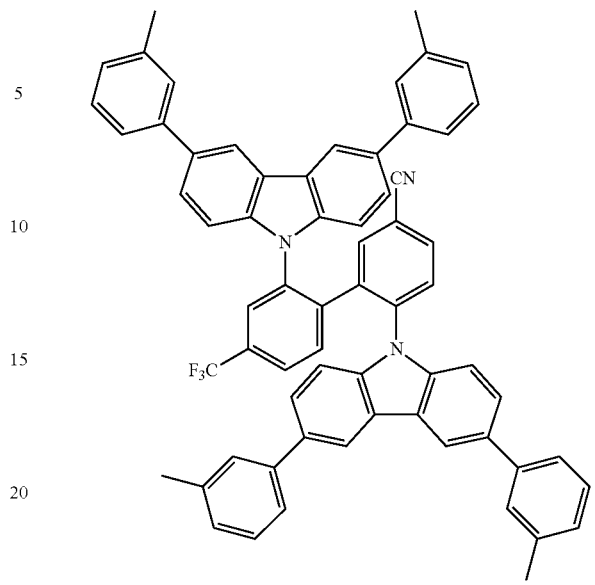
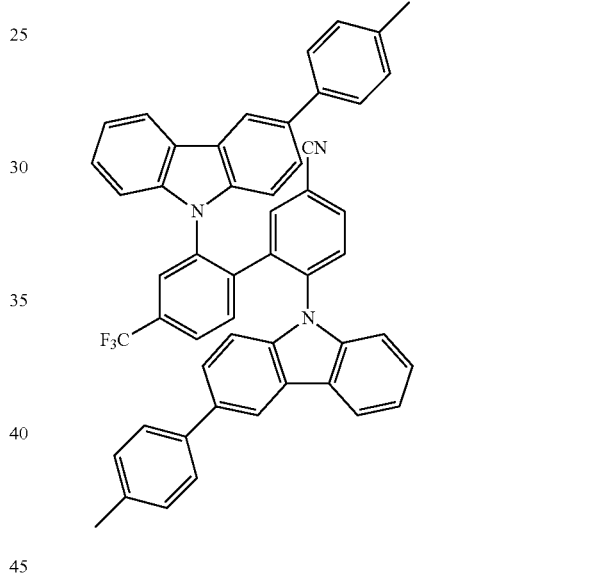
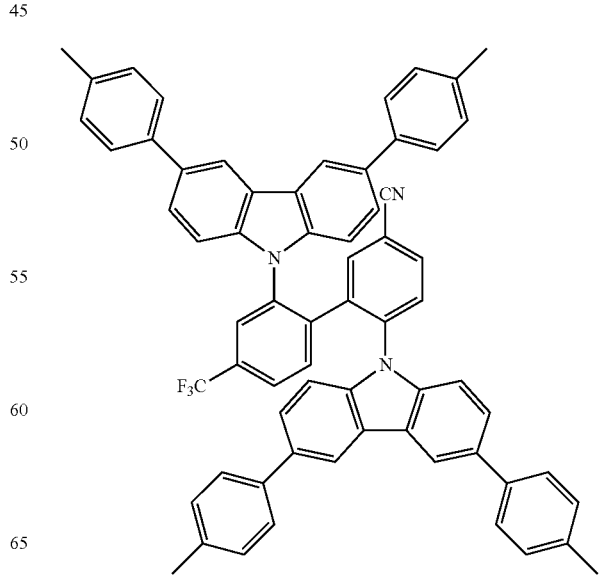

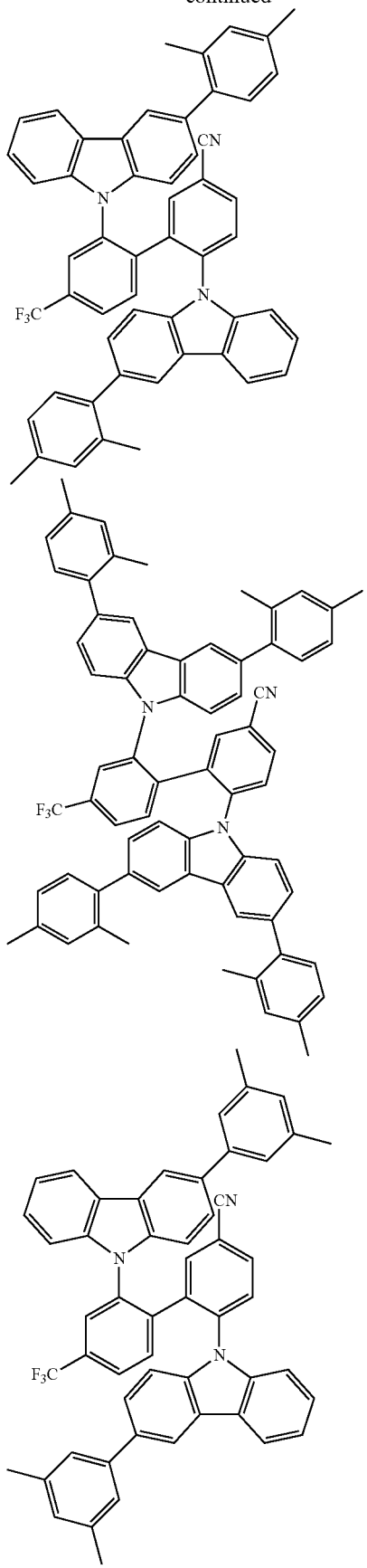
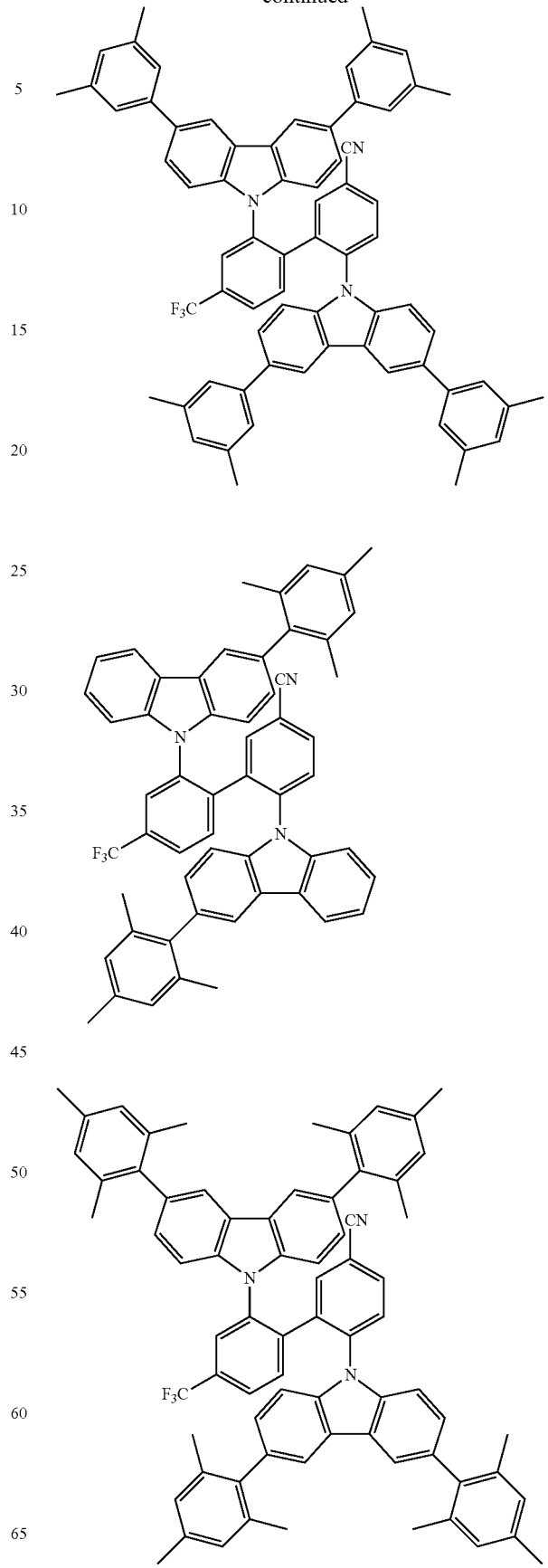

51
-continued
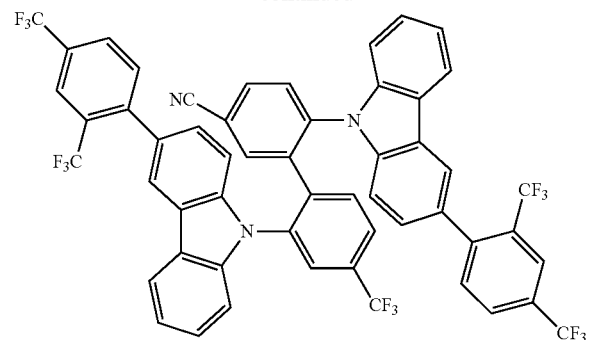
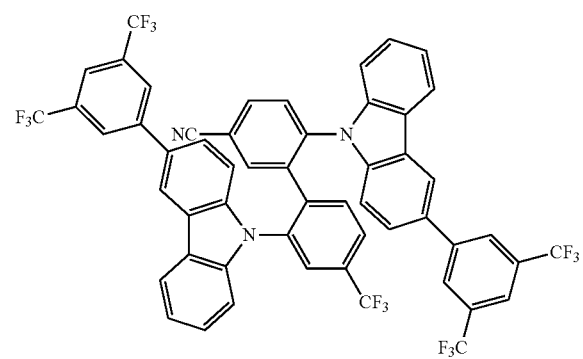
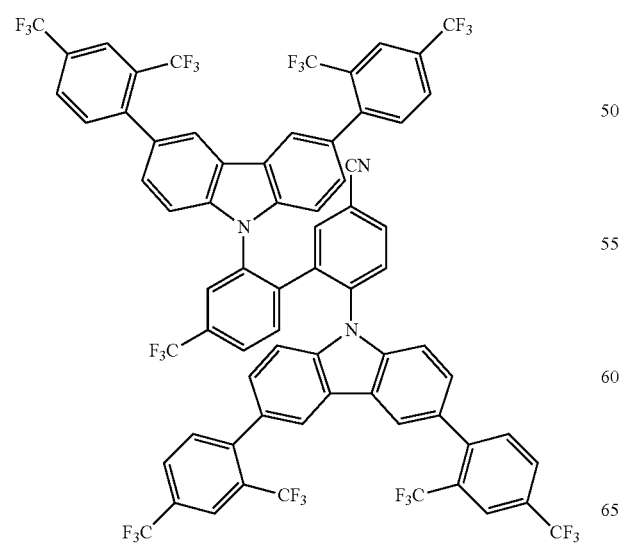
52
-continued
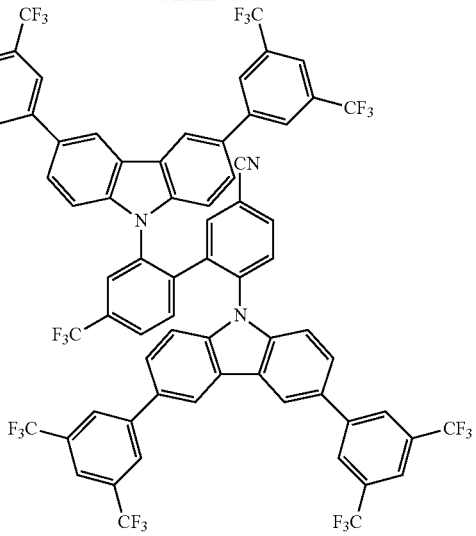
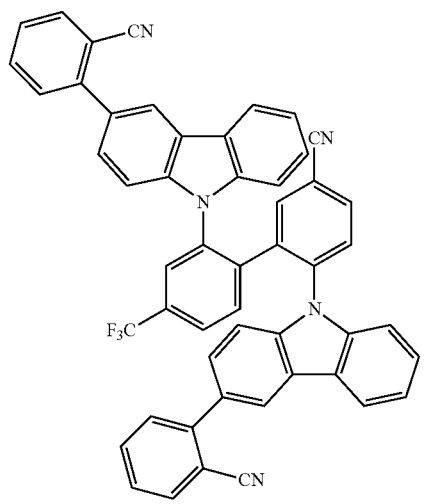
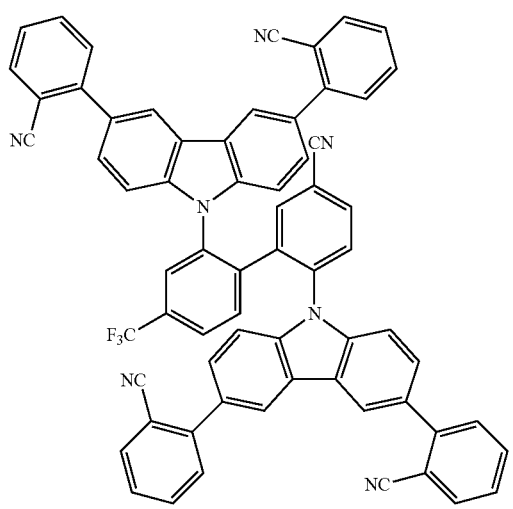

-continued
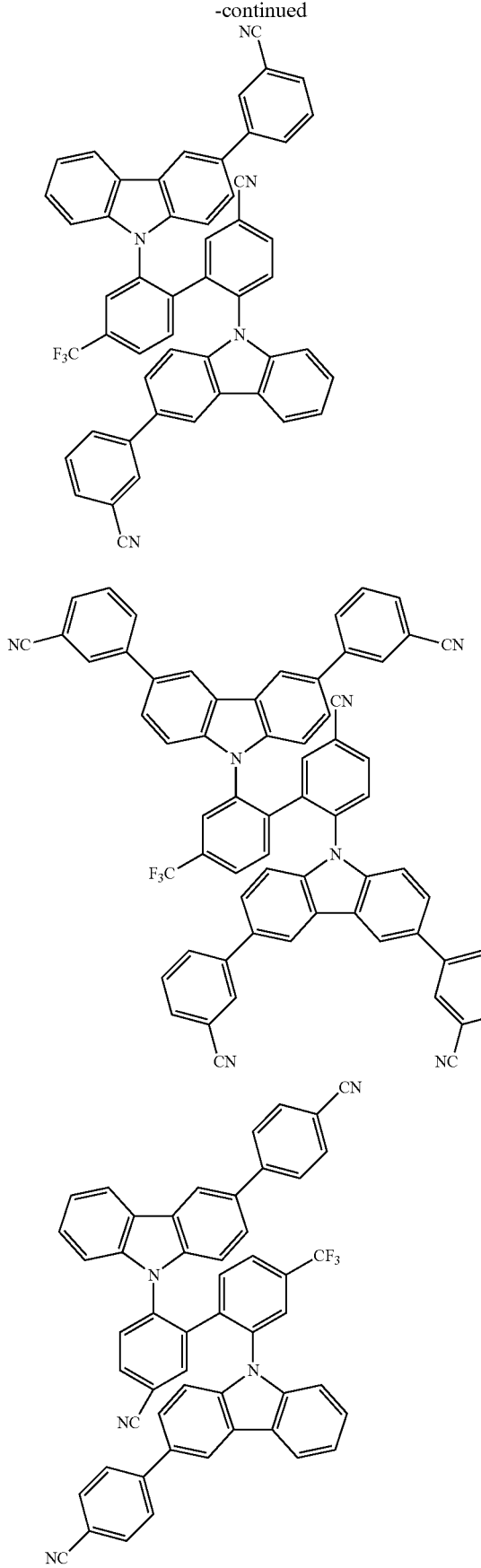
-continued
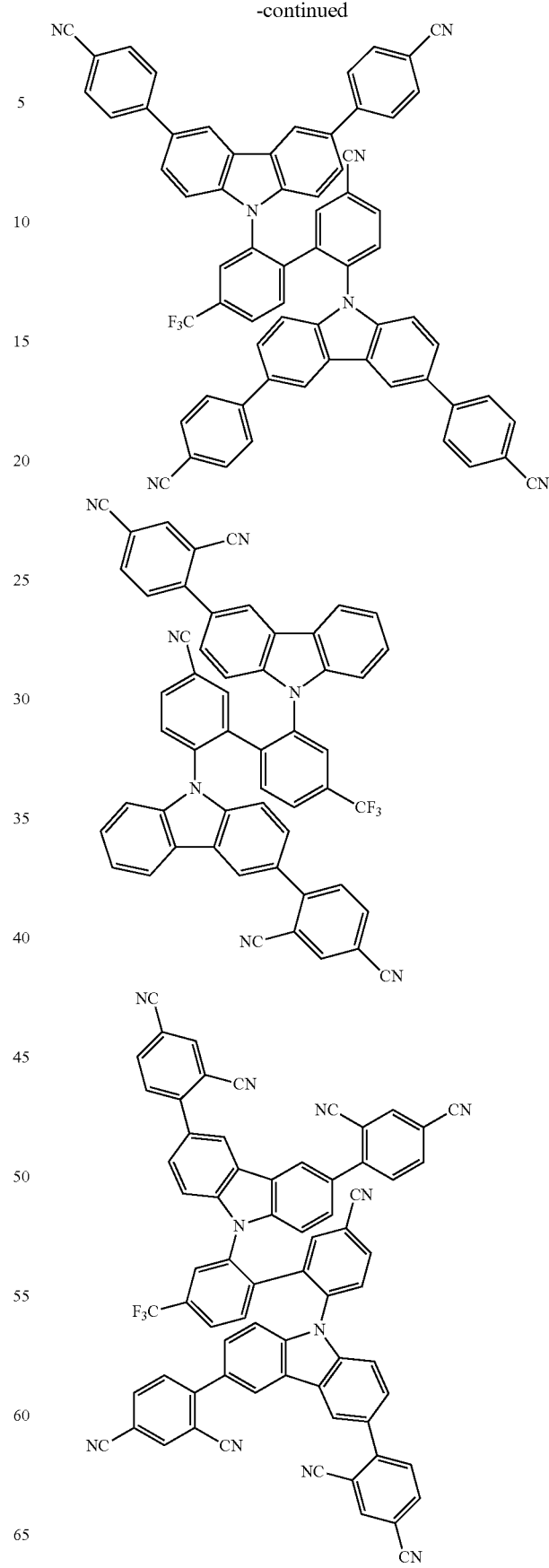

55
-continued
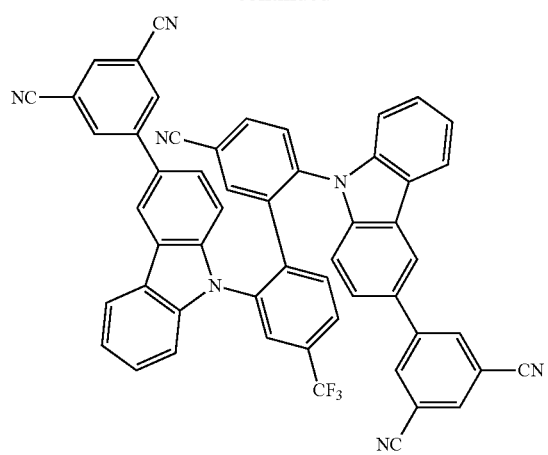
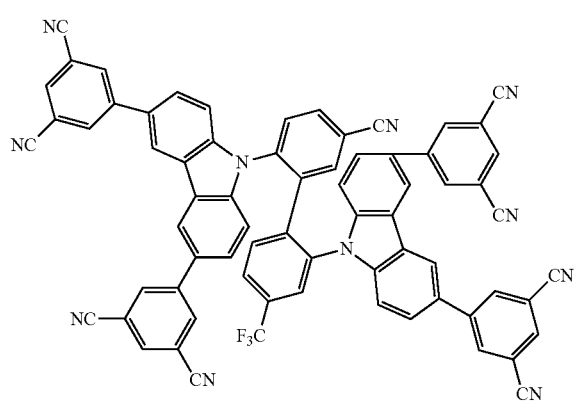
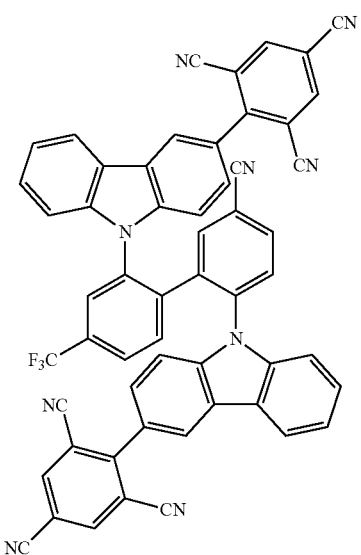
56
-continued
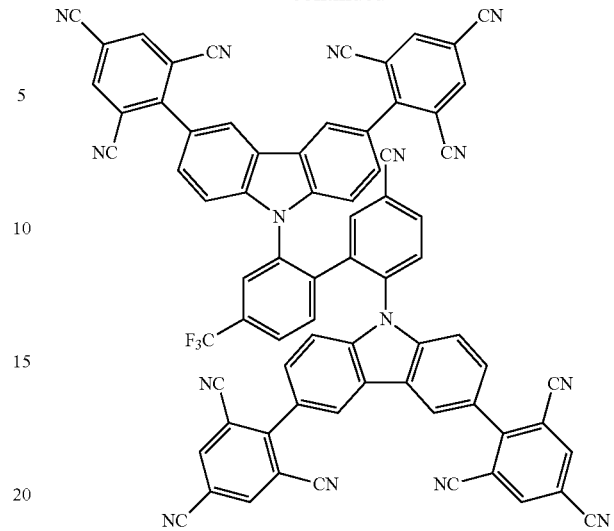
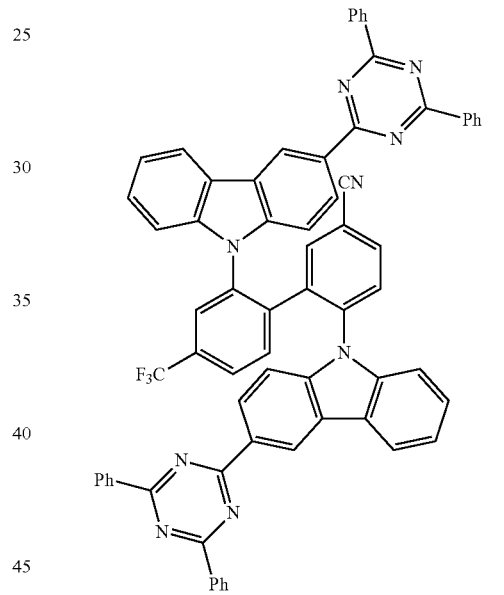
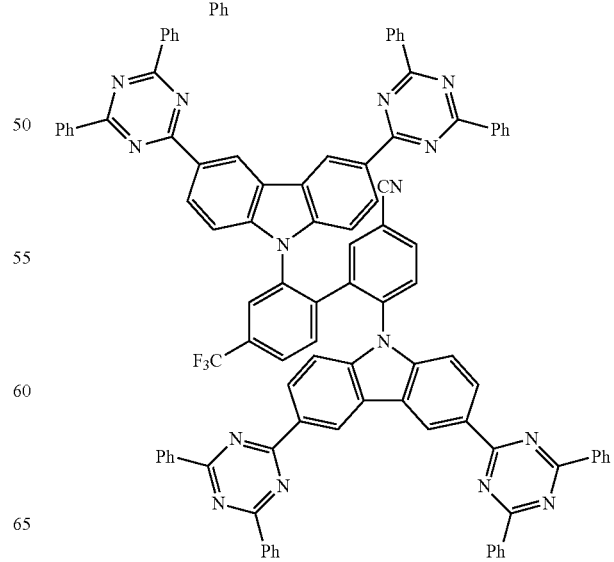

57
-continued
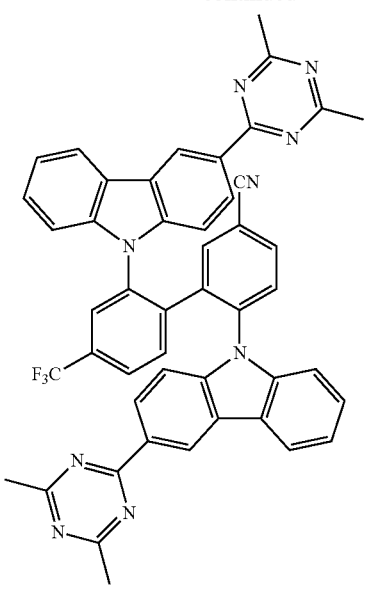
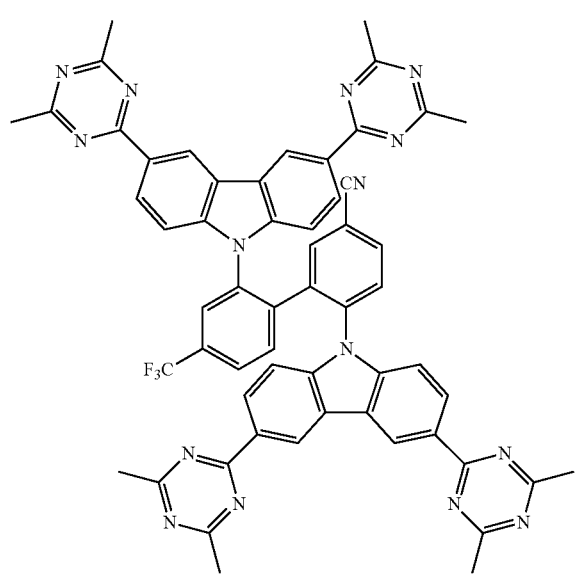
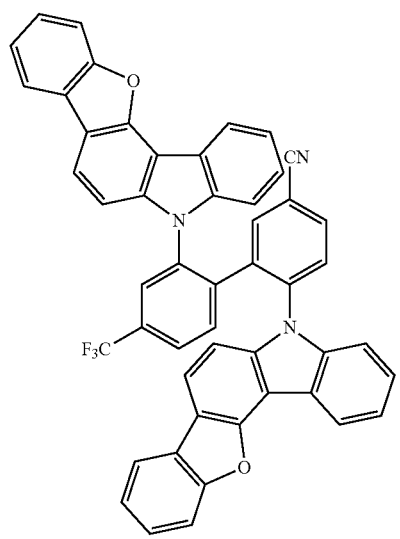
58
-continued
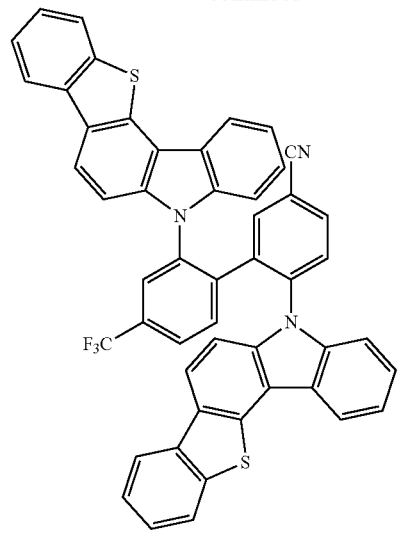
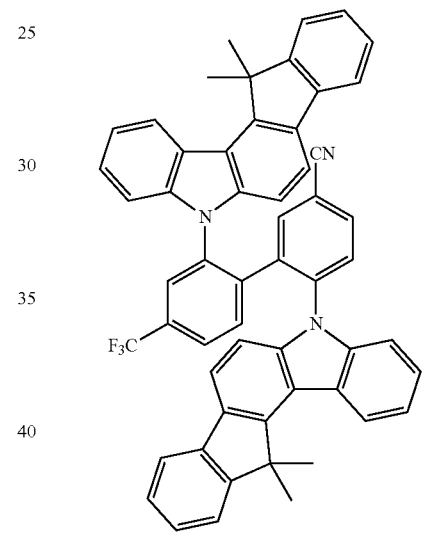
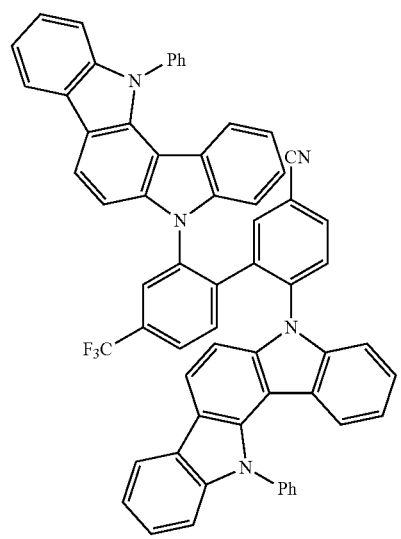

-continued
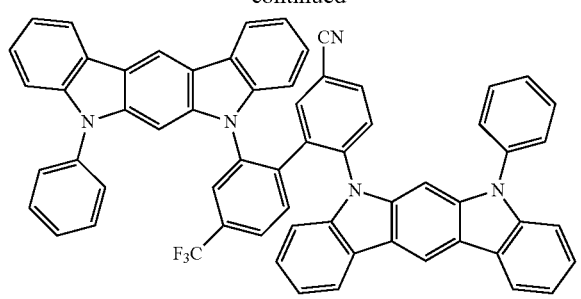
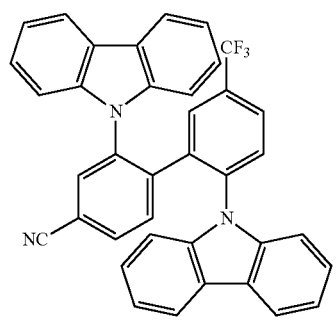
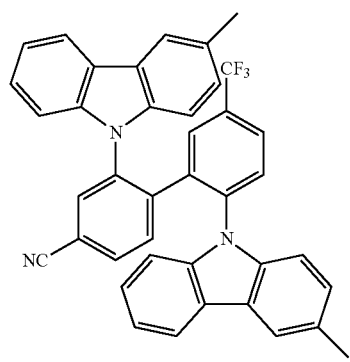
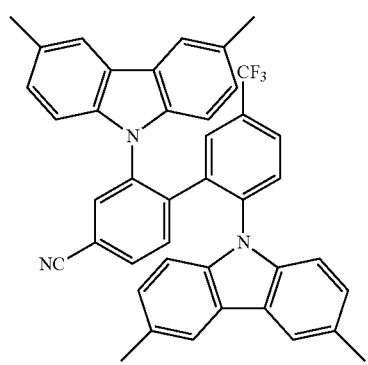
-continued
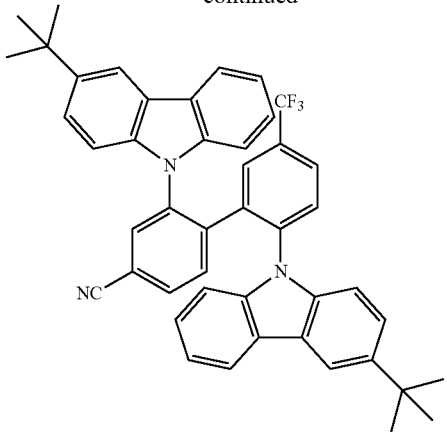
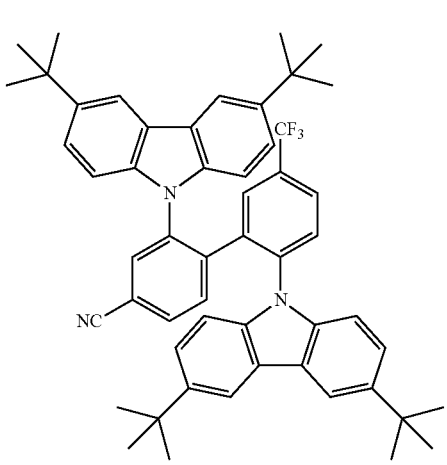
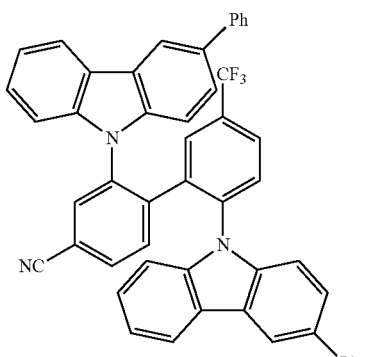
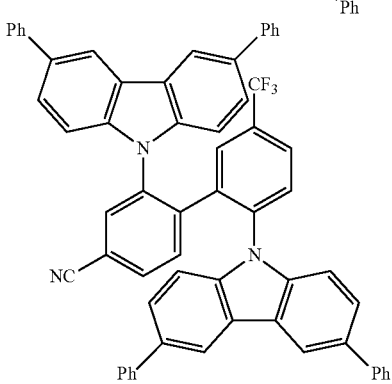

-continued
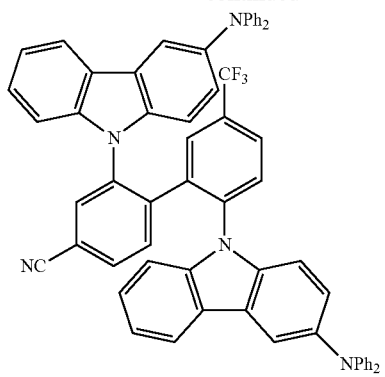
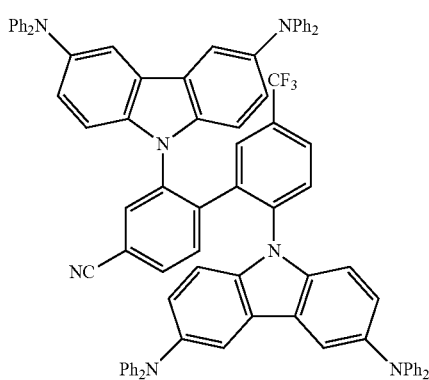
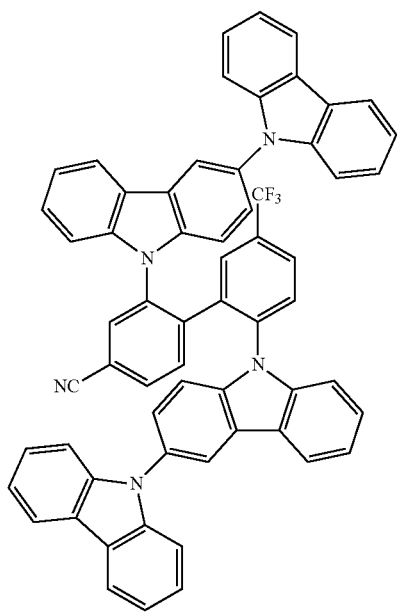
-continued
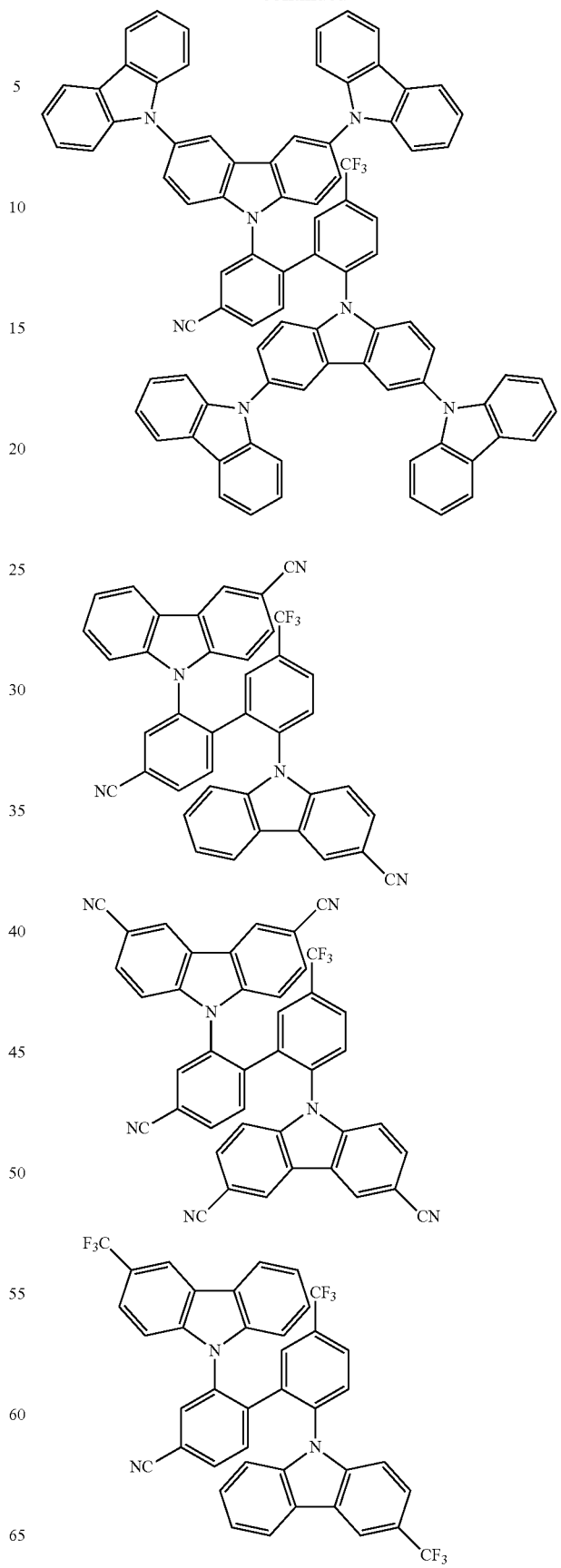

63
-continued
64
-continued
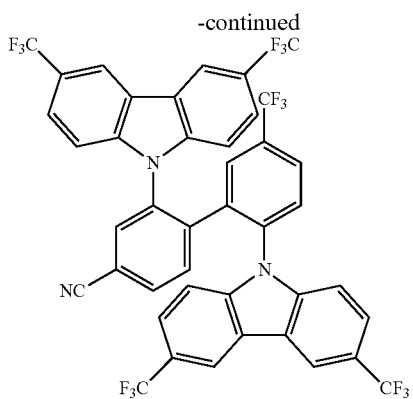
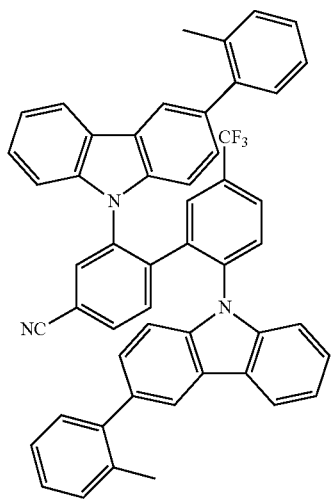
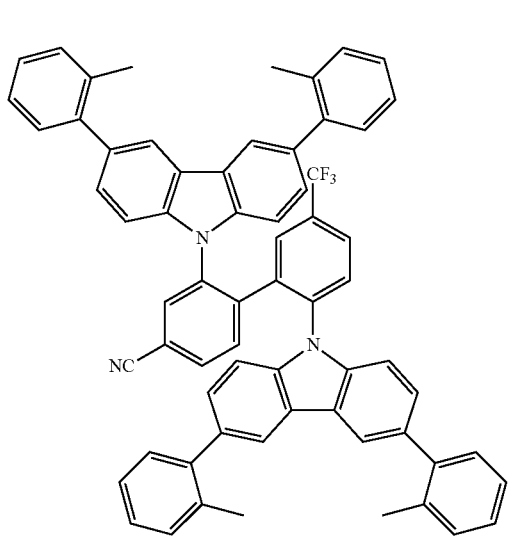
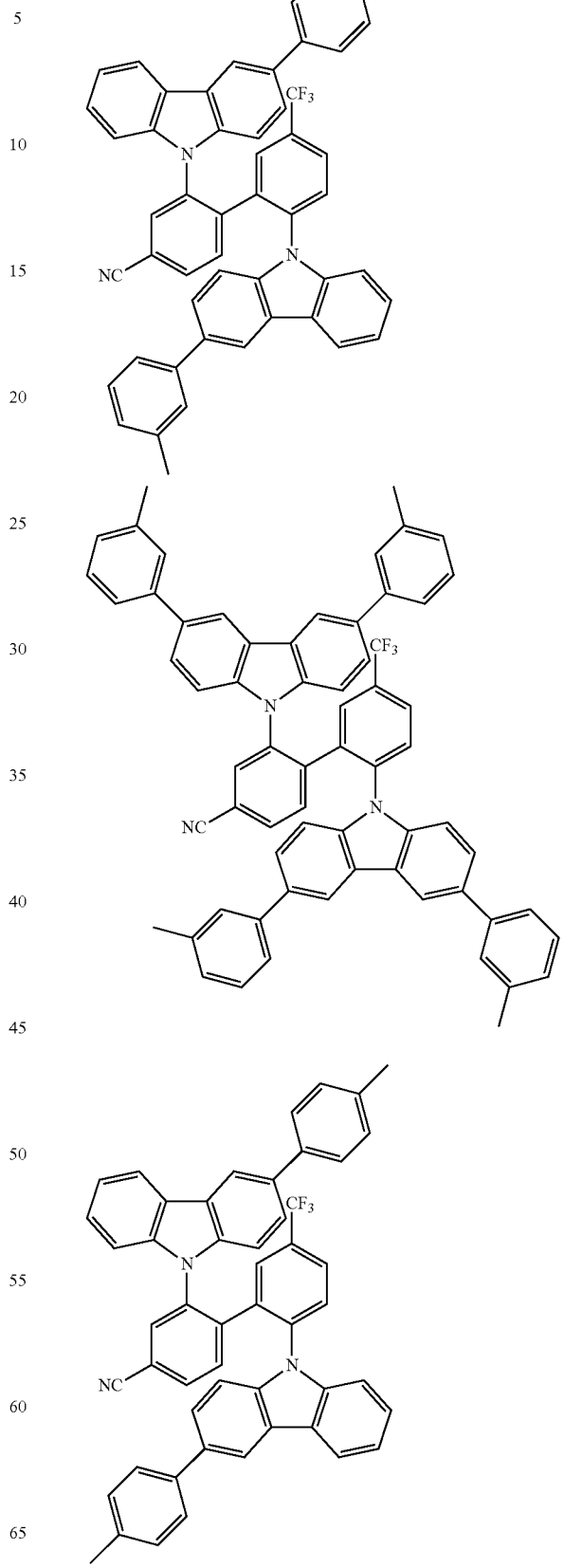
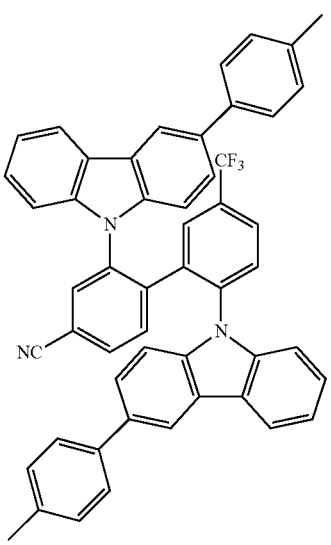

65
-continued
66
-continued
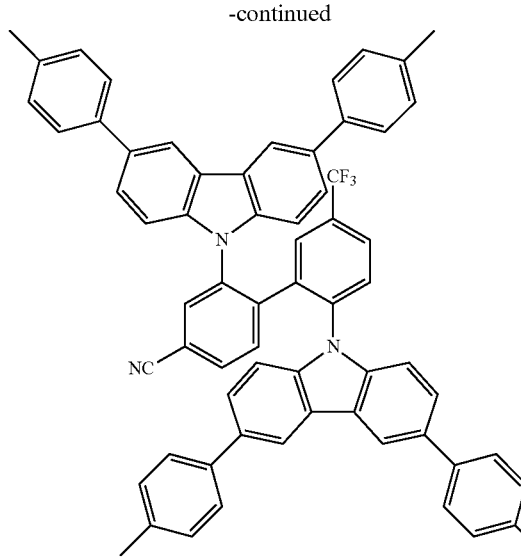
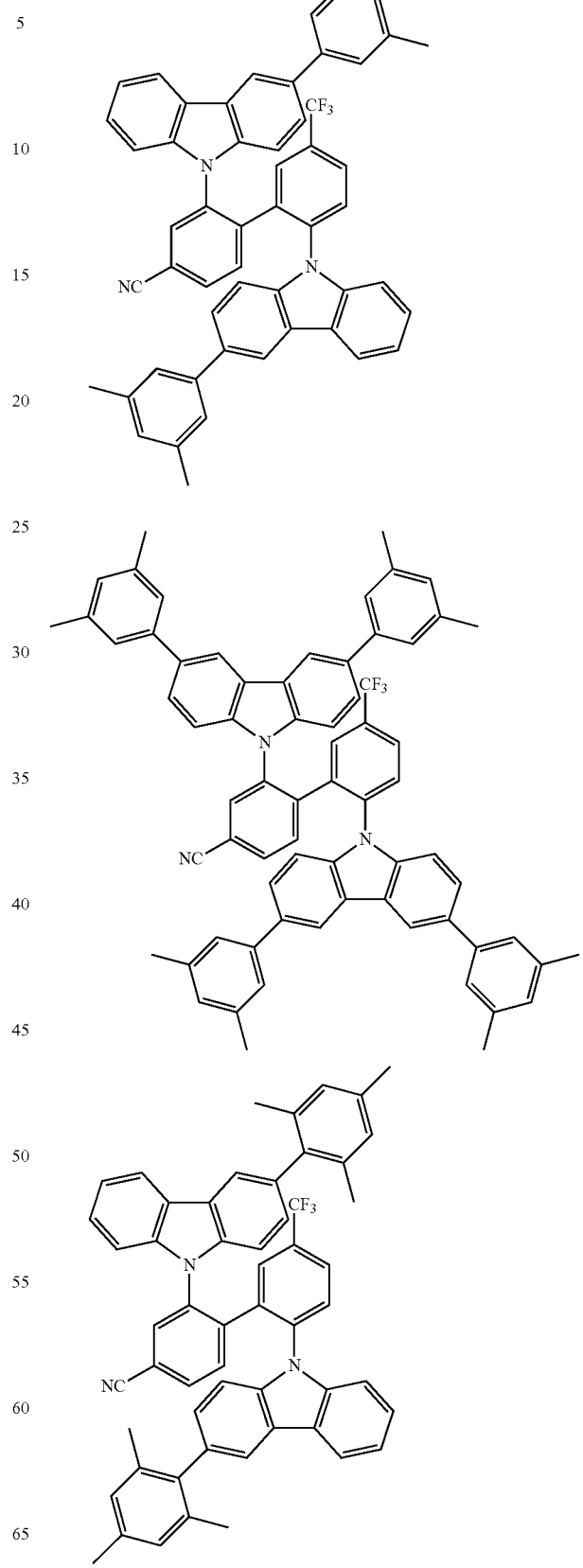

67
-continued
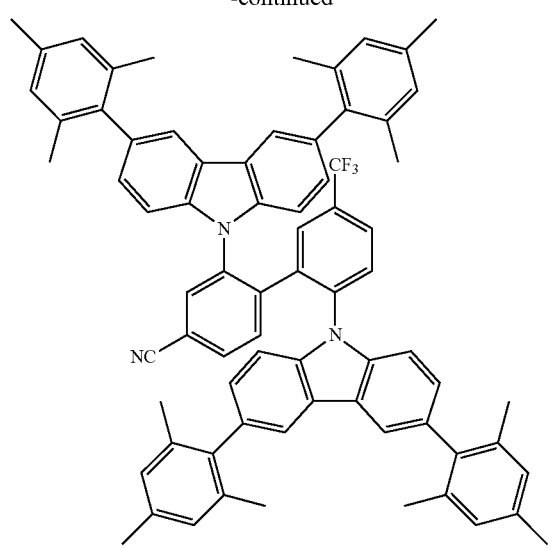
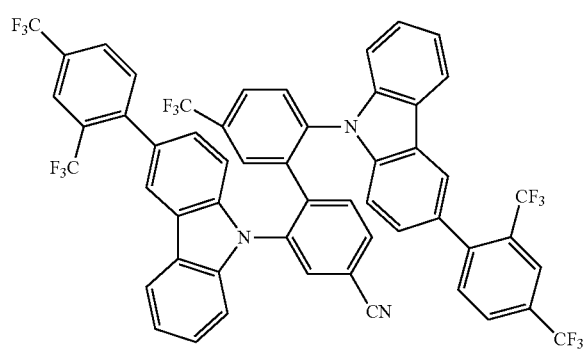
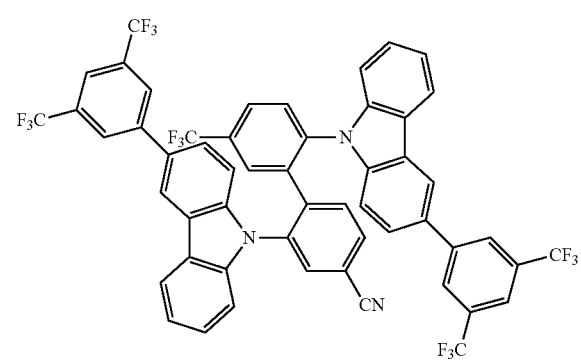
68
-continued
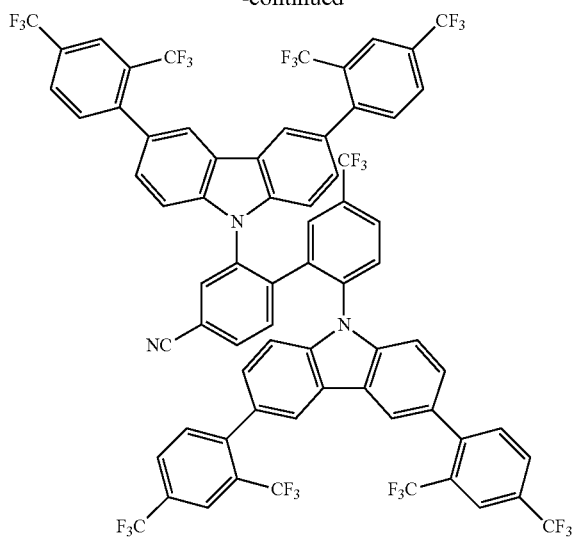
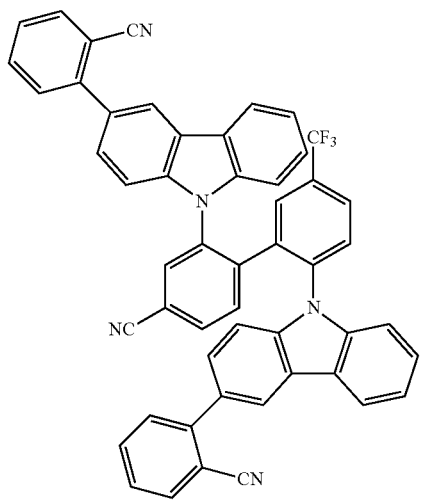

69
-continued
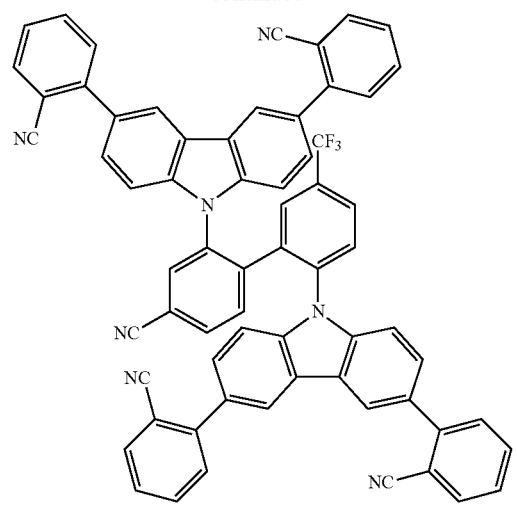
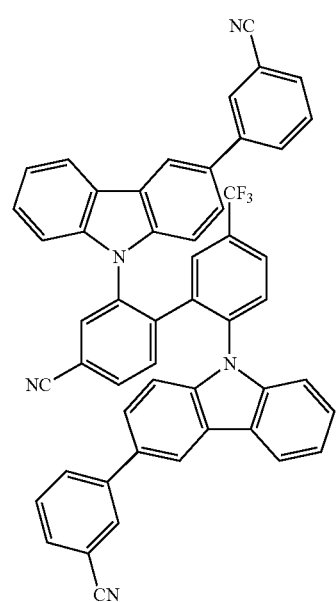
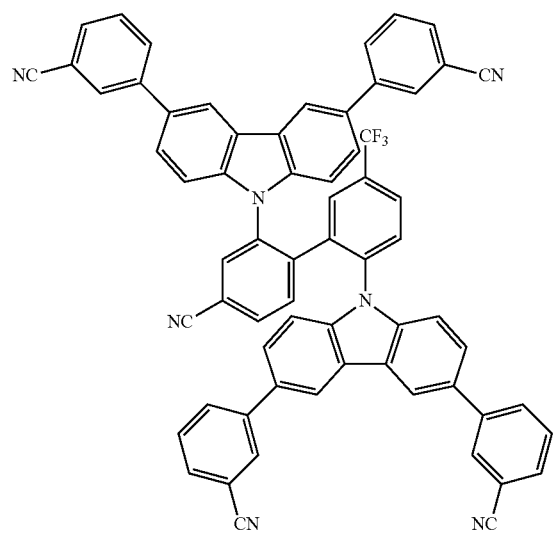
70
-continued
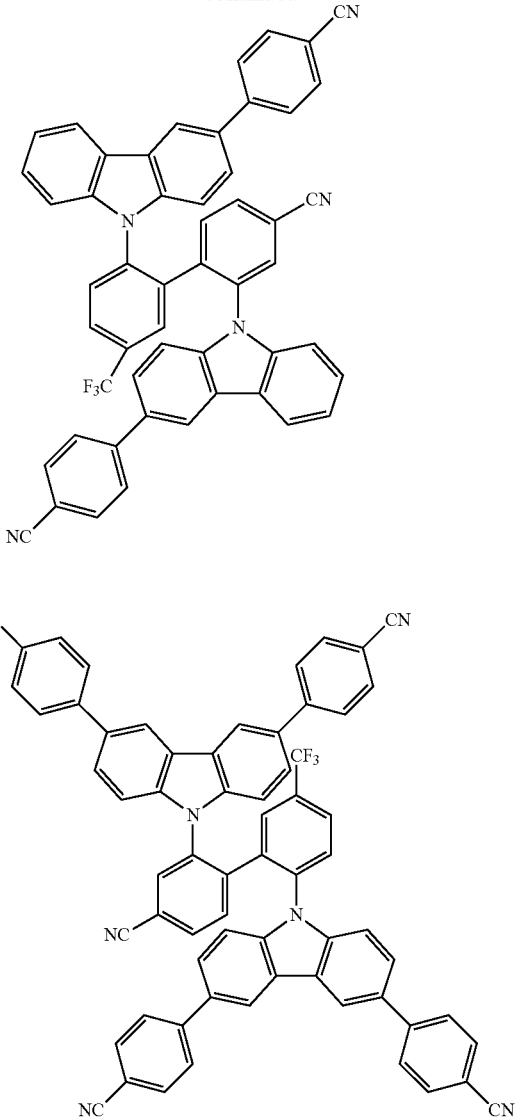
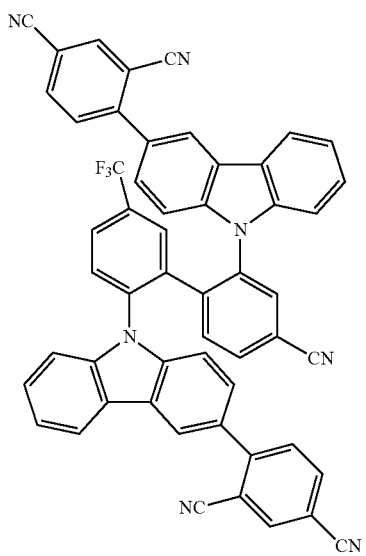

71
-continued
72
-continued
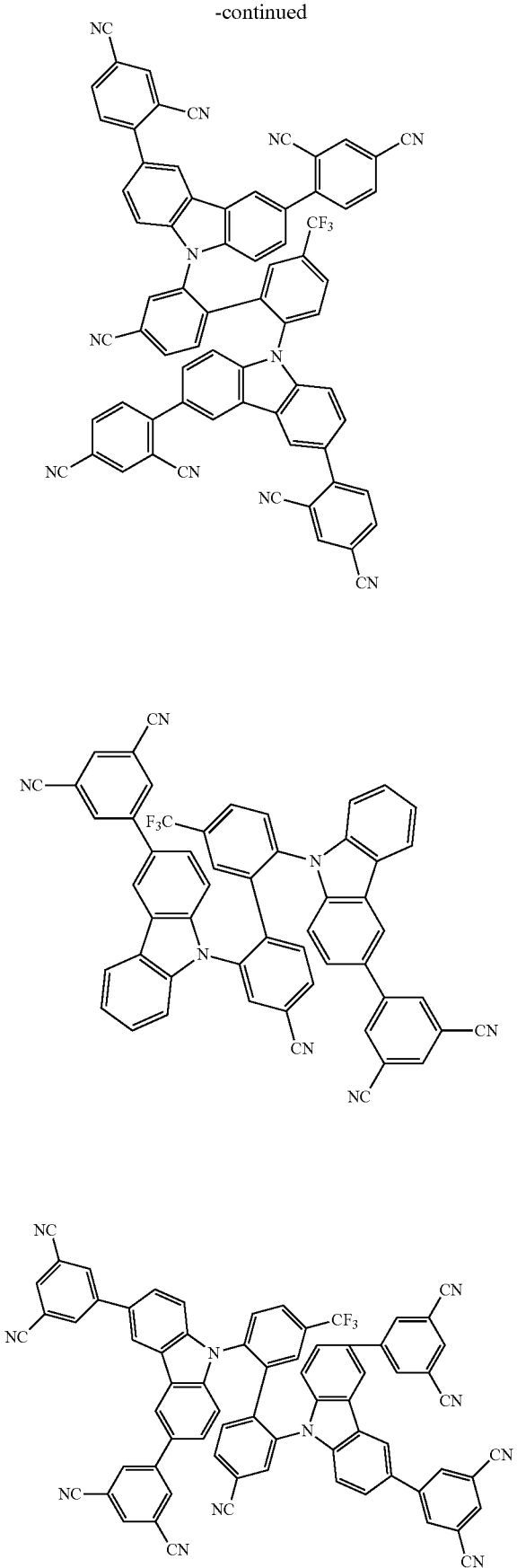
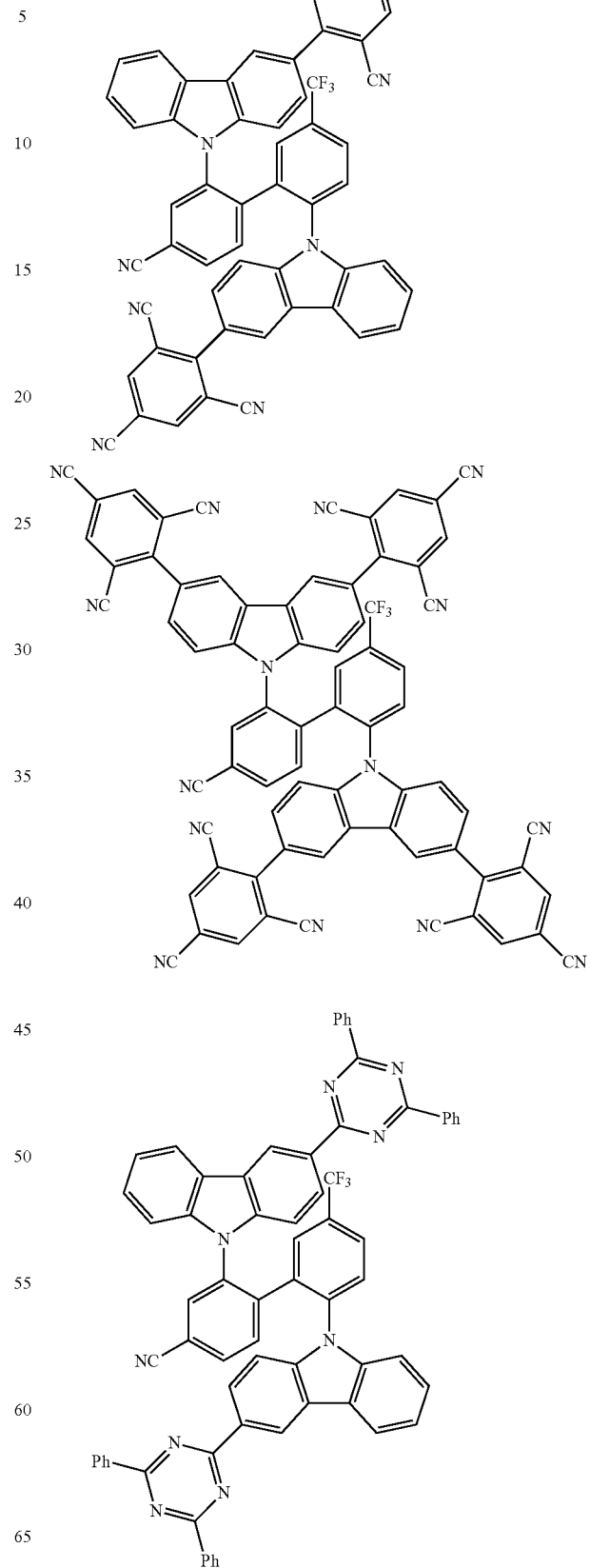

73
-continued
74
-continued
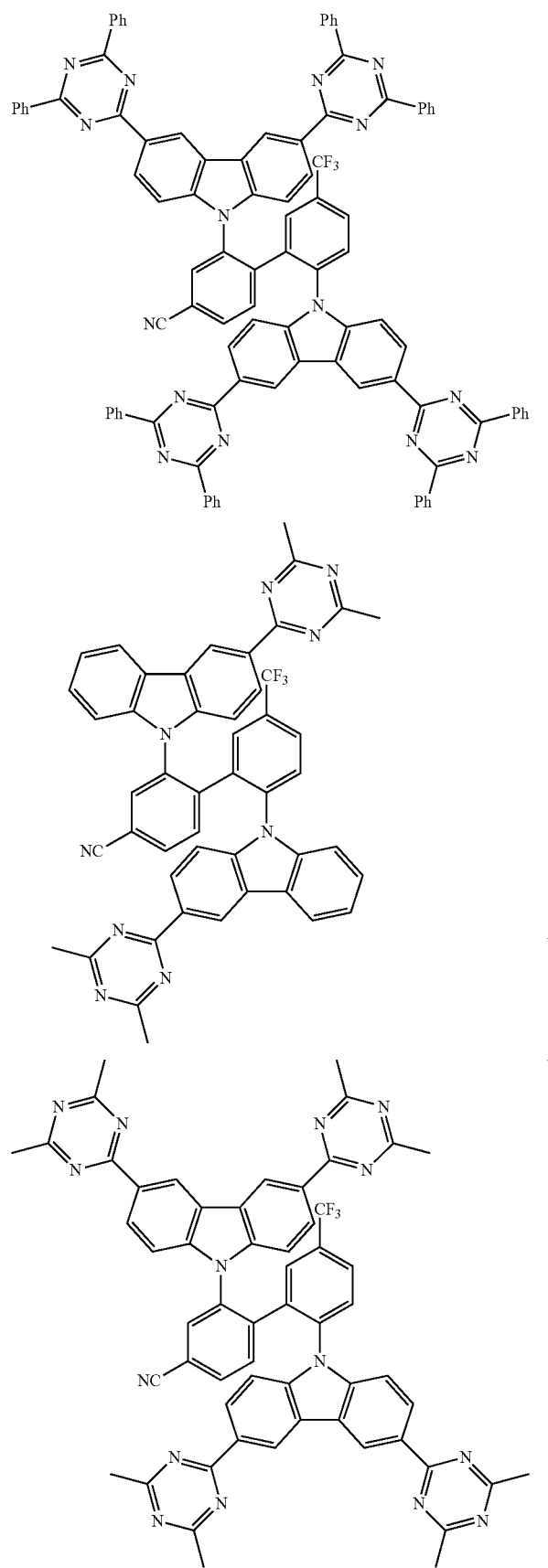
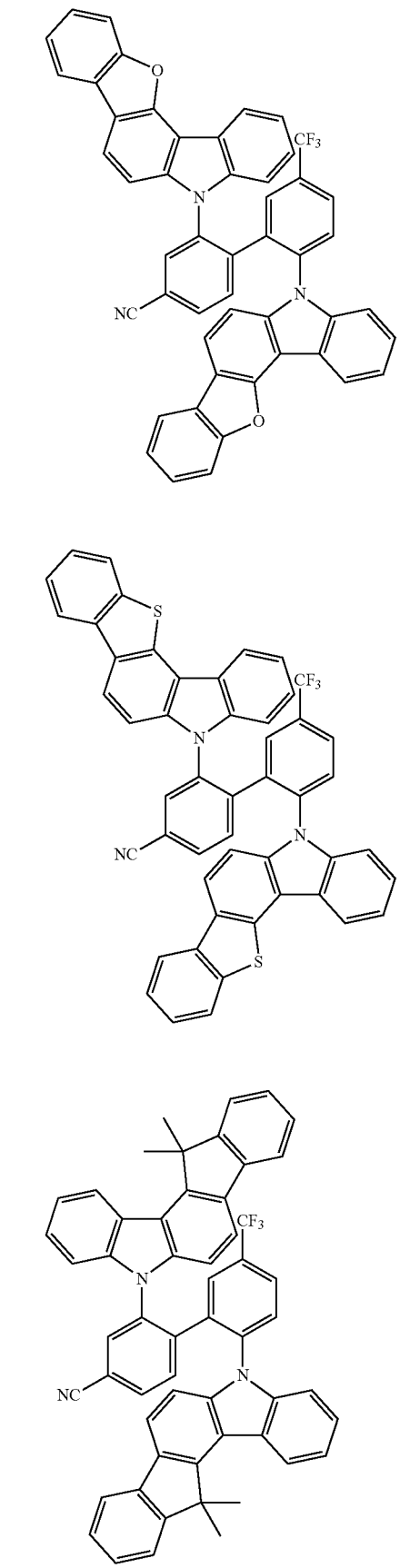 [SMILES: N#Cc1ccc(-n2c3ccccc3c3c4oc5ccccc5c4ccc32)c(-c2ccc(C(F)(F)F)cc2-n2c3ccccc3c3c4oc5ccccc5c4ccc32)c1 ; N#Cc1ccc(-n2c3ccccc3c3c4sc5ccccc5c4ccc32)c(-c2ccc(C(F)(F)F)cc2-n2c3ccccc3c3c4sc5ccccc5c4ccc32)c1 ; CC1(C)c2ccccc2-c2ccc3c(c21)c1ccccc1n3-c1ccc(C#N)cc1-c1ccc(C(F)(F)F)cc1-n1c2ccccc2c2c3c(ccc21)-c1ccccc1C3(C)C]

75
-continued
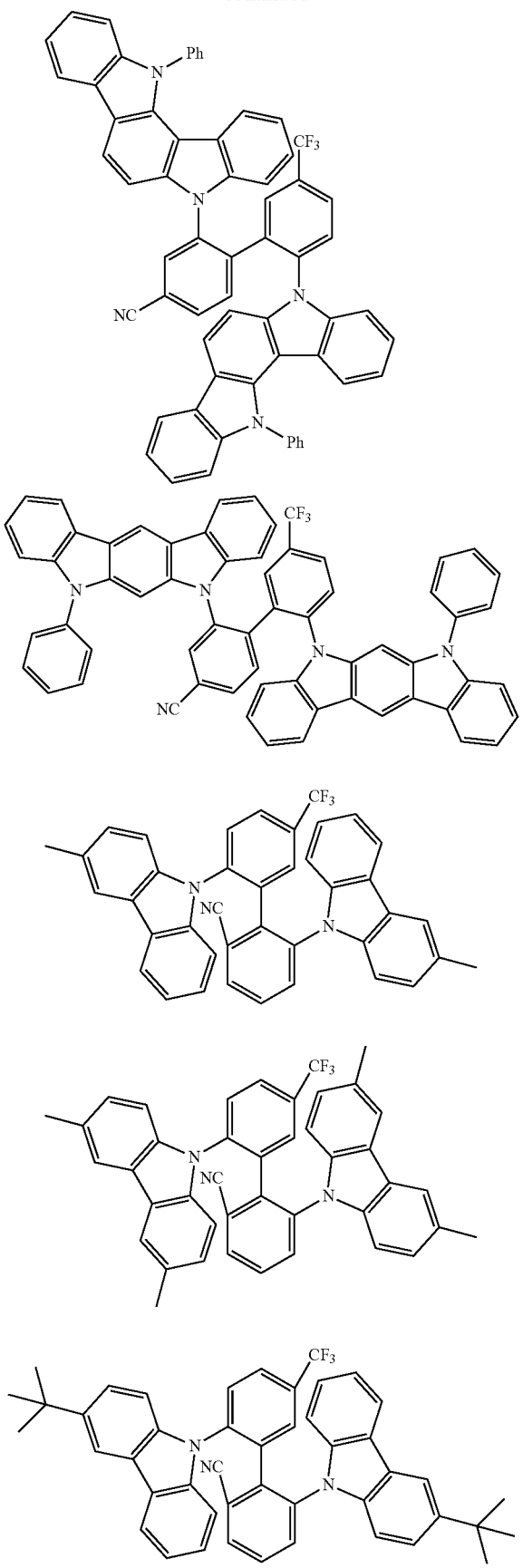
76
-continued
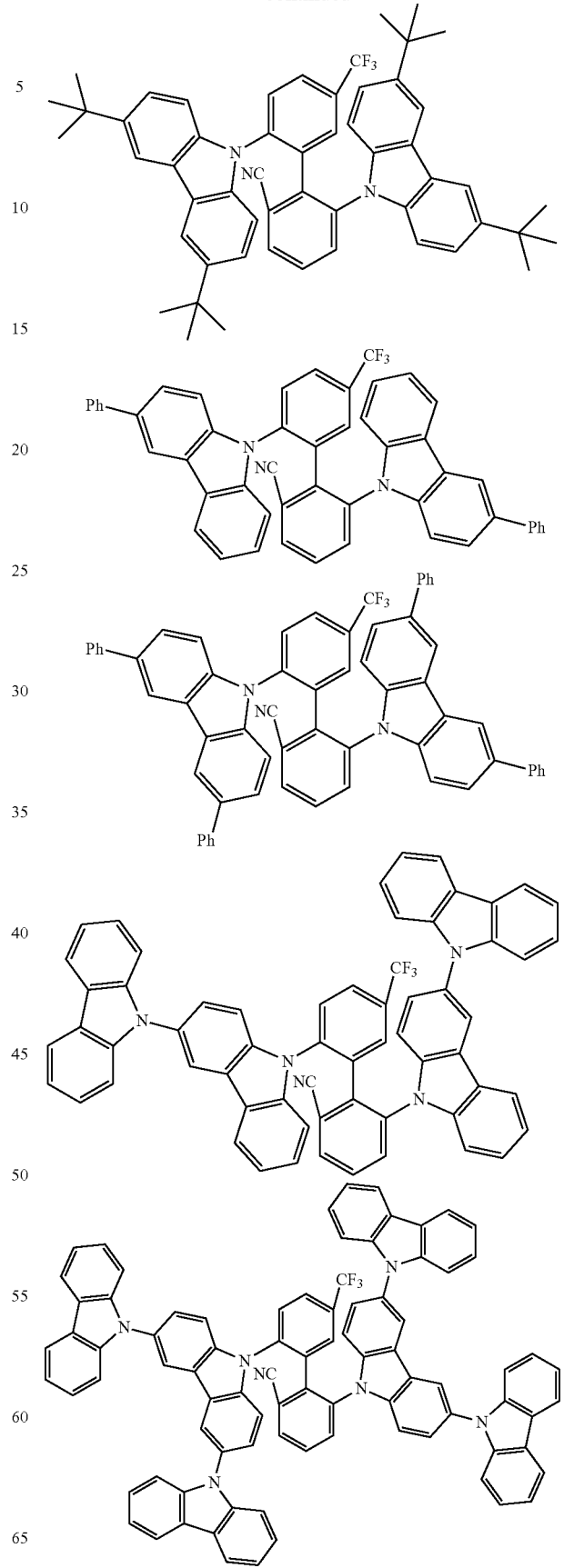

77
-continued
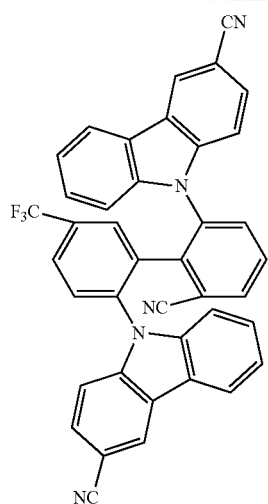
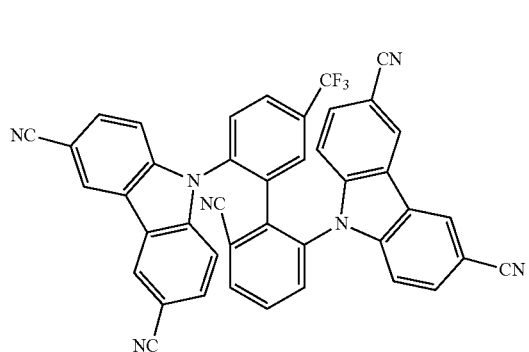
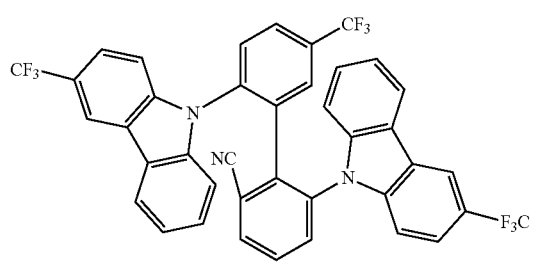
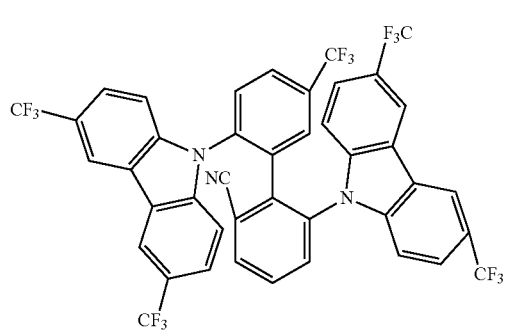
78
-continued
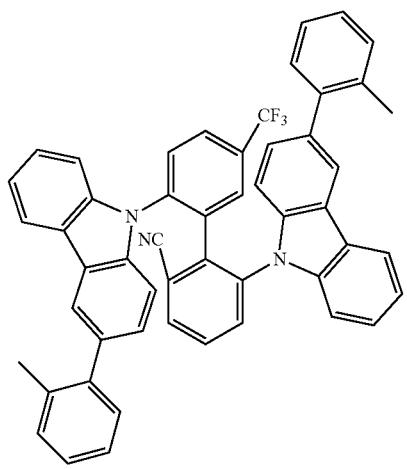
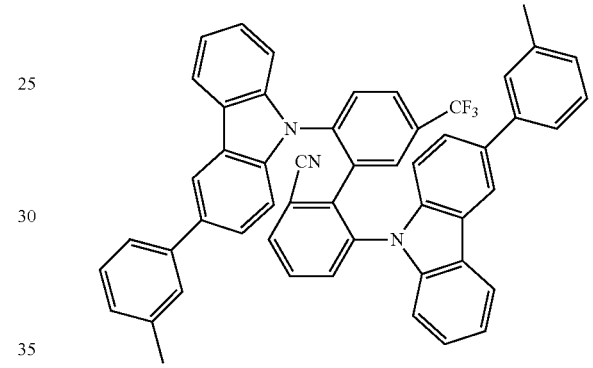
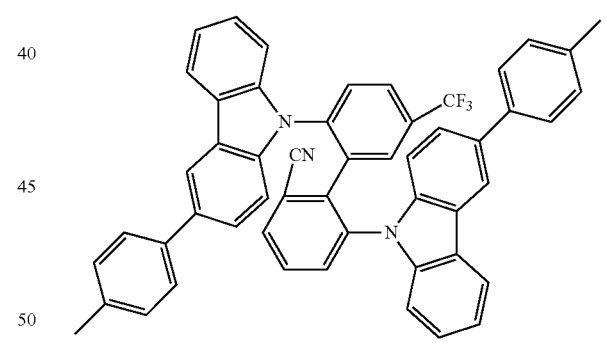
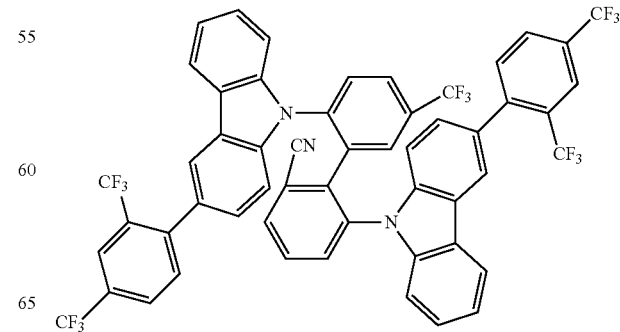

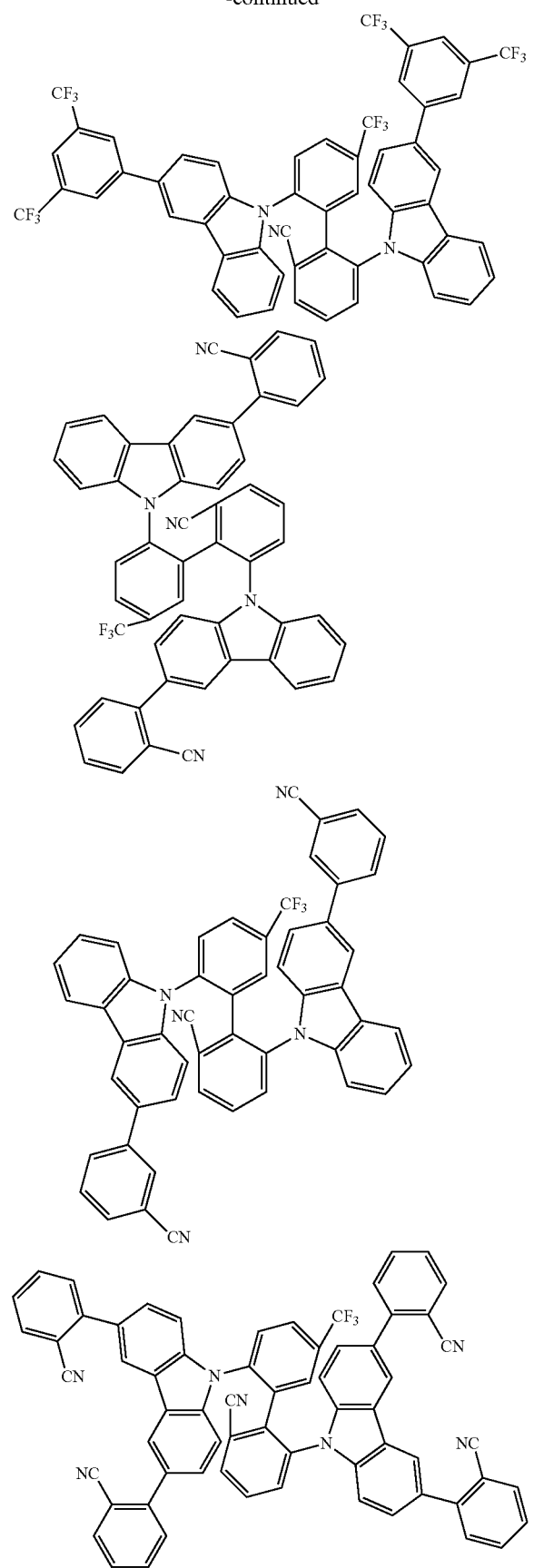
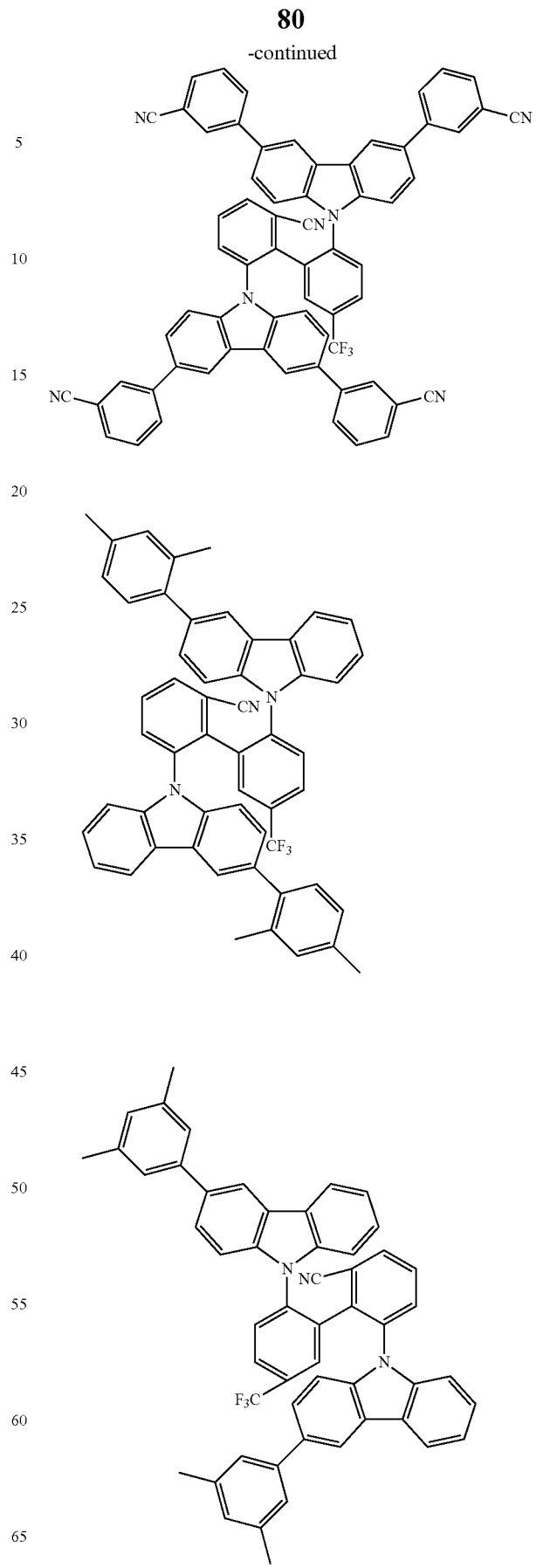

81
-continued
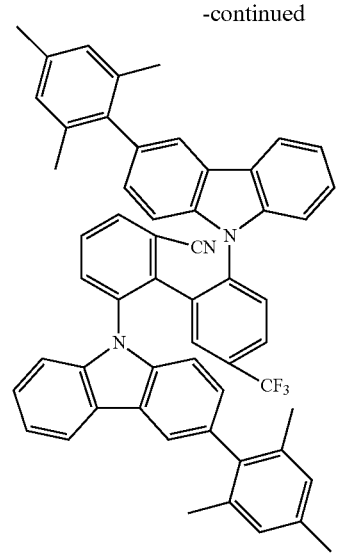
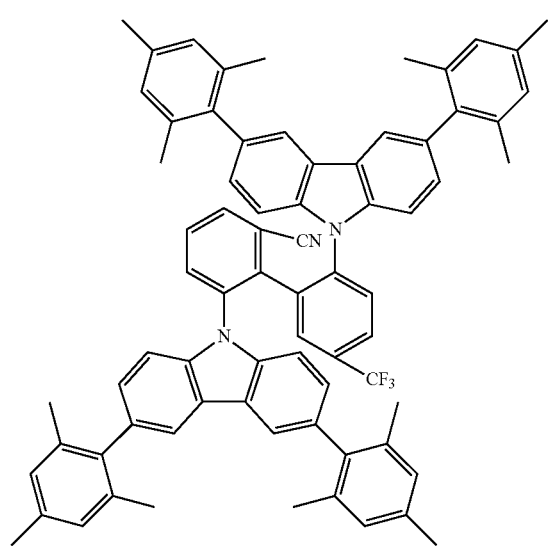
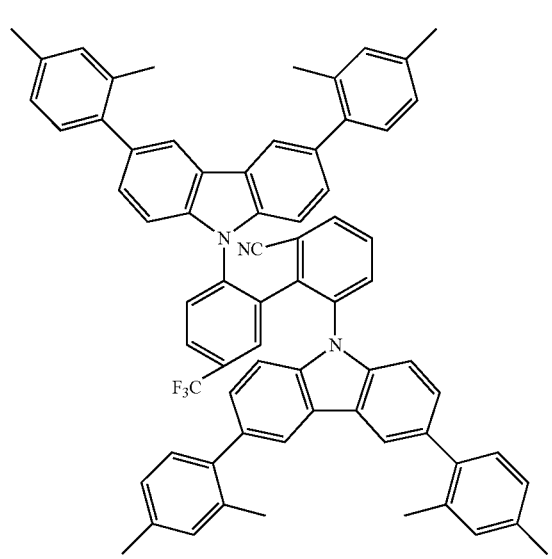
82
-continued
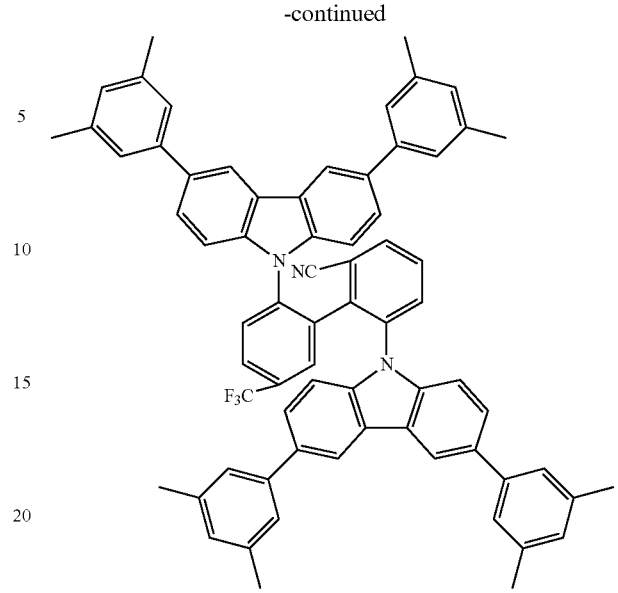
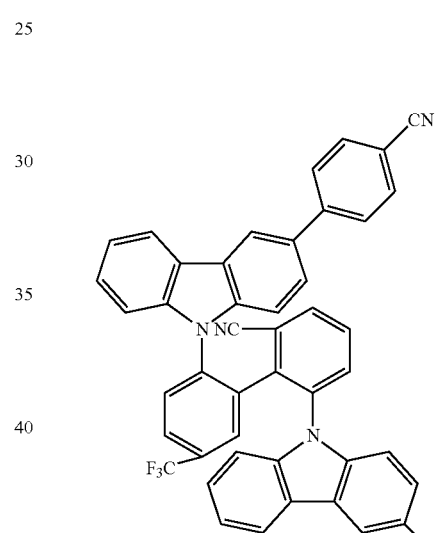
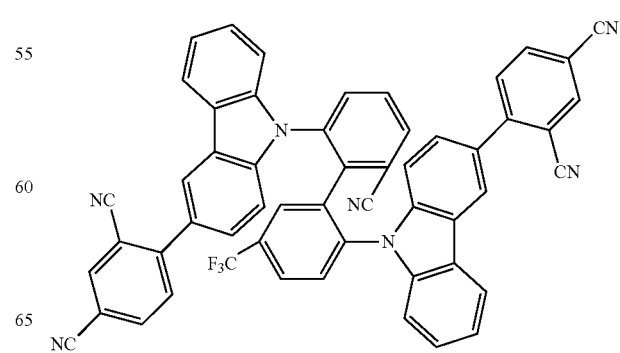

83
-continued
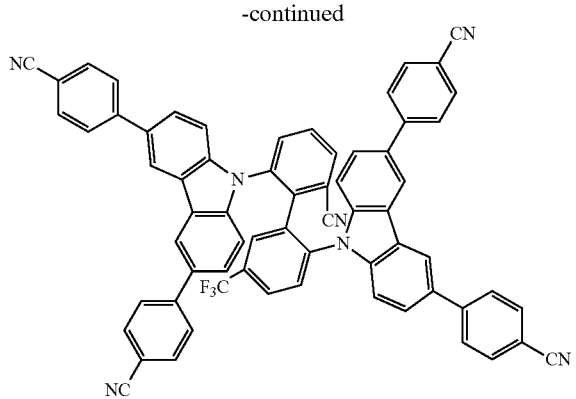
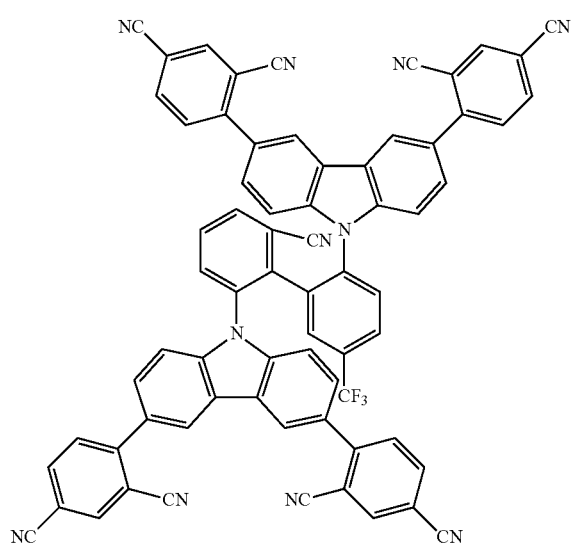
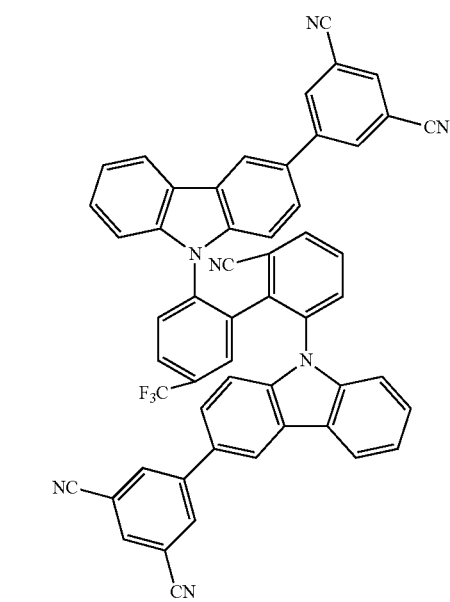
84
-continued
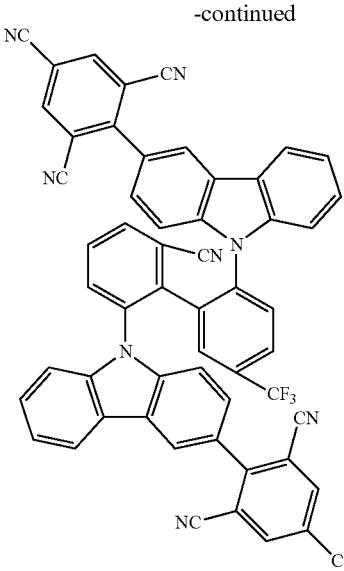
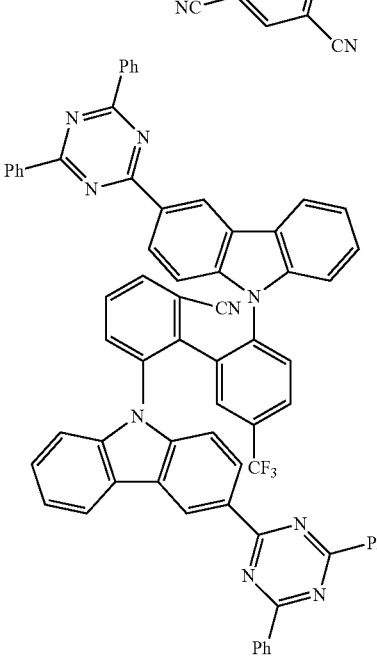
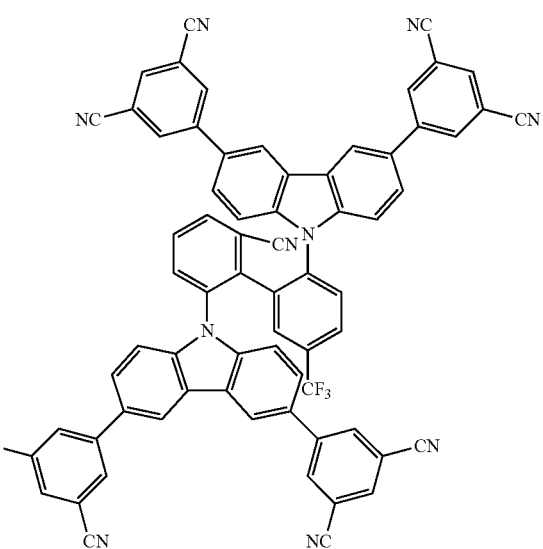

85
-continued
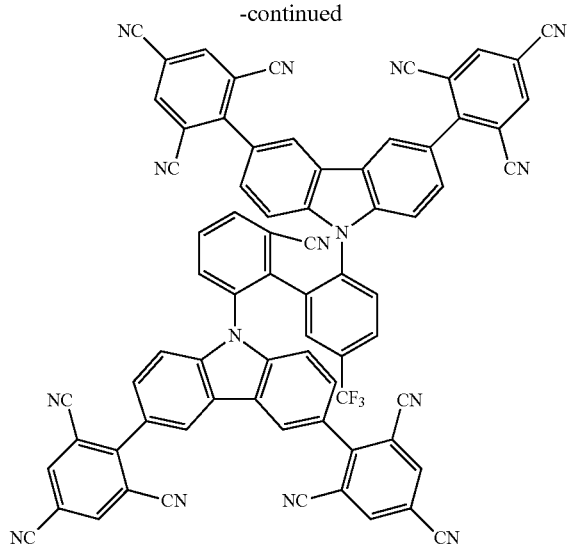
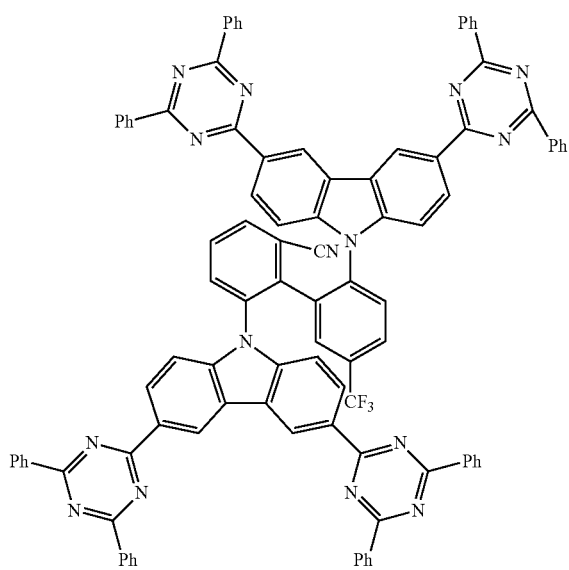
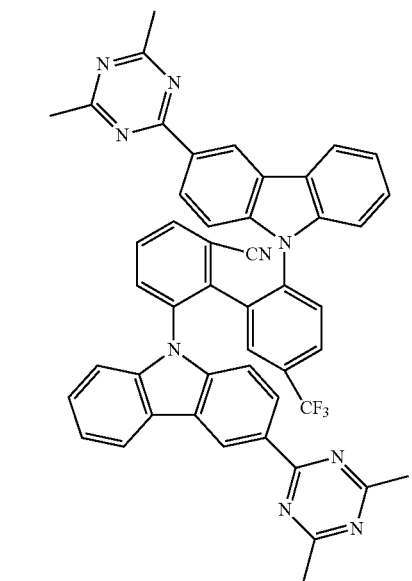
86
-continued
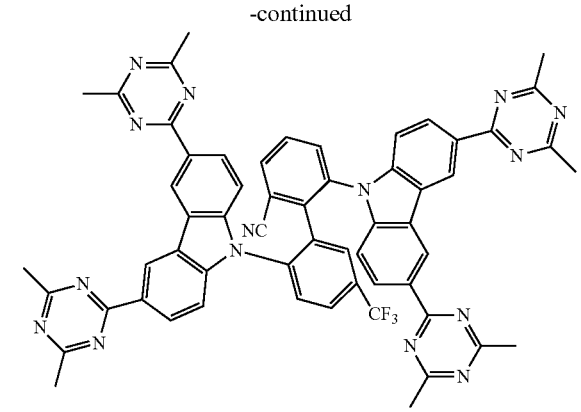
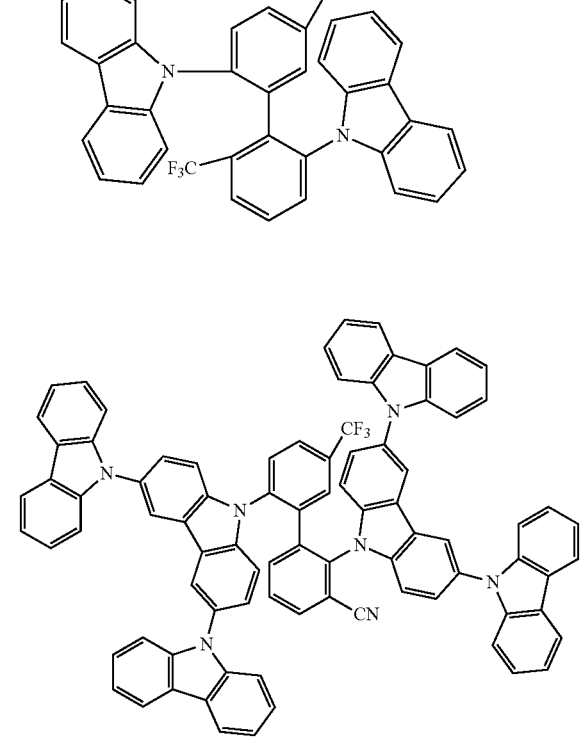

-continued
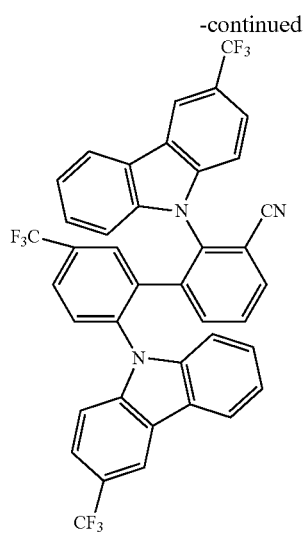
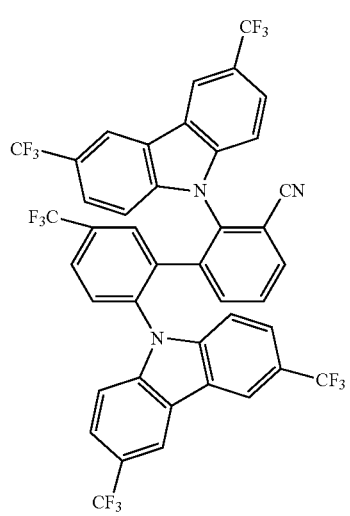
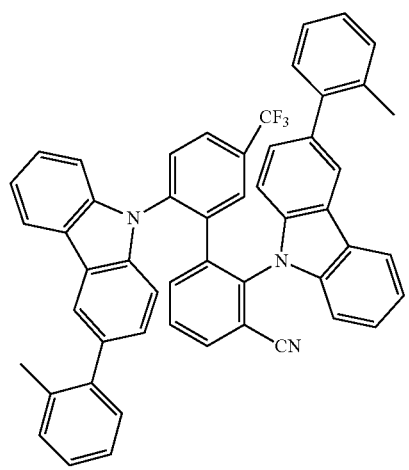
-continued
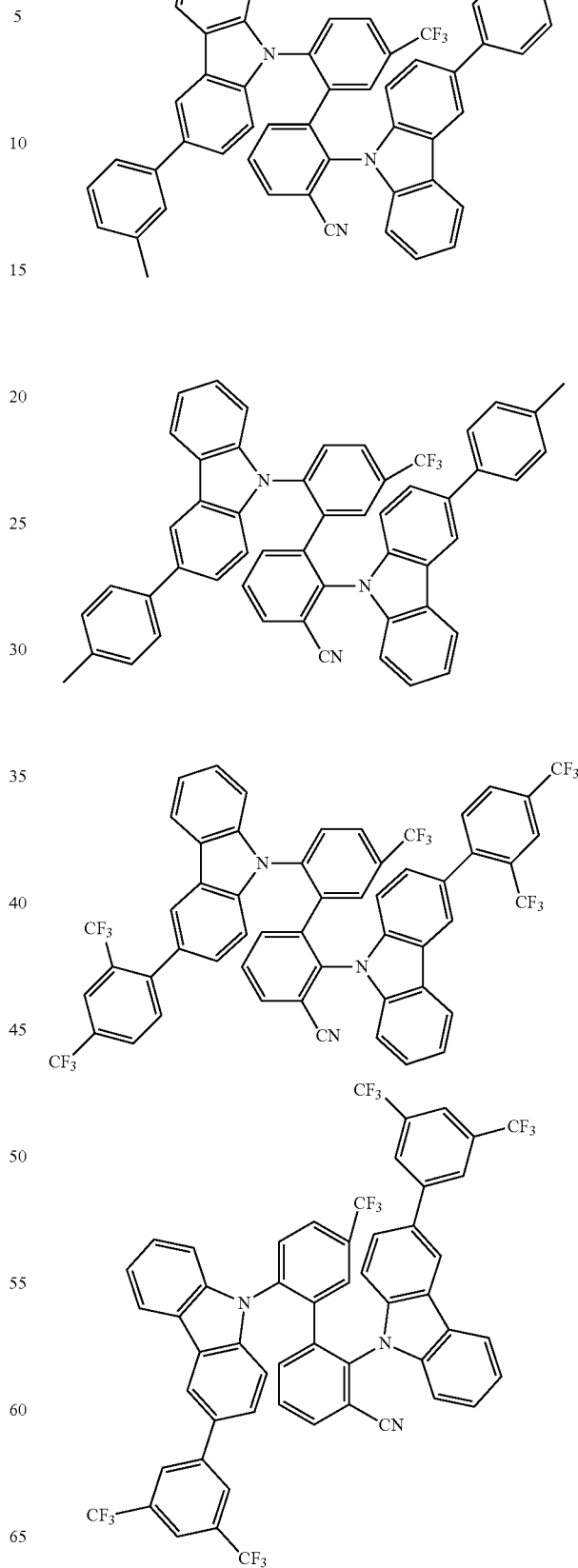

89
-continued
90
-continued
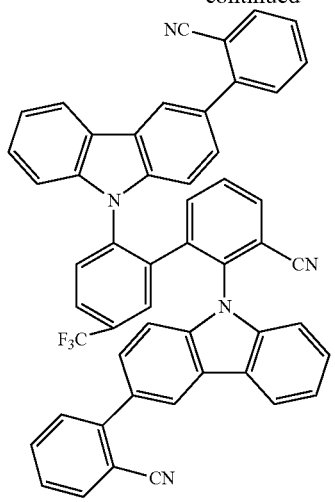
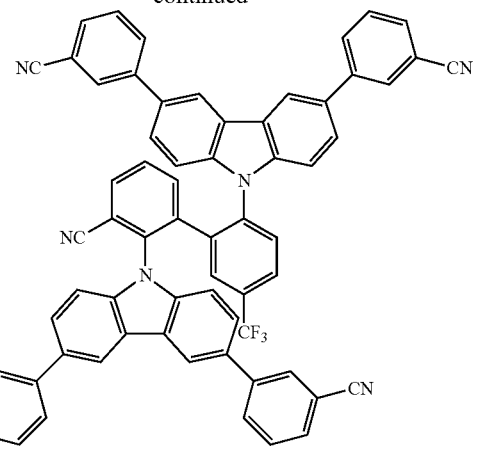
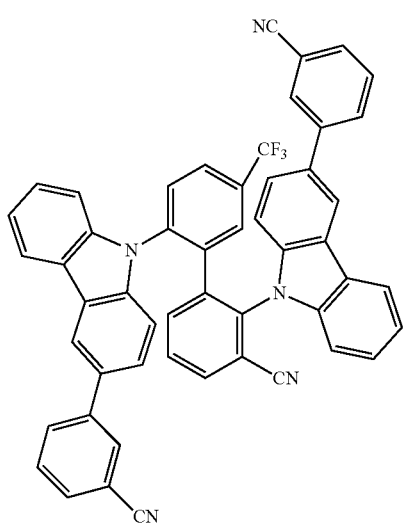
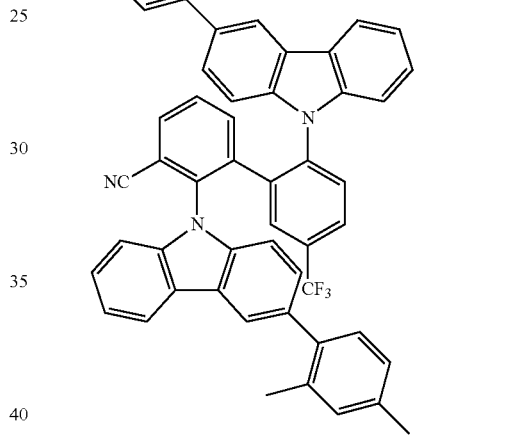
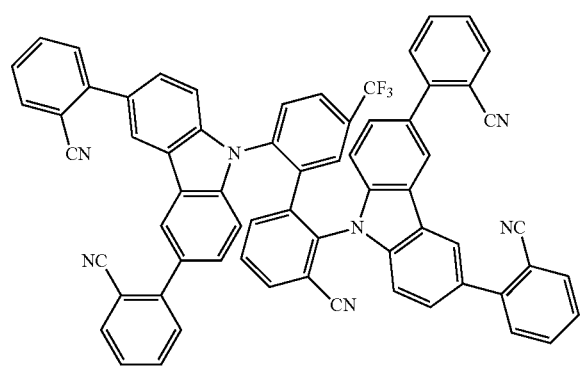
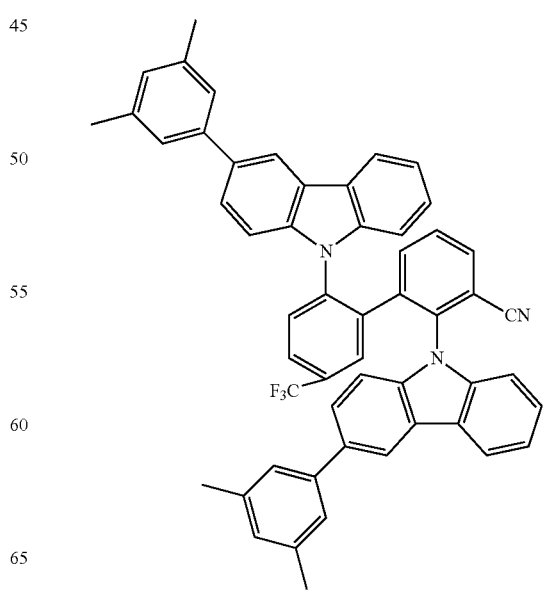

91
-continued
92
-continued
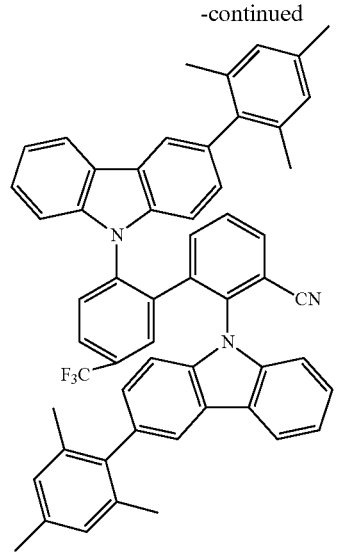
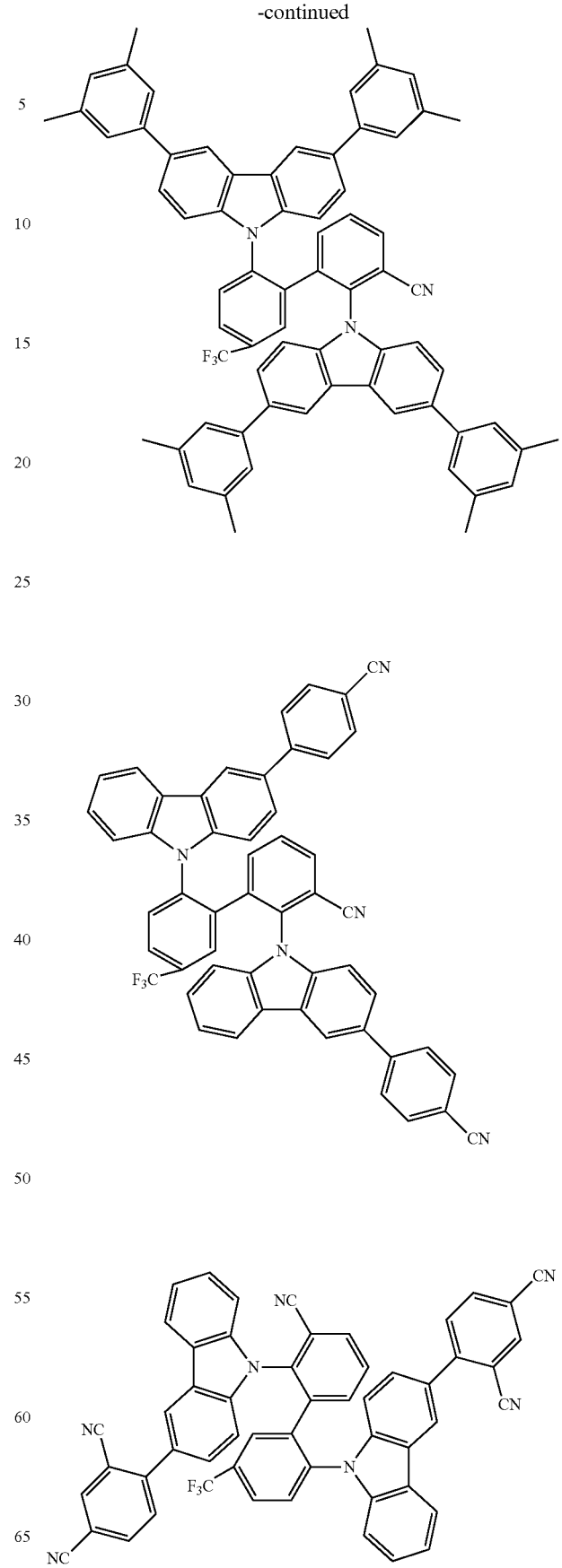

93
-continued
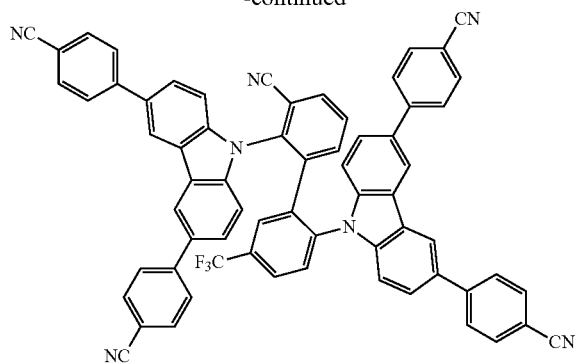
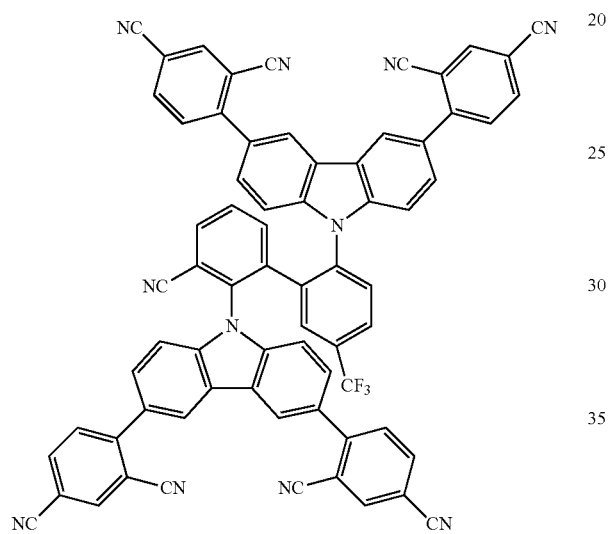
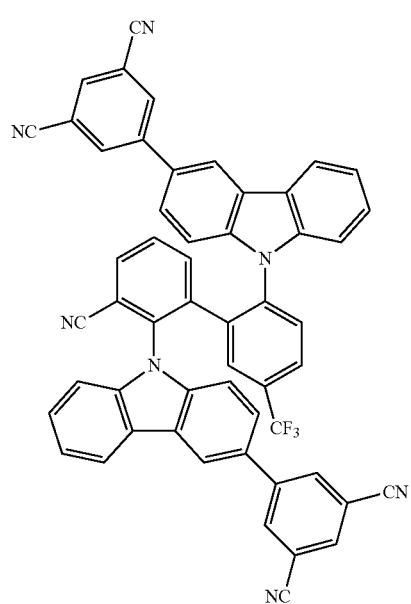
94
-continued
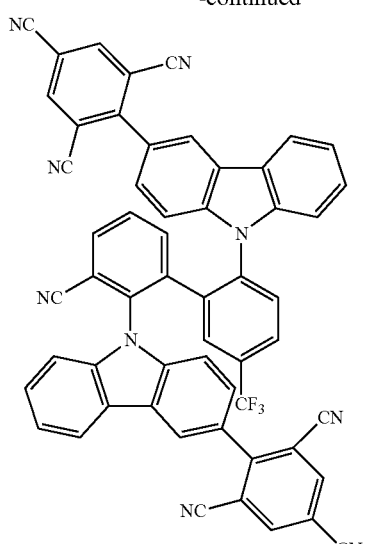
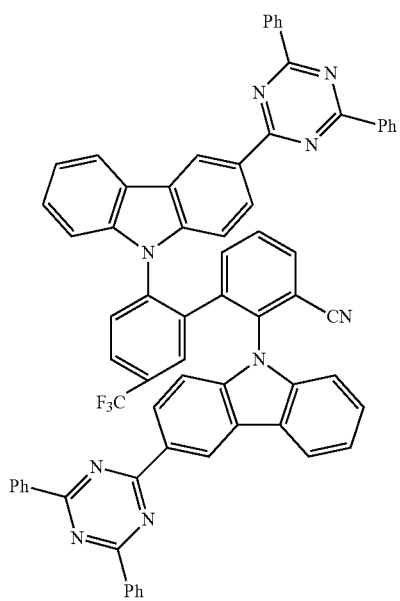
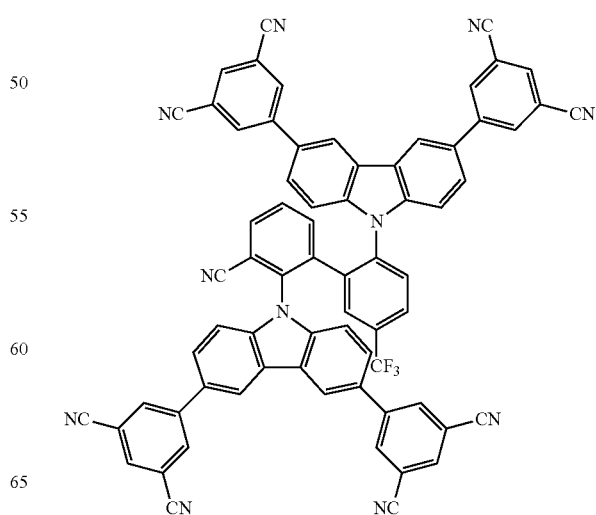

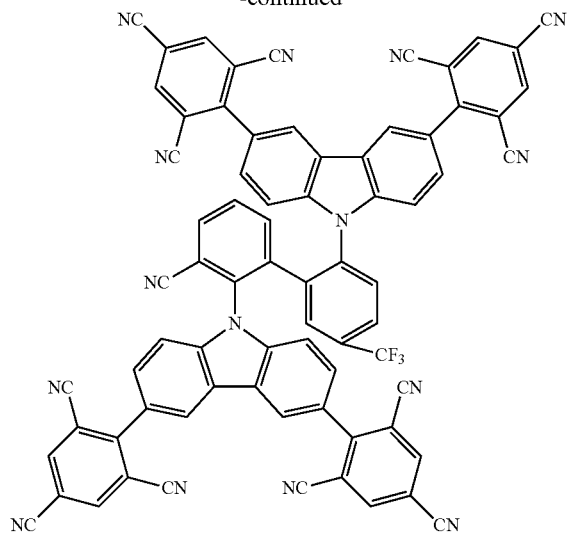
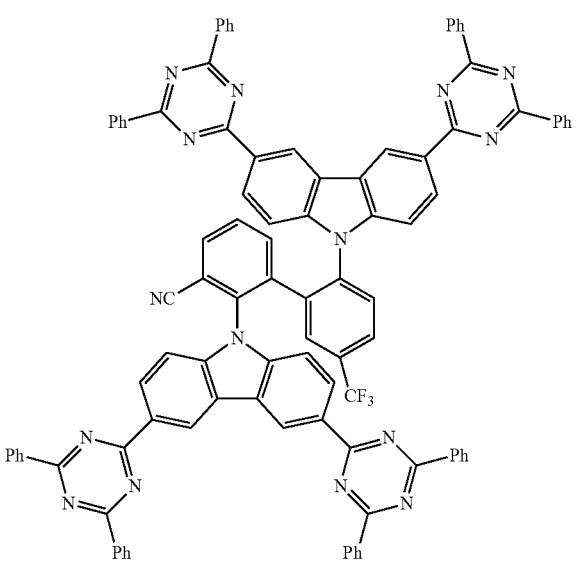
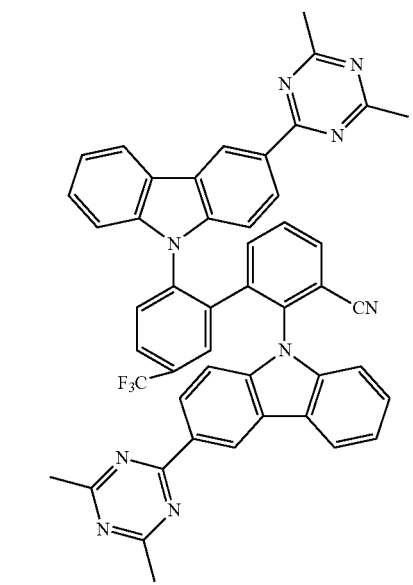
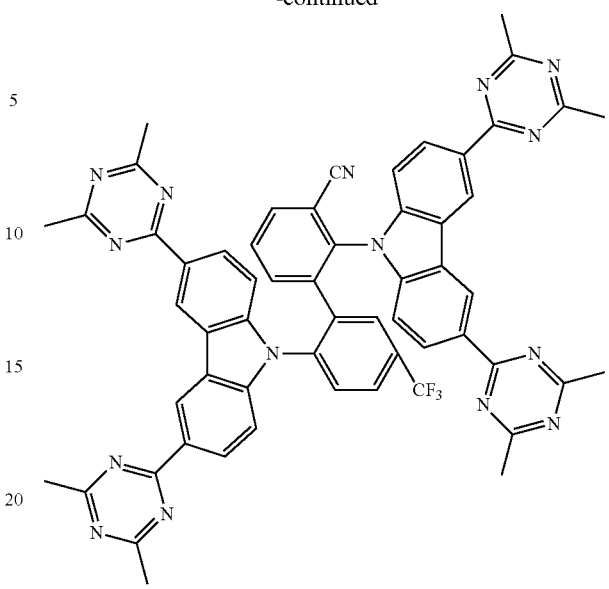
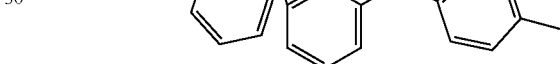
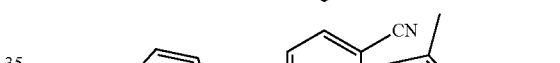
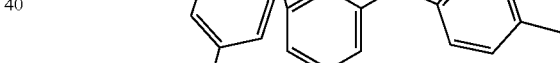
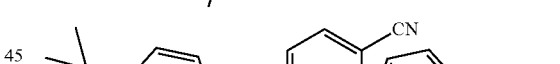
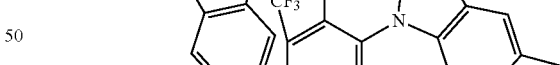
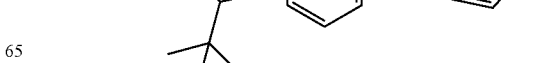

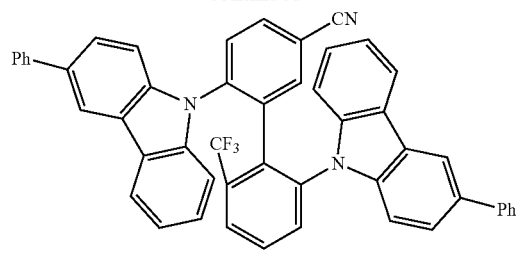
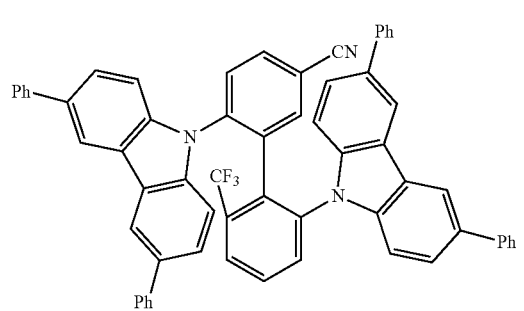
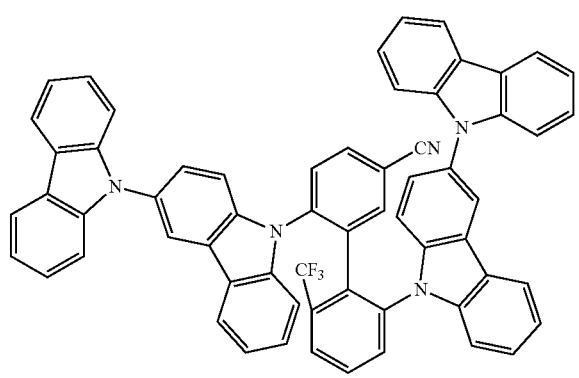
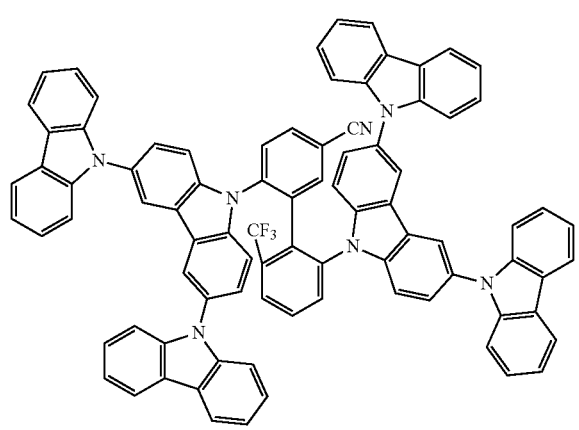
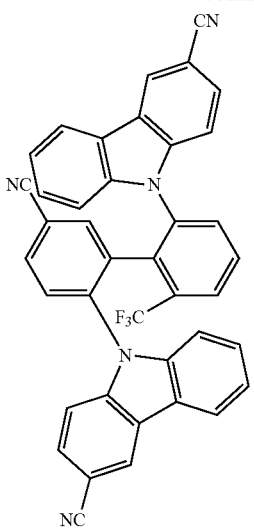
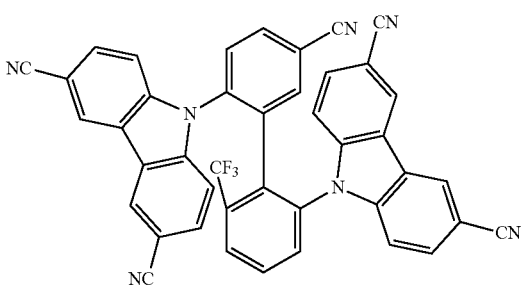
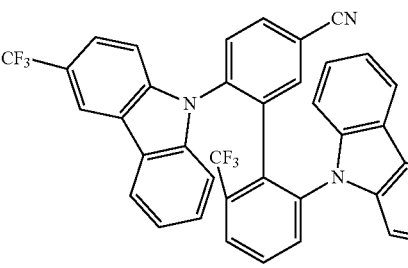
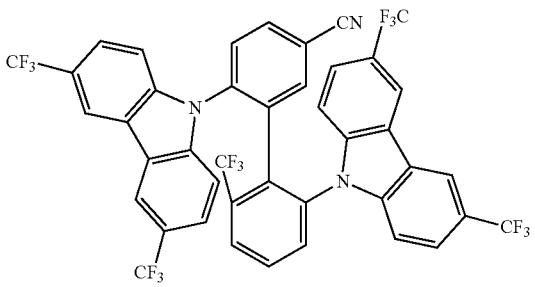

99
-continued
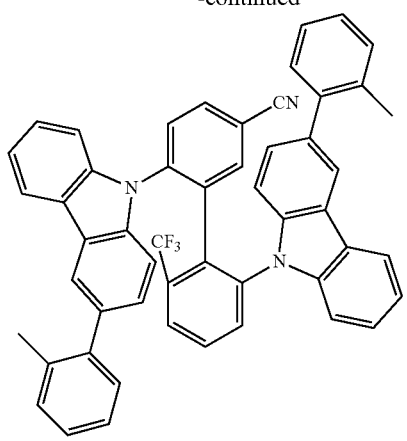
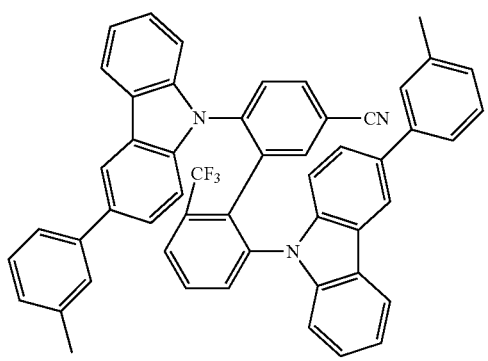
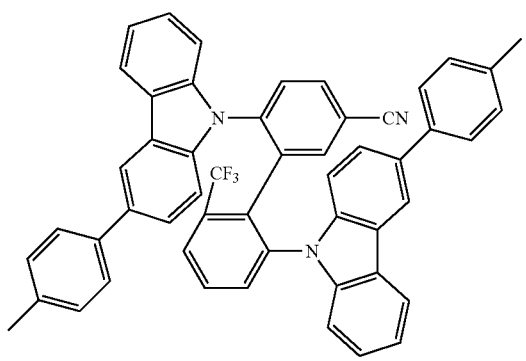
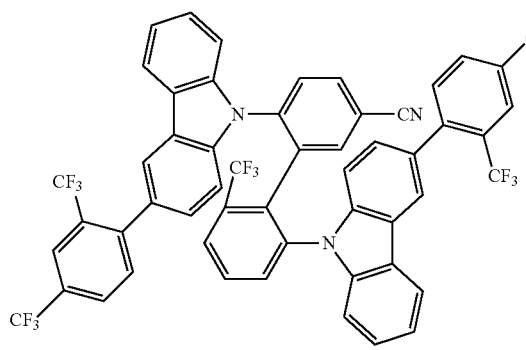
100
-continued
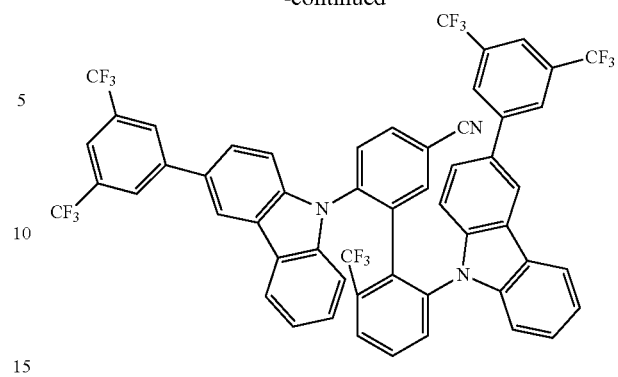
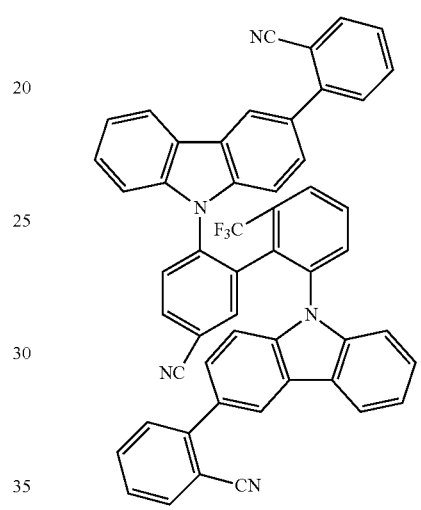
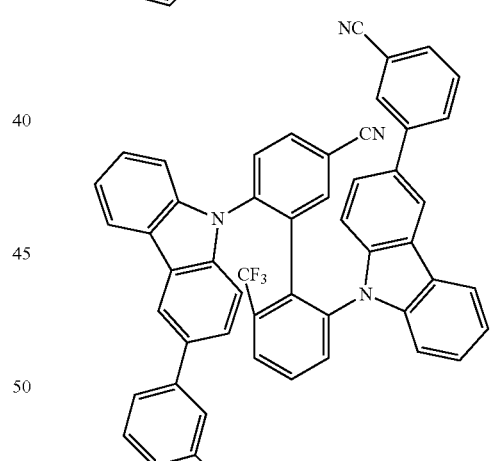
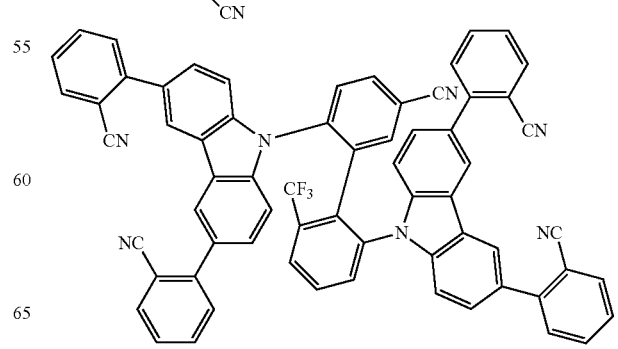

101
-continued
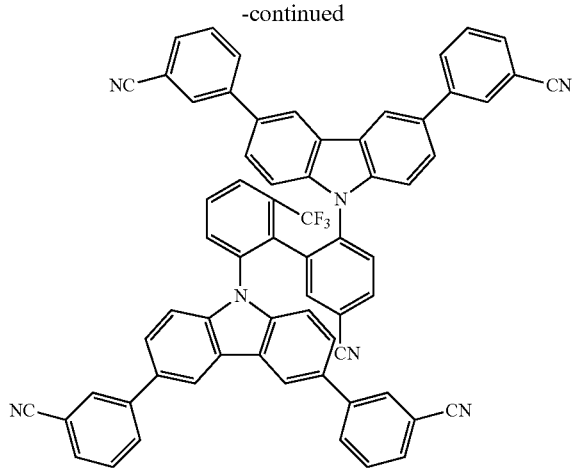
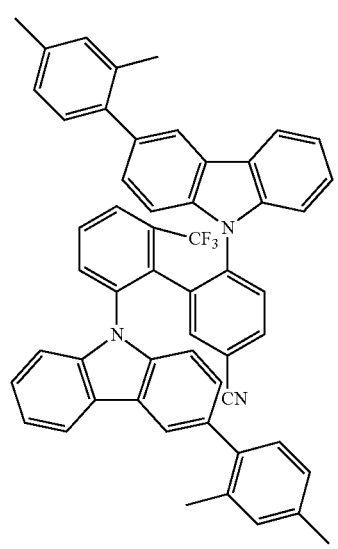
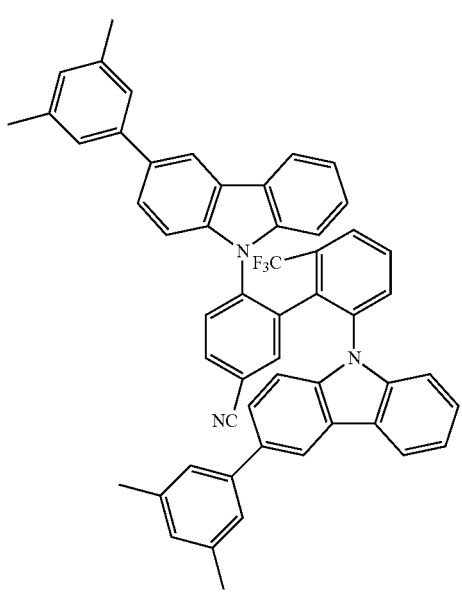
102
-continued
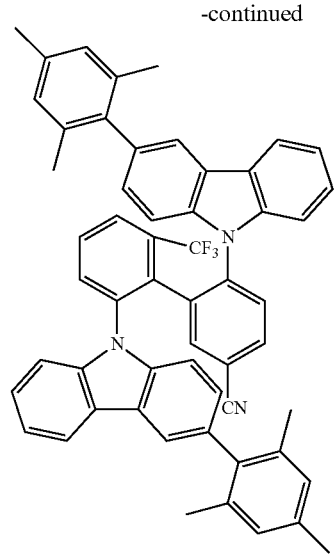
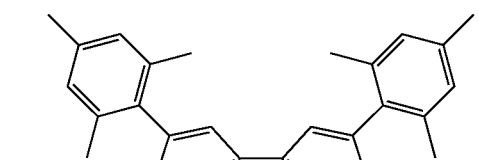
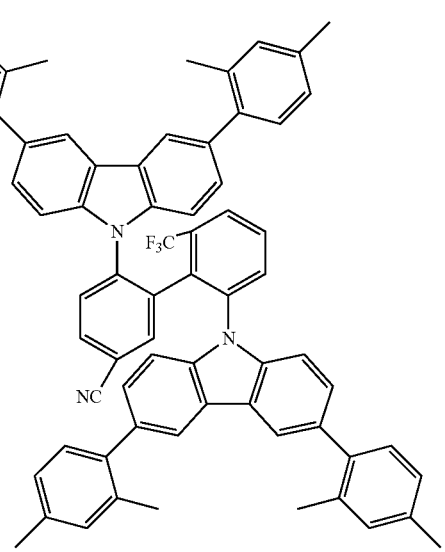

103
-continued
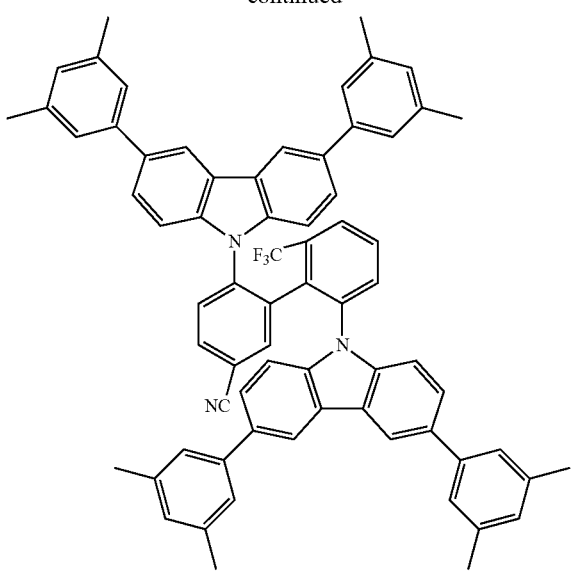
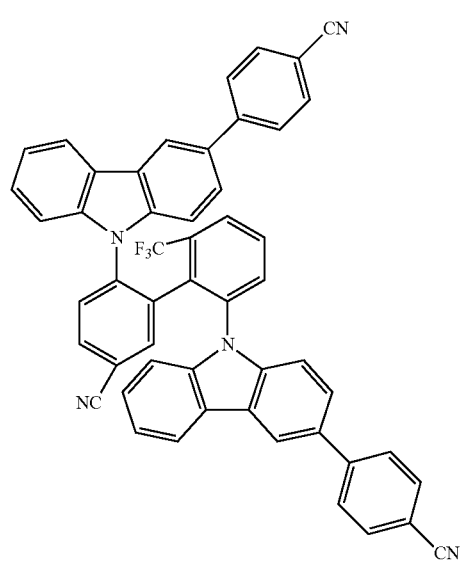
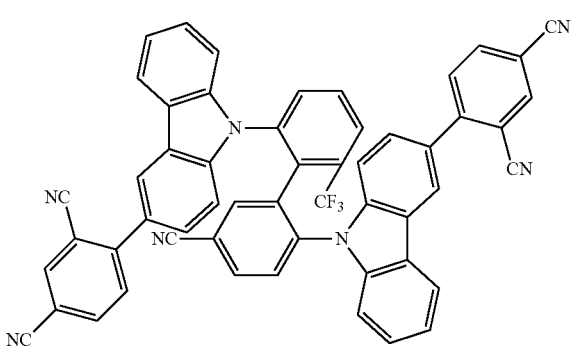
104
-continued
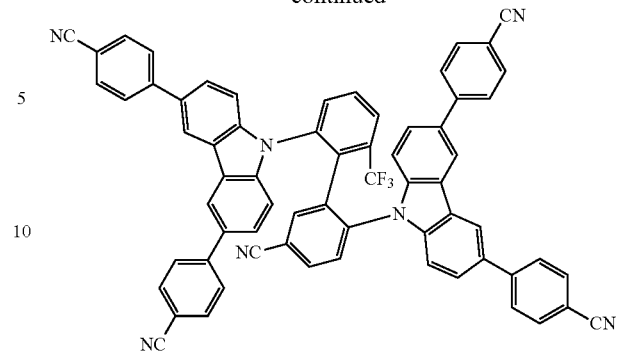
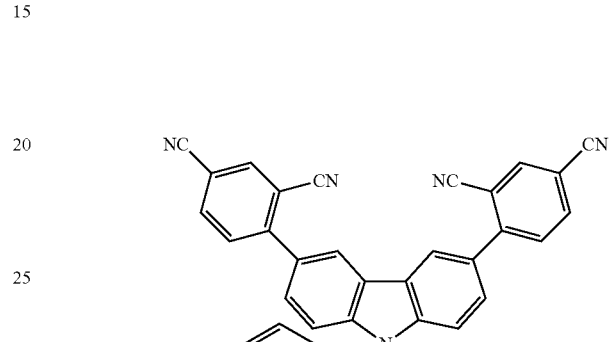
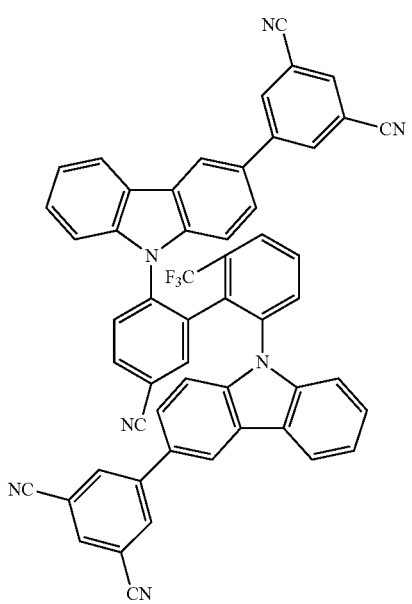

105
-continued
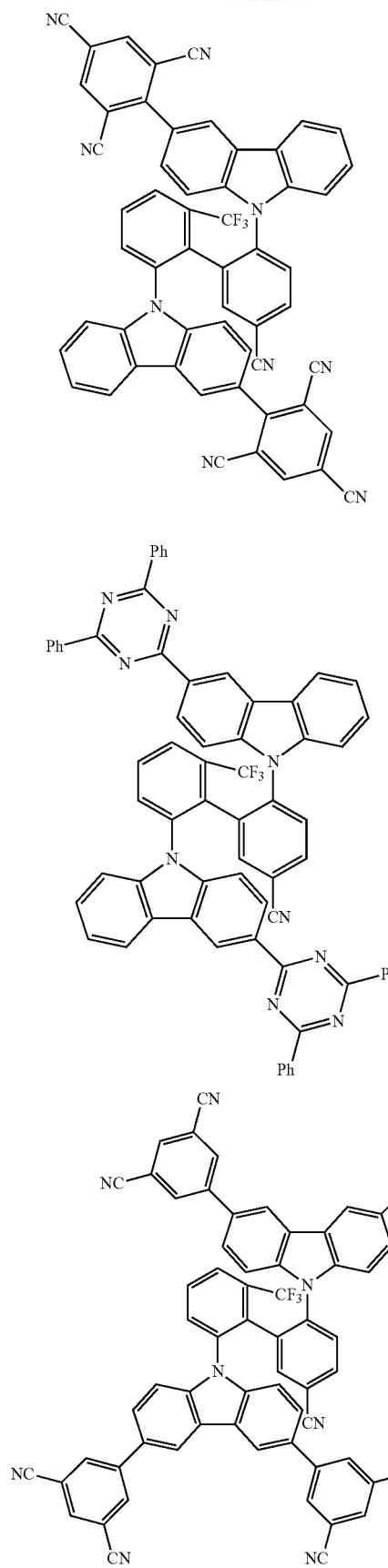
106
-continued
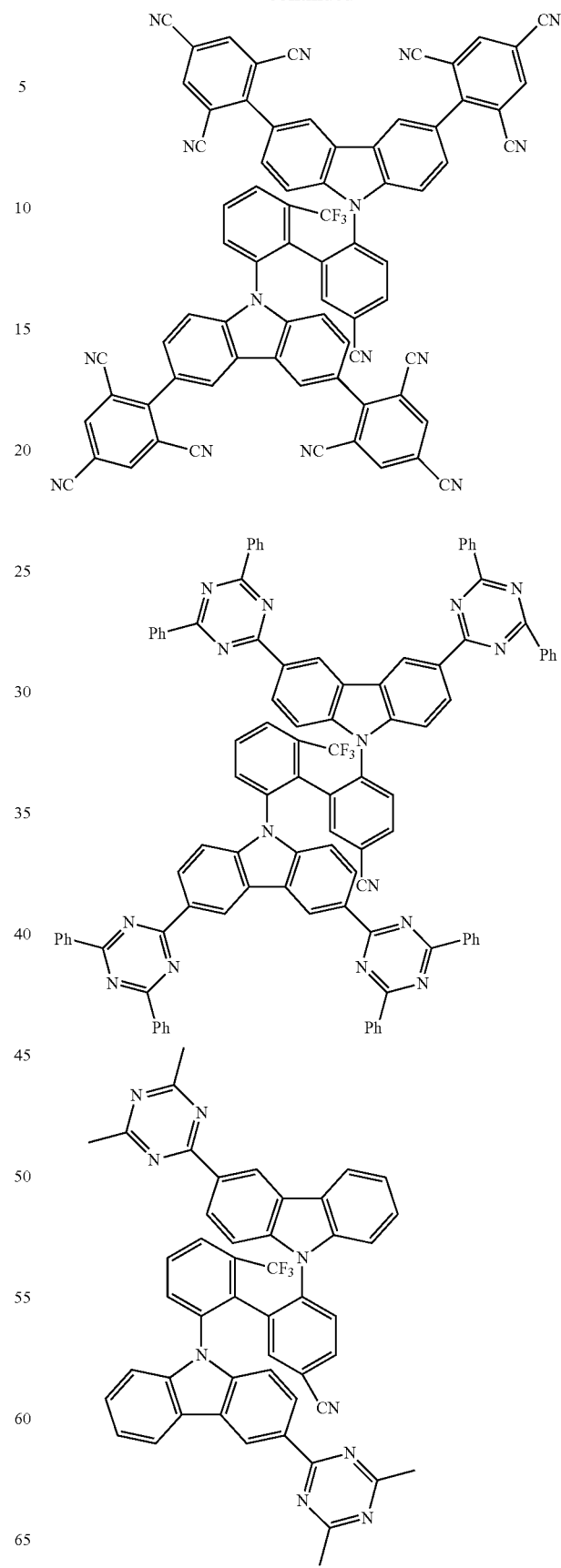

107
-continued
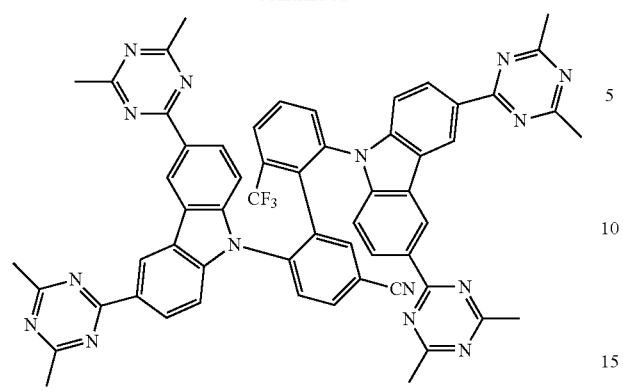
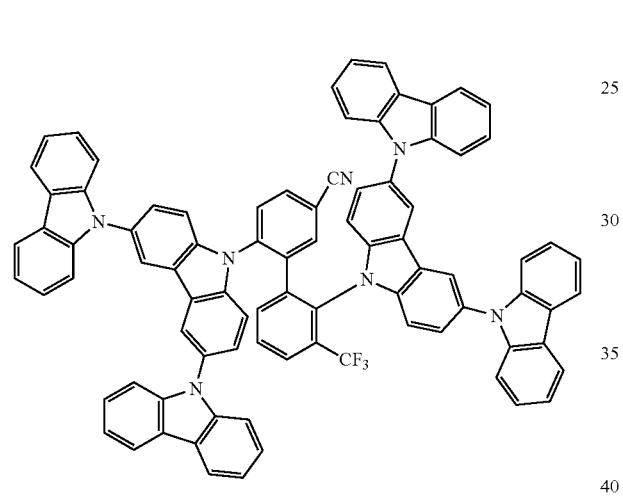
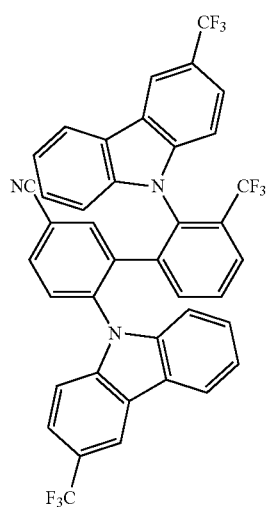
108
-continued
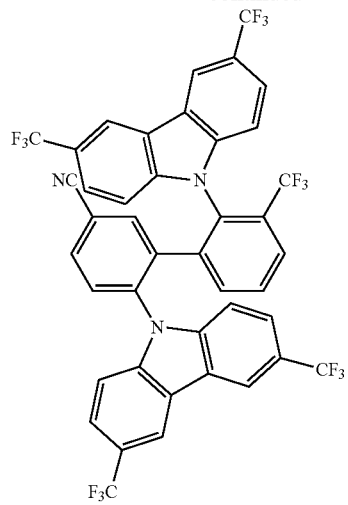
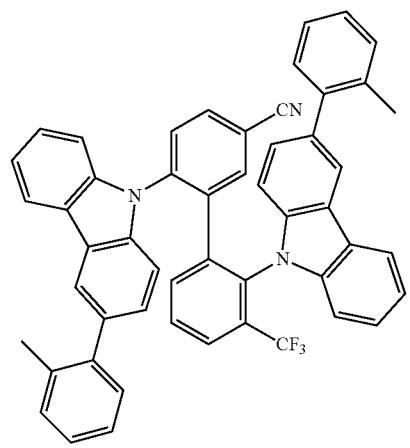
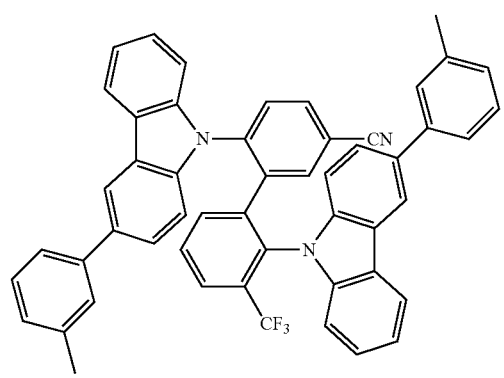
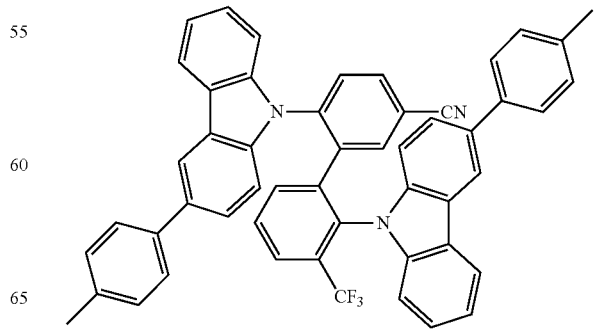

109
-continued
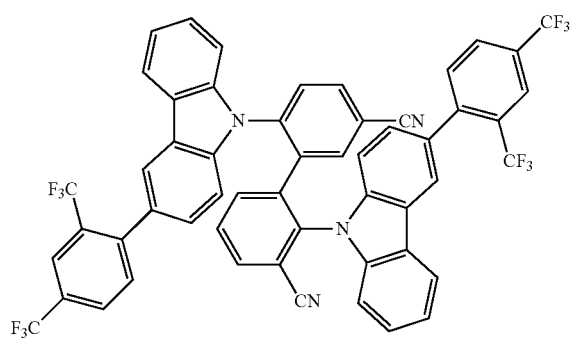
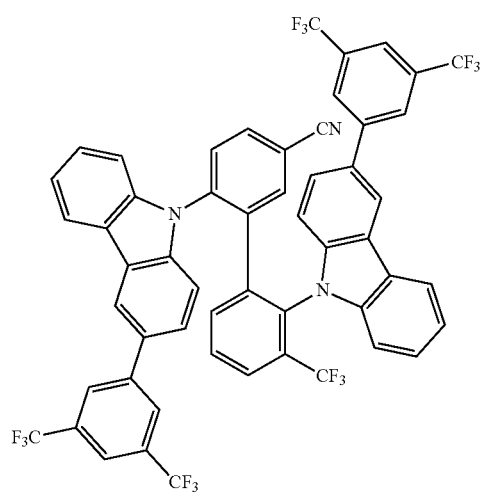
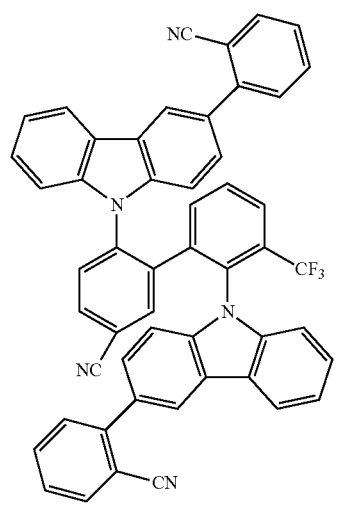
110
-continued
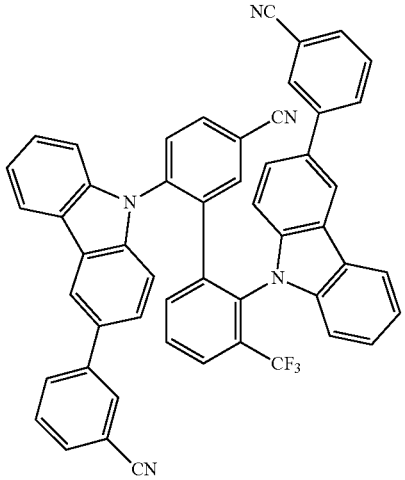
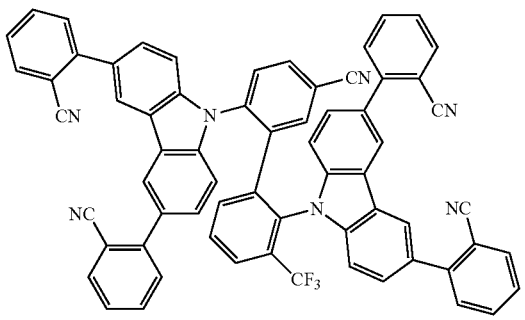
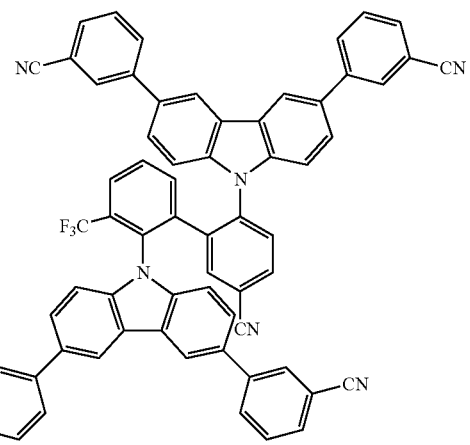

111
-continued
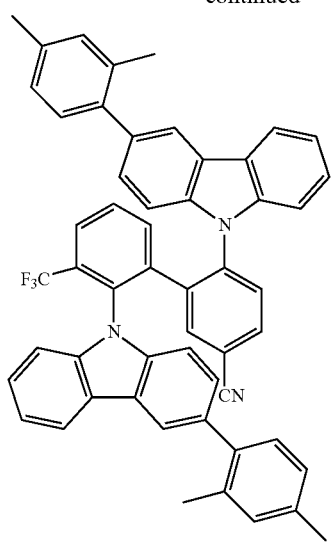
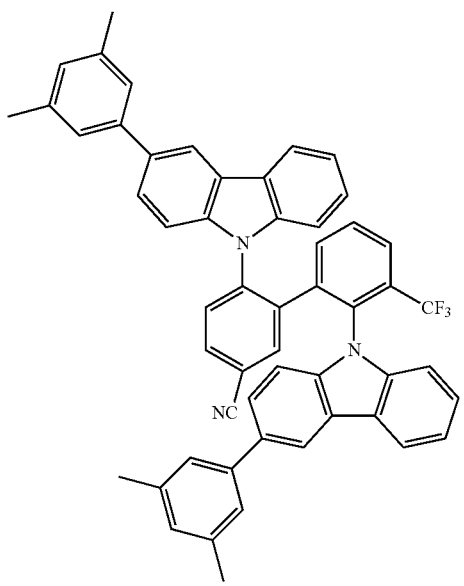
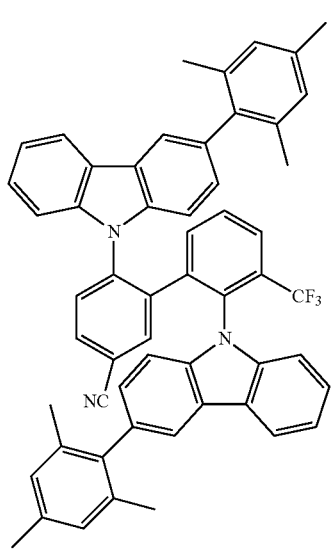
112
-continued
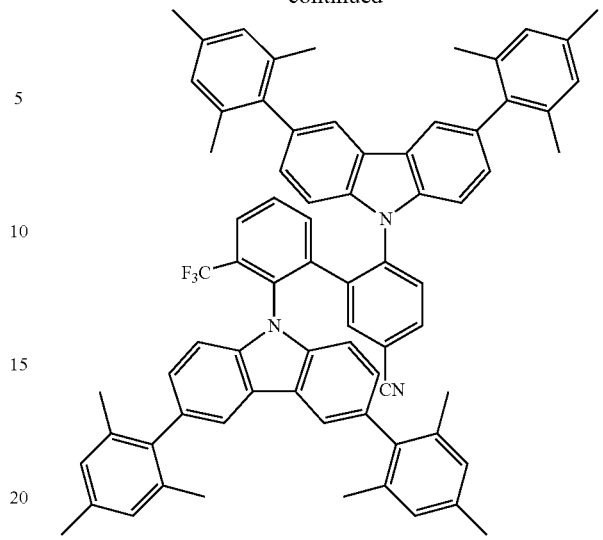
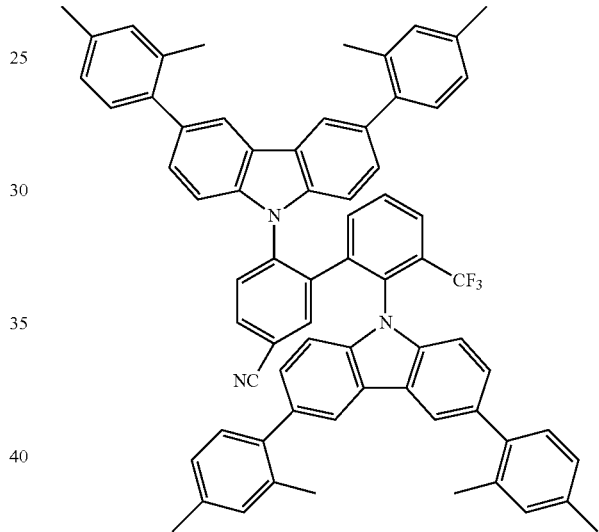
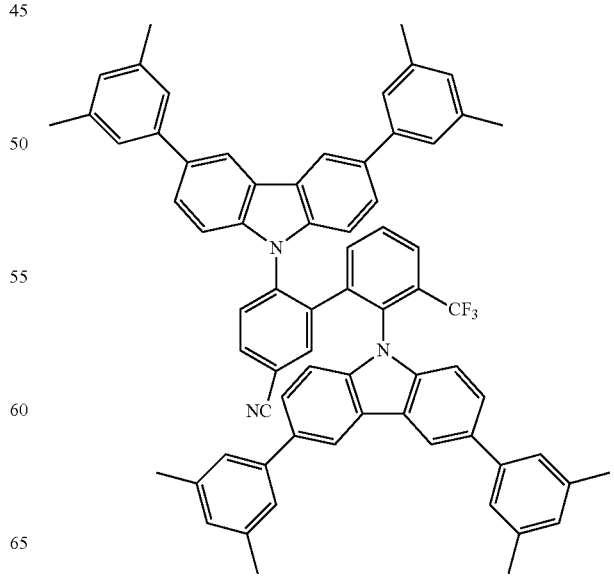

113
-continued
114
-continued
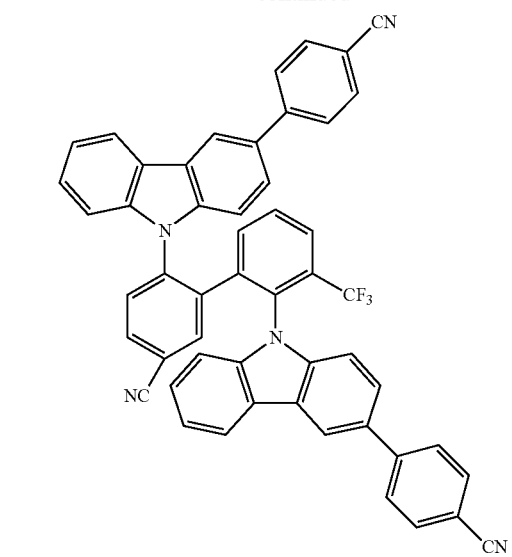
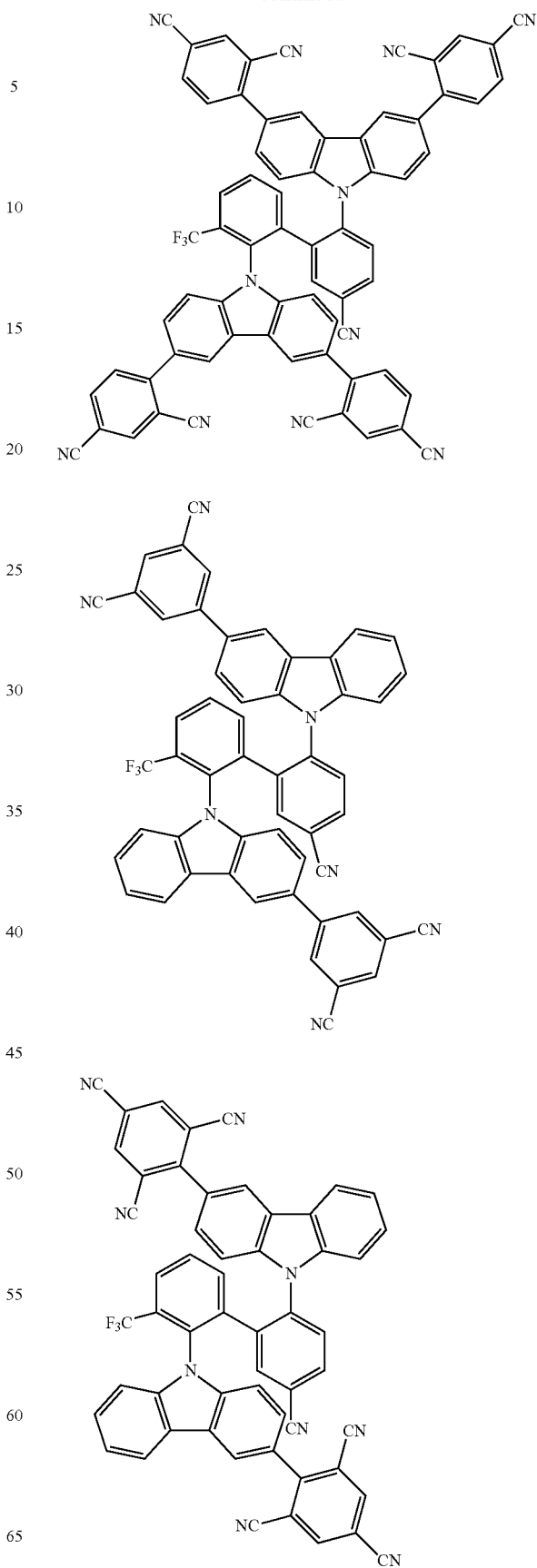

115
-continued
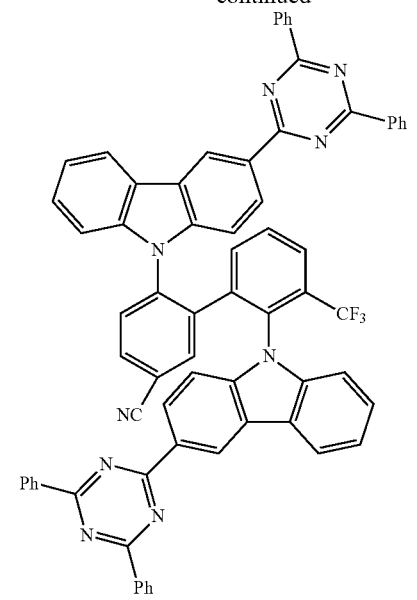
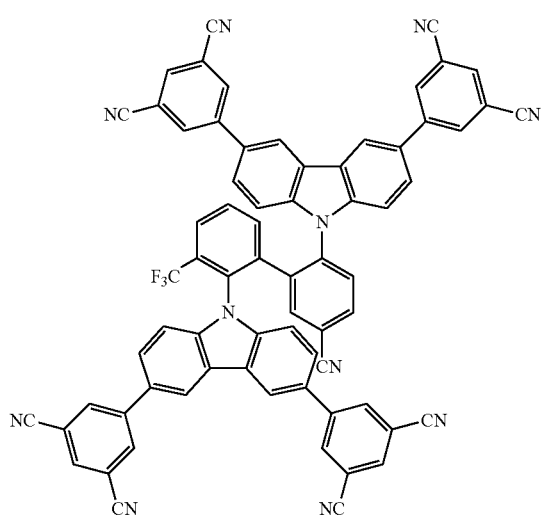
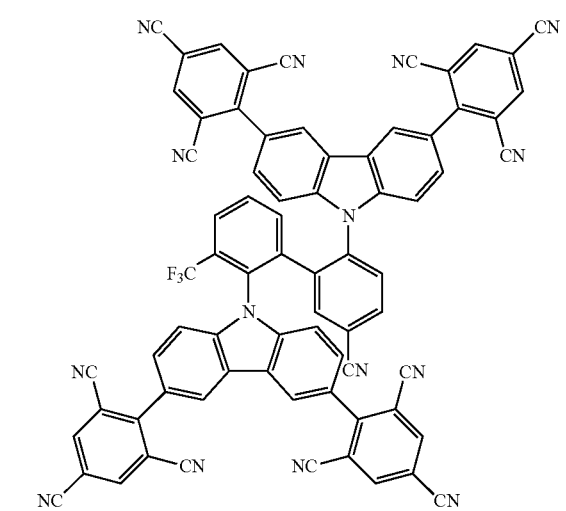
116
-continued
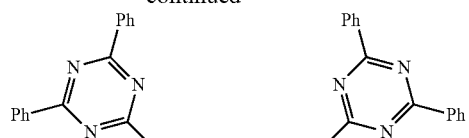
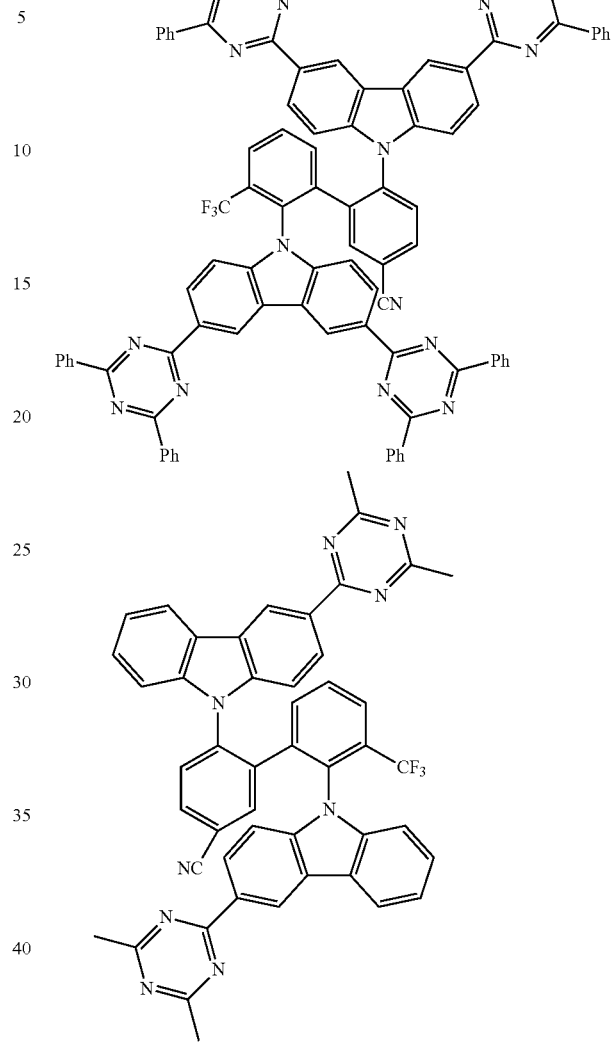
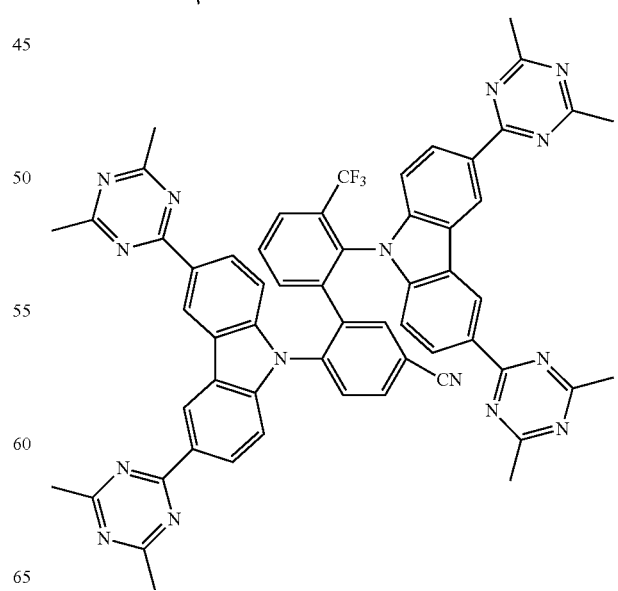

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:
1. An organic molecule comprising a structure of Formula I,

Formula I wherein
T is selected from the group consisting of CN and. $CF_3$;
V, W and Y is independently from each other selected from the group consisting of CN, $CF_3$ and $R^2$;
Z is at each occurrence independently from another selected from the group consisting of a direct bond, $CR^3R^4$, $C=CR^3R^4$, $C=NR^3$, $NR^3$, O, $SiR^3R^4$, S, S(O) and $S(O)_2$;
$R^1$ is at each occurrence independently from another selected from the group consisting of hydrogen, deuterium,
$C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl,
wherein one or more hydrogen atoms are optionally substituted by deuterium; and
$C_6$-$C_{18}$-aryl,
which is optionally substituted with one or more substituents independently from each other selected from the group consisting of Me, $^iPr$, $^tBu$ and Ph;
$R^2$ is at each occurrence independently from another selected from the group consisting of hydrogen, deuterium,
$C_1$-$C_5$-alkyl,
wherein one or more hydrogen atoms are optionally substituted by deuterium;
$C_2$-$C_8$-alkenyl,
wherein one or more hydrogen atoms are optionally substituted by deuterium;
$C_2$-$C_8$-alkynyl,
wherein one or more hydrogen atoms are optionally substituted by deuterium; and
$C_6$-$C_{18}$-aryl,
which is optionally substituted with one or more substituents independently from each other selected from the group consisting of Me, $^iPr$, $^tBu$ and Ph;
$R^a$, $R^3$ and $R^4$ is at each occurrence independently from another selected from the group consisting of: hydrogen, deuterium, $N(R^5)_2$, $OR^5$, $Si(R^5)_3$, $B(OR^5)_2$, $OSO_2R^5$, $CF_3$, CN, F, Br, I,
$C_1$-$C_{40}$-alkyl,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_1$-$C_{40}$-alkoxy,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_1$-$C_{40}$-thioalkoxy,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_2$-$C_{40}$-alkenyl,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_2$-$C_{40}$-alkynyl,
which is optionally substituted with one or more substituents $R^5$ and
wherein one or more non-adjacent $CH_2$-groups are optionally substituted by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$;
$C_6$-$C_{60}$-aryl,
which is optionally substituted with one or more substituents $R^5$; and
$C_3$-$C_{57}$-heteroaryl,
which is optionally substituted with one or more substituents $R^5$;
$R^5$ is at each occurrence independently from another selected from the group consisting of hydrogen, deuterium, $N(R^6)_2$, $OR^6$, $Si(R^6)_3$, $B(OR^6)_2$, $OSO_2R^6$, $CF_3$, CN, F, Br, I,
$C_1$-$C_{40}$-alkyl,
which is optionally substituted with one or more substituents $R^6$ and
wherein one or more non-adjacent $CH_2$-groups are optionally substituted by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$;
$C_1$-$C_{40}$-alkoxy,
which is optionally substituted with one or more substituents $R^6$ and
wherein one or more non-adjacent $CH_2$-groups are optionally substituted by $R^6C=CR^6$, $C\equiv C$, $Si(R^6)_2$, Ge(R⁶)₂, Sn(R⁶)₂, C=O, C=S, C=Se, C=NR⁶, P(=O)(R⁶), SO, SO₂, NR⁶, O, S Or CONR⁶;
C₁-C₄₀-thioalkoxy,
  which is optionally substituted with one or more substituents R⁶ and
  wherein one or more non-adjacent CH₂-groups are optionally substituted by R⁶C=CR⁶, C≡C, Si(R⁶)₂, Ge(R⁶)₂, Sn(R⁶)₂, C=O, C=S, C=Se, C=NR⁶, P(=O)(R⁶), SO, SO₂, NR⁶, O, S or CONR⁶;
C₂-C₄₀-alkenyl,
  which is optionally substituted with one or more substituents R⁶ and
  wherein one or more non-adjacent CH₂-groups are optionally substituted by R⁶C=CR⁶, C≡C, Si(R⁶)₂, Ge(R⁶)₂, Sn(R⁶)₂, C=O, C=S, C=Se, C=NR⁶, P(=O)(R⁶), SO, SO₂, NR⁶, O, S or CONR⁶;
C₂-C₄₀-alkynyl,
  which is optionally substituted with one or more substituents R⁶ and
  wherein one or more non-adjacent CH₂-groups are optionally substituted by R⁶C=CR⁶, C≡C, Si(R⁶)₂, Ge(R⁶)₂, Sn(R⁶)₂, C=O, C=S, C=Se, C=NR⁶, P(=O)(R⁶), SO, SO₂, NR⁶, O, S or CONR⁶;
C₆-C₆₀-aryl,
  which is optionally substituted with one or more substituents R⁶; and
C₃-C₅₇-heteroaryl,
  which is optionally substituted with one or more substituents R⁶;
R⁶ is at each occurrence independently from another selected from the group consisting of:
hydrogen, deuterium, OPh, CF₃, CN, F,
C₁-C₅-alkyl,
  wherein one or more hydrogen atoms are optionally, independently from each other substituted by deuterium, CN, CF₃, or F;
C₁-C₅-alkoxy,
  wherein one or more hydrogen atoms are optionally, independently from each other substituted by deuterium, CN, CF³, or F;
C₁-C₅-thioalkoxy,
  wherein one or more hydrogen atoms are optionally, independently from each other substituted by deuterium, CN, CF₃, or F;
C₂-C₅-alkenyl,
  wherein one or more hydrogen atoms are optionally, independently from each other substituted by deuterium, CN, CF₃, or F;
C₂-C₅-alkynyl,
  wherein one or more hydrogen atoms are optionally, independently from each other substituted by deuterium, CN, CF₃, or F;
C₆-C₁₈-aryl
  which is optionally substituted with one or more C₁-C₅-alkyl substituents;
C₃-C₁₇-heteroaryl,
  which is optionally substituted with one or more C₁-C₅-alkyl substituents;
N(C₆-C₁₈-aryl)₂;
N(C₃-C₁₇-heteroaryl)₂,
and N(C₃-C₁₇-heteroaryl)(C₆-C₁₈-aryl);
wherein
exactly one substituent selected from the group consisting of T, V, W and Y is CN;
and exactly one substituent selected from the group consisting of T, V, W and Y is CF₃.

2. The organic molecule according to claim 1, wherein the molecule comprises a structure of Formula Ia:

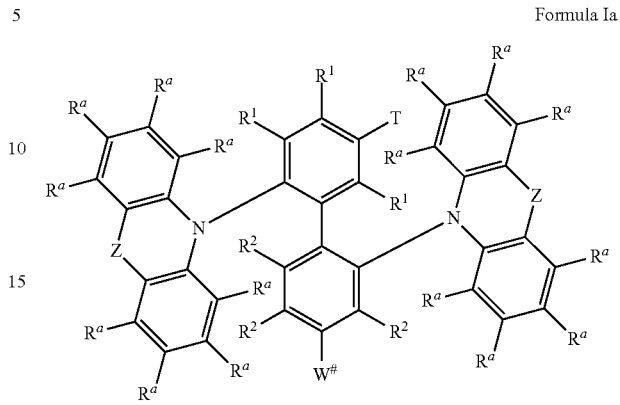

Formula Ia wherein
W# is selected from the group consisting of CN and CF₃, and wherein Z, T, R¹, R² and Rᵃ have the aforestated meanings,
wherein exactly one substituent selected from the group consisting of T and W# is CN;
and exactly one substituent selected from the group consisting of T and W# is CF₃.

3. The organic molecule according to claim 1 wherein the molecule comprises a structure of Formula IIa:

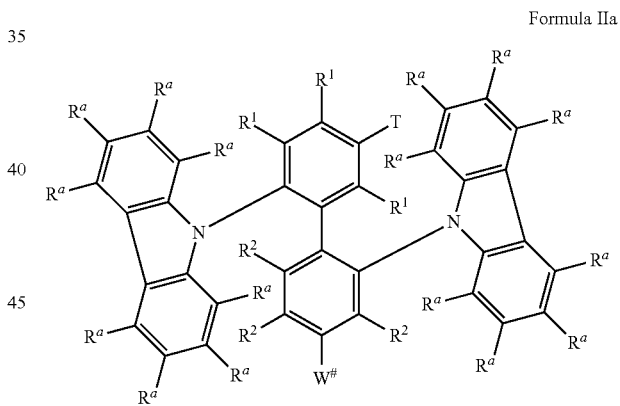

Formula IIa wherein
W# is selected from the group consisting of CN and CF₃, and wherein T, R¹, R² and R³ have the aforestated meanings,
wherein exactly one substituent selected from the group consisting of T and W# is CN;
and exactly one substituent selected from the group consisting of T and W# is CF₃.

4. The organic molecule according to claim 1, wherein R¹ and R² at each occurrence independently from another selected from the group consisting of H, methyl, mesityl, tolyl and phenyl.

5. The organic molecule according claim 1, wherein R¹ and R² are both H.

6. The organic molecule according to claim 1, wherein the molecule comprises a structure of Formula IIb:

Formula IIb

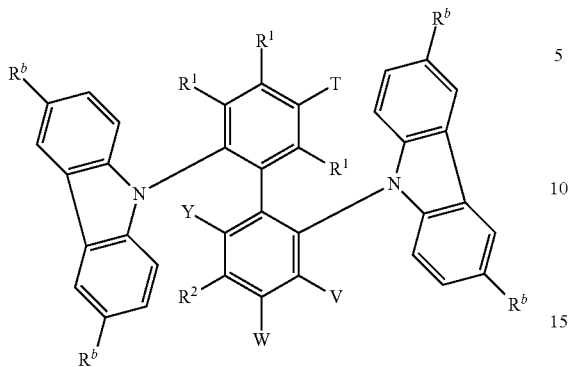

wherein
$R^b$ is at each occurrence independently from another selected from the group consisting of:
deuterium, $N(R^5)_2$, $OR^5$, $Si(R^5)_3$; $B(OR^5)_2$, $OSO_2R^5$, $CF_3$, CN, F, Br, I,
$C_1$-$C_{40}$-alkyl,
  which is optionally substituted with one or more substituents $R^5$ and
  wherein one or more non-adjacent $CH_2$-groups are optionally substituted by $R^5C=CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;
$C_1$-$C_{40}$-alkoxy,
  which is optionally substituted with one or more substituents $R^5$ and
  wherein one or more non-adjacent $CH_2$-groups are optionally substituted by $R^5C=-CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;
$C_1$-$C_{40}$-thioalkoxy,
  which is optionally substituted with one or more substituents $R^5$ and
  wherein one or more non-adjacent $CH_2$-groups are optionally substituted by $R^5C=CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;
$C_2$-$C_{40}$-alkenyl,
  which is optionally substituted with one or more substituents $R^5$ and
  wherein one or more non-adjacent $CH_2$-groups are optionally substituted by $R^5C=CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;
$C_2$-$C_{40}$-alkynyl,
  which is optionally substituted with one or more substituents $R^5$ and
  wherein one or more non-adjacent $CH_2$-groups are optionally substituted by $R^5C=CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;
$C_6$-$C_{60}$-aryl,
  which is optionally substituted with one or more substituents $R^5$; and
$C_3$-$C_{57}$-heteroaryl,
  which is optionally substituted with one or more substituents $R^5$;
and wherein T, Y, W, V, $R^1$ and $R^2$ have the aforestated meanings.

7. The organic molecule according to claim 1, wherein the molecule comprises of a structure of Formula IIc:

Formula IIc

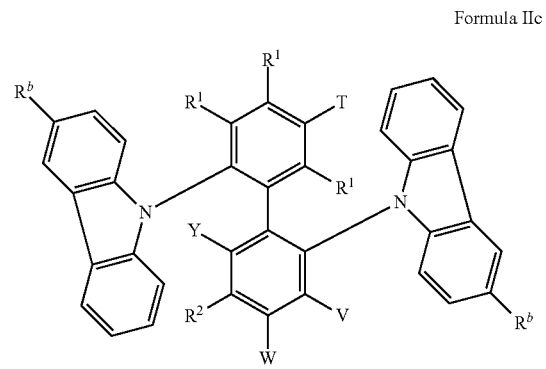

wherein
$R^b$ is at each occurrence independently from another selected from the group consisting of deuterium, $N(R^5)_2$, $OR^5$, $Si(R^5)_3$, $B(OR^5)_2$, $OSO_2R^5$, $CF_3$, CN, F, Br, I,
$C_1$-$C_{40}$-alkyl,
  which is optionally substituted with one or more substituents $R^5$ and
  wherein one or more non-adjacent $CH_2$-groups are optionally substituted by $R^5C=CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;
$C_1$-$C_{40}$-alkoxy,
  which is optionally substituted with one or more substituents $R^5$ and
  wherein one or more non-adjacent $CH_2$-groups are optionally substituted by $R^5C=CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;
$C_1$-$C_{40}$-thioalkoxy,
  which is optionally substituted with one or more substituents $R^5$ and
  wherein one or more non-adjacent $CH_2$-groups are optionally substituted by $R^5C=CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;
$C_2$-$C_{40}$-alkenyl,
  which is optionally substituted with one or more substituents $R^5$ and
  wherein one or more non-adjacent $CH_2$-groups are optionally substituted by $R^5C=CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;
$C_2$-$C_{40}$-alkynyl,
  which is optionally substituted with one or more substituents $R^5$ and
  wherein one or more non-adjacent $CH_2$-groups are optionally substituted by $R^5C=CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$;
$C_6$-$C_{60}$-aryl,
  which is optionally substituted with one or more substituents $R^5$; and
$C_3$-$C_{57}$-heteroaryl,
  which is optionally substituted with one or more substituents $R^5$;
and wherein T, Y, W, V, $R^1$ and $R^2$ have the aforestated meaning.

8. The organic molecule according to claim 6, wherein $R^b$ is at each occurrence independently from another selected from the group consisting of Me, $^i$Pr, $^t$Bu, CN, CF$_3$, Ph, which is optionally substituted with one or more substituents independently from each other selected from the group consisting of Me, $^i$Pr, $^t$Bu, CN, CF$_3$ and Ph;

pyridinyl, which is optionally substituted with one or more substituents independently from each other selected from the group consisting of Me, $^i$Pr, $^t$Bu, CN, CF$_3$ and Ph;

pyrimidinyl, which is optionally substituted with one or more substituents independently from each other selected from the group consisting of Me, $^i$Pr, $^t$Bu, CN, CF$_3$ and Ph;

carbazolyl, which is optionally substituted with one or more substituents independently from each other selected from the group consisting of Me, $^i$Pr, $^t$Bu, CN, CF$_3$ and Ph;

triazinyl, which is optionally substituted with one or more substituents independently from each other selected from the group consisting of Me, $^i$Pr, $^t$Bu, CN, CF$_3$ and Ph;

N(Ph)$_2$.

9. A composition comprising:
(a) at least one organic molecule according to claim 1 as an emitter and/or host;
(b) one or more emitter and/or a host materials different from the at least one organic molecule according to claim 1; and
(c) optionally one or more dyes and/or one or more solvents.

10. An optoelectronic device comprising an organic molecule according to claim 1.

11. The optoelectronic device according to claim 10, wherein the optoelectronic device is an organic light-emitting diode, a light-emitting electrochemical cell, an organic light-emitting sensor an organic diode, an organic solar cell, an organic transistor, an organic field-effect transistor, an organic laser or a down-conversion element.

12. The optoelectronic device according to claim 10, wherein the organic molecule is one of an emitter and an absorber in the optoelectronic device.

13. The optoelectronic device according to claim 10, comprising:
a substrate;
an anode;
a cathode, wherein the anode or the cathode is applied to the substrate; and at least one light-emitting layer disposed between the anode and the cathode and which comprises the organic molecule.

14. An optoelectronic device comprising an organic molecule according to claim 2.

15. The optoelectronic device according to claim 14, wherein the organic molecule is one of an emitter and an absorber in the optoelectronic device.

16. An optoelectronic device comprising the composition according to claim 9.

17. The optoelectronic device according to claim 16, comprising:
a substrate,
an anode;
a cathode, wherein the anode or the cathode is disposed on the substrate; and
at least one light-emitting layer disposed between the anode and the cathode and which comprises the composition.

18. The optoelectronic device according to claim 16, wherein the composition is one of an emitter and an absorber in the optoelectronic device.

19. A method for producing an optoelectronic device, comprising processing of the organic molecule according to claim 1 by a vacuum process evaporation or from a solution.

20. A method for producing an optoelectronic, device, comprising processing of the composition according to claim 9 by a vacuum evaporation process or from a solution.

* * * * *